United States Patent
Faltys et al.

(10) Patent No.: US 6,219,580 B1
(45) Date of Patent: Apr. 17, 2001

(54) MULTICHANNEL COCHLEAR PROSTHESIS WITH FLEXIBLE CONTROL OF STIMULUS WAVEFORMS

(75) Inventors: Michael A. Faltys; Gerald E. Loeb, both of Northridge; Logan P. Palmer, Santa Monica; Andrew W. Voelkel, Venice, all of CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/322,711

(22) Filed: May 28, 1999

Related U.S. Application Data

(63) Continuation-in-part of application No. 08/945,661, filed on Oct. 24, 1997, now Pat. No. 6,002,966, which is a continuation-in-part of application No. 08/429,749, filed on Apr. 26, 1995, now Pat. No. 5,601,617.

(51) Int. Cl.[7] .............................. A61N 1/36; H04R 25/00
(52) U.S. Cl. .................................................. 607/57
(58) Field of Search ........................................ 607/55–57

(56) References Cited

U.S. PATENT DOCUMENTS

| | | |
|---|---|---|
| 4,267,410 | 5/1981 | Forster et al. . |
| 4,408,608 | 10/1983 | Daly et al. . |
| 4,532,930 | 8/1985 | Crosby et al. . |
| 4,612,934 | 9/1986 | Borkan . |
| 4,819,647 | 4/1989 | Byers et al. . |
| 4,991,582 | 2/1991 | Byers et al. . |
| 5,095,904 | 3/1992 | Seligman et al. . |
| 5,522,865 * | 6/1996 | Schulman et al. ............. 607/56 |
| 5,571,148 * | 11/1996 | Loeb et al. .................... 607/57 |
| 5,601,617 | 2/1997 | Loeb et al. . |
| 5,603,726 | 2/1997 | Schulman et al. . |
| 5,800,475 | 9/1998 | Jules . |
| 5,824,022 * | 10/1998 | Zilberman et al. ............. 607/57 |
| 5,983,139 * | 11/1999 | Zierhofer ....................... 607/56 |
| 5,991,663 * | 11/1999 | Irlicht et al. ................... 607/57 |

FOREIGN PATENT DOCUMENTS 9634508  10/1996 (WO) .

\* cited by examiner

*Primary Examiner*—Carl H. Layno
(74) *Attorney, Agent, or Firm*—Bryant R. Gold

(57) ABSTRACT

A cochlear implant system includes an implant portion and an external portion. The external portion performs at least the function of sensing acoustic signals and converting such sensed signals to electrical signals. The implant portion performs at least the function of generating electrical stimuli, modulated and classified in response to the sensed acoustic signals, and intended for direct electrical stimulation of the auditory nerve in accordance with a selected speech processing strategy. Control data defines the selected speech processing strategy, i.e., the pulsatile stimulation pattern to be used by implantable portion. Such control data is transmitted to and stored within the implantable portion of the system only once, when a particular speech processing strategy is selected, thereby eliminating the need to continually resend such speech-processing-defining data over a bandwidth-limited link between the implantable and external portions of the system. The control data that defines the selected speech processing strategy is stored in a stimulation template (also referred to as a "pulse table"), which template or table is stored digitally within the implanted portion of the system. Weighting coefficients (or weighting factors) are stored in the template or table at specified locations to define the speech processing strategy. For example, the columns of the template or table may be used to represent the different current sources, or "stimulous channels", of the implanted portion, and the rows may be used to represent intervals of time. The "stimulous channels" and increments of time thus form the two ordinates of the table, and the table thus consists of a modest number of intervals whose total duration defines a complete "cycle" of stimulation. The instantaneous current flow to be generated by the implanted portion is defined at the beginning of each stimulation cycle by multiplying the weighting factor stored in a particular location within the pulse table by modulation data derived from the sensed acoustic signal. Only modulation data need be sent to the implanted portion on a continuous (real time) basis for the cochlear implant system to function.

15 Claims, 35 Drawing Sheets

SIMULTANEOUS ANALOG STIMULATION BANDPASS FILTERS: EXTENDED FREQUENCY BOUNDARIES (Hz)

| NUMBER OF CHANNELS | FILTER 1 | FILTER 2 | FILTER 3 | FILTER 4 | FILTER 5 | FILTER 6 | FILTER 7 | FILTER 8 |
|---|---|---|---|---|---|---|---|---|
| 8 CHANNELS | 250-500 | 500-875 | 875-1150 | 1150-1450 | 1450-2000 | 2000-2600 | 2600-3800 | 3800-6800 |
| 7 CHANNELS | 250-500 | 500-875 | 875-1150 | 1150-1450 | 1450-2000 | 2000-2600 | 2600-6800 | |
| 6 CHANNELS | 250-500 | 500-875 | 875-1150 | 1150-1750 | 1750-2600 | 2600-6800 | | |
| 5 CHANNELS | 250-500 | 500-875 | 875-1450 | 1450-2600 | 2600-6800 | | | |
| 4 CHANNELS | 250-875 | 875-1450 | 1450-2600 | 2600-6800 | | | | |
| 3 CHANNELS | 250-875 | 875-2600 | 2600-6800 | | | | | |
| 2 CHANNELS | 350-700 | 2200-4400 | | | | | | |
| 1 CHANNEL | 250-6800 | | | | | | | |

CIS BANDPASS FILTERS: EXTENDED FREQUENCY BOUNDARIES (Hz)

| NUMBER OF CHANNELS | FILTER 1 | FILTER 2 | FILTER 3 | FILTER 4 | FILTER 5 | FILTER 6 | FILTER 7 | FILTER 8 |
|---|---|---|---|---|---|---|---|---|
| 8 CHANNELS | 250-500 | 500-730 | 730-1015 | 1015-1450 | 1450-2000 | 2000-2600 | 2600-3800 | 3800-6800 |
| 7 CHANNELS | 250-500 | 500-730 | 730-1150 | 1150-1750 | 1750-2600 | 2600-3800 | 3800-6800 | |
| 6 CHANNELS | 250-580 | 580-875 | 875-1450 | 1450-2000 | 2000-3300 | 3300-6800 | | |
| 5 CHANNELS | 250-580 | 580-1015 | 1015-1750 | 1750-3300 | 3300-6800 | | | |
| 4 CHANNELS | 250-730 | 730-1450 | 1450-2600 | 2600-6800 | | | | |
| 3 CHANNELS | 250-875 | 875-2000 | 2000-6800 | | | | | |
| 2 CHANNELS | 350-700 | 2200-4400 | | | | | | |
| 1 CHANNEL | 250-6800 | | | | | | | |

FIG. 3C

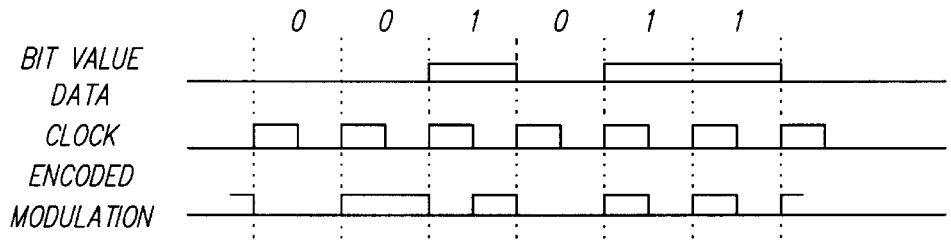
FIG. 17
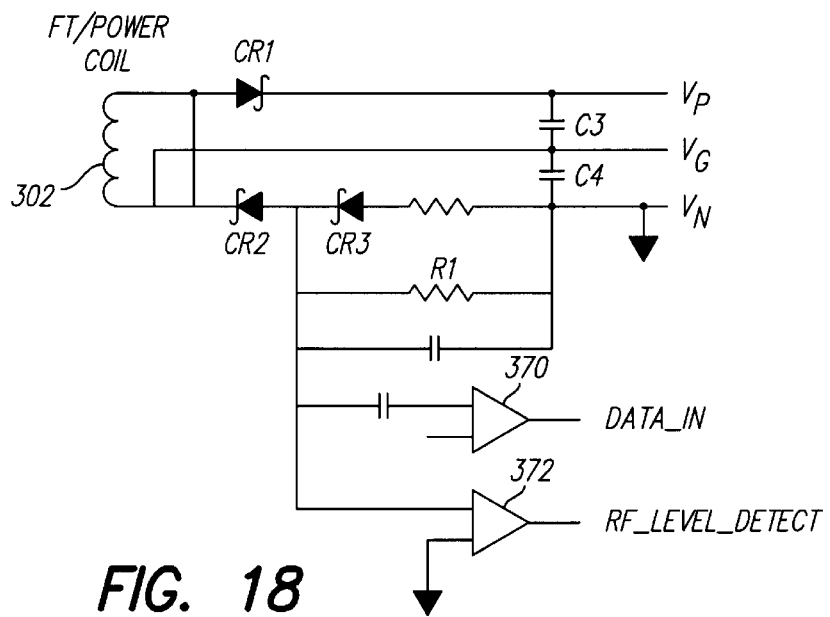
FIG. 18
| 11 | 10 | 9 | 8 | 7 | 6 | 5 | 4 | 3 | 2 | 1 | 0 |
|---|---|---|---|---|---|---|---|---|---|---|---|
| STOP (0) | PARITY | \multicolumn{10}{c|}{REGISTER CONTENTS} | | | | | | | | | START (1) |
FIG. 20

COMMAND WORD FORMAT

| 11 | 10 | 9 | 8 | 7 | 6 | 5 | 4 | 3 | 2 | 1 | 0 |
|---|---|---|---|---|---|---|---|---|---|---|---|
|  | 0 |  |  |  |  | REGISTER ADDRESS | | | | | |

COMMAND WORD FIELD DESCRIPTION

| FIELD | BIT | DESCRIPTION |
|---|---|---|
| PARITY | 11 | Odd parity |
| AMP/CMD | 10 | 0 for command word |
| CMDSEQ | 9 | 0 indicates single-word command or final word in multi-word command. 1 indicates that write data word(s) follow. |
| DIR | 8 | 0 for write, 1 for read. |
| AI | 7 | Auto Increment. Used to increment address counter when addressing RAM. |
| CRC | 6 | Enables checksum operation in writes. |
| REG. ADDR. | 0-5 | Selects one of 63 possible register addresses to read or write. Address x3F selects the Pulse Table RAM, and RAM address is supplied by a separate auto-incrementable address register. |

AMPLITUDE WORD FORMAT

| 11 | 10 | 9 | 8 | 7 | 6 | 5 | 4 | 3 | 2 | 1 | 0 |
|---|---|---|---|---|---|---|---|---|---|---|---|
|  | 1 |  |  | MAGNITUDE | | | | | | | |

AMPLITUDE WORD FIELD DESCRIPTION

| FIELD | BIT | DESCRIPTION |
|---|---|---|
| PARITY | 11 | Odd parity |
| AMP/CMD | 10 | 1 for command word |
| SYNC | 9 | 1 indicates last word in an amplitude frame; 0 otherwise. |
| SIGN OR SKIP | 8 | Normally the amplitude sign bit, this can also be configured as a skip bit for NofM strategies. A 1 value for the sign with a zero magnitude ("negative zero") has special significance: This enables a DAC output to be dynamically shorted to ground. |
| MAG. | 0-7 | 8-bit amplitude magnitude. |

FIG. 19

PULSE TABLE WORD FORMAT

| 17 | 16-13 | 12-9 | 8-7 | 6 | 5 | 4-2 | 1 | 0 |
|---|---|---|---|---|---|---|---|---|
|   |   |   |   |   |   |   |   |   |

PULSE TABLE FIELD DESCRIPTION

| FIELD | BIT | DESCRIPTION |
|---|---|---|
| HOLD | 17 | When set to 1, indicates that the pulse table is ready for the next amplitude frame. Then next pulse table entry will apply to the new frame. (This bit is also referred to as "LOAD" in other documents.) |
| SOURCE | 13-16 | Selects 1 of 16 amplitude words in the frame as the source operand. |
| DEST. | 9-12 | Selects 1 of 16 DAC channels as the destination. |
| RANGE | 7-8 | Scales the source amplitude word by as follows:<br>    0 --amplitude x 1.<br>    1 --amplitude x 2 (shift by 1).<br>    2 --amplitude x 1 (shift by 2).<br>    3 --NOP: Don't update destination. |
| SIGN | 6 | When set 1, inverts the sign of the source amplitude. A 1 value for the SIGN with a zero MULT field ("negative zero") has special significance: This enables a dynamic short to ground the destination DAC output. |
| PASS | 5 | When set to 1, causes the scaled amplitude to be bypass the multiplier ("multiply by 1"). A 0 values enables the multiplier. |
| MULT | 4-2 | Multiplies the scaled amplitude by from 0 to 7/8 in 1/8 increments. |
| PAUSE | 1 | When set to 1, waits for end of the current update (pulse width) interval before proceeding with the next table entry. |
| IMMED | 0 | When set to 1, the following fields are stored as a signed, 11-bit value in an "Immediate" register, and the destination is not updated:<br>    SIGN<br>    DEST<br>    RANGE<br>    PASS<br>    MULT<br>The next table entry adds this Immediate value to the multiplier/pass output, and the result goes to the destination DAC. |

PULSE TABLE

| ADDR | HOLD | SOURCE | DEST | RANGE | SIGN | PASS | MULT | PAUSE | IMMED |
|---|---|---|---|---|---|---|---|---|---|
| 208 | 0 | 0 | 0 | 2 | 1 | 1 | 7 | 0 | 0 |
| 209 | 0 | 0 | 15 | 2 | 0 | 0 | 0 | 1 | 0 |
| 210 | 0 | 0 | 0 | 2 | 0 | 1 | 7 | 1 | 0 |
| 211 | 0 | 0 | 0 | 2 | 0 | 0 | 0 | 0 | 0 |
| 212 | 0 | 1 | 1 | 2 | 1 | 1 | 7 | 1 | 0 |
| 213 | 0 | 1 | 1 | 2 | 0 | 1 | 7 | 1 | 0 |
| 214 | 0 | 0 | 1 | 2 | 0 | 0 | 0 | 0 | 0 |
| 215 | 0 | 2 | 2 | 2 | 1 | 1 | 7 | 1 | 0 |
| 216 | 0 | 2 | 2 | 2 | 0 | 1 | 7 | 1 | 0 |
| 217 | 0 | 0 | 2 | 2 | 0 | 0 | 0 | 0 | 0 |
| 218 | 0 | 3 | 3 | 2 | 1 | 1 | 7 | 1 | 0 |
| 219 | 0 | 3 | 3 | 2 | 0 | 1 | 7 | 1 | 0 |
| 220 | 0 | 0 | 3 | 2 | 0 | 0 | 0 | 0 | 0 |
| 221 | 0 | 4 | 4 | 2 | 1 | 1 | 7 | 1 | 0 |
| 222 | 0 | 4 | 4 | 2 | 0 | 1 | 7 | 1 | 0 |
| 223 | 0 | 0 | 4 | 2 | 0 | 0 | 0 | 0 | 0 |
| 224 | 0 | 5 | 5 | 2 | 1 | 1 | 7 | 1 | 0 |
| 225 | 0 | 5 | 5 | 2 | 0 | 1 | 7 | 1 | 0 |
| 226 | 0 | 0 | 5 | 2 | 0 | 0 | 0 | 0 | 0 |
| 227 | 0 | 6 | 6 | 2 | 1 | 1 | 7 | 1 | 0 |
| 228 | 0 | 6 | 6 | 2 | 0 | 1 | 7 | 1 | 0 |
| 229 | 0 | 0 | 6 | 2 | 0 | 0 | 0 | 0 | 0 |
| 230 | 0 | 7 | 7 | 2 | 1 | 1 | 7 | 1 | 0 |
| 231 | 0 | 7 | 7 | 2 | 0 | 1 | 7 | 1 | 0 |
| 232 | 0 | 0 | 7 | 2 | 0 | 0 | 0 | 0 | 0 |

| | | | | | | | | | |
|---|---|---|---|---|---|---|---|---|---|
| 233 | 0 | 8 | 8 | 2 | 1 | 1 | 7 | 1 | 0 |
| 234 | 0 | 8 | 8 | 2 | 0 | 1 | 7 | 1 | 0 |
| 235 | 0 | 0 | 8 | 2 | 0 | 0 | 0 | 0 | 0 |
| 236 | 0 | 9 | 9 | 2 | 1 | 1 | 7 | 1 | 0 |
| 237 | 0 | 9 | 9 | 2 | 0 | 1 | 7 | 1 | 0 |
| 238 | 0 | 0 | 9 | 2 | 0 | 0 | 0 | 0 | 0 |
| 239 | 0 | 10 | 10 | 2 | 1 | 1 | 7 | 1 | 0 |
| 240 | 0 | 10 | 10 | 2 | 0 | 1 | 7 | 1 | 0 |
| 241 | 0 | 0 | 10 | 2 | 0 | 0 | 0 | 0 | 0 |
| 242 | 0 | 11 | 11 | 2 | 1 | 1 | 7 | 1 | 0 |
| 243 | 0 | 11 | 11 | 2 | 0 | 1 | 7 | 1 | 0 |
| 244 | 0 | 0 | 11 | 2 | 0 | 0 | 0 | 0 | 0 |
| 245 | 0 | 12 | 12 | 2 | 1 | 1 | 7 | 1 | 0 |
| 246 | 0 | 12 | 12 | 2 | 0 | 1 | 7 | 1 | 0 |
| 247 | 0 | 0 | 12 | 2 | 0 | 0 | 0 | 0 | 0 |
| 248 | 0 | 13 | 13 | 2 | 1 | 1 | 7 | 1 | 0 |
| 249 | 0 | 13 | 13 | 2 | 0 | 1 | 7 | 1 | 0 |
| 250 | 0 | 0 | 13 | 2 | 0 | 0 | 0 | 0 | 0 |
| 251 | 0 | 14 | 14 | 2 | 1 | 1 | 7 | 1 | 0 |
| 252 | 0 | 14 | 14 | 2 | 0 | 1 | 7 | 1 | 0 |
| 253 | 0 | 0 | 14 | 2 | 0 | 0 | 0 | 0 | 0 |
| 254 | 0 | 15 | 15 | 2 | 1 | 1 | 7 | 1 | 0 |
| 255 | 1 | 15 | 15 | 2 | 0 | 1 | 7 | 1 | 0 |

FIG. 26A-2

EXAMPLE AMPLITUDE FRAMES

| TIME | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| 0 | 64 | 64 | 64 | 64 | 64 | 64 | 64 | 64 | 64 | 64 | 64 | 64 | 64 | 64 | 64 | 64 |
| 640 | 127 | 127 | 127 | 127 | 127 | 127 | 127 | 127 | 127 | 127 | 127 | 127 | 127 | 127 | 127 | 127 |
| 1280 | 191 | 191 | 191 | 191 | 191 | 191 | 191 | 191 | 191 | 191 | 191 | 191 | 191 | 191 | 191 | 191 |
| 1920 | 255 | 255 | 255 | 255 | 255 | 255 | 255 | 255 | 255 | 255 | 255 | 255 | 255 | 255 | 255 | 255 |

FIG. 26B

EXAMPLE AMPLITUDE FRAMES

| TIME | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| 0 | 205 | 99 | 292 | 416 | 495 | 507 | 448 | 335 | 215 | 253 | 185 | 380 | 409 | 503 | 1 | |
| 180 | 14 | 510 | 303 | 247 | 121 | 215 | 443 | 471 | 503 | 80 | 254 | | | | | |
| 360 | 258 | 413 | 247 | 489 | 118 | 45 | 488 | 84 | 417 | 151 | 491 | 236 | 291 | 448 | 233 | 510 |
| 570 | 348 | 339 | 208 | 194 | 378 | 368 | 506 | 31 | 232 | 425 | 390 | 247 | 269 | 243 | 471 | 133 |
| 810 | 434 | 43 | 478 | 67 | 319 | 154 | 254 | 59 | 510 | 482 | 428 | 189 | 140 | | | |

| ADDR | HOLD | SOURCE | DEST | RANGE | SIGN | PASS | MULT | PAUSE | IMMED |
|---|---|---|---|---|---|---|---|---|---|
| 110 | 0 | 0 | 0 | 2 | 0 | 1 | 7 | 0 | 0 |
| 111 | 0 | 0 | 1 | 2 | 1 | 1 | 7 | 0 | 0 |
| 112 | 0 | 1 | 2 | 2 | 0 | 1 | 7 | 0 | 0 |
| 113 | 0 | 1 | 3 | 2 | 1 | 1 | 7 | 0 | 0 |
| 114 | 0 | 2 | 4 | 2 | 0 | 1 | 7 | 0 | 0 |
| 115 | 0 | 2 | 5 | 2 | 1 | 1 | 7 | 0 | 0 |
| 116 | 0 | 3 | 6 | 2 | 0 | 1 | 7 | 0 | 0 |
| 117 | 0 | 3 | 7 | 2 | 1 | 1 | 7 | 0 | 0 |
| 118 | 0 | 4 | 8 | 2 | 0 | 1 | 7 | 0 | 0 |
| 119 | 0 | 4 | 9 | 2 | 1 | 1 | 7 | 0 | 0 |
| 120 | 0 | 5 | 10 | 2 | 0 | 1 | 7 | 0 | 0 |
| 121 | 0 | 5 | 11 | 2 | 1 | 1 | 7 | 0 | 0 |
| 122 | 0 | 6 | 12 | 2 | 0 | 1 | 7 | 0 | 0 |
| 123 | 0 | 6 | 13 | 2 | 1 | 1 | 7 | 0 | 0 |
| 124 | 0 | 7 | 14 | 2 | 0 | 1 | 7 | 0 | 0 |
| 125 | 0 | 7 | 15 | 2 | 1 | 1 | 7 | 1 | 0 |
| 126 | 0 | 8 | 14 | 2 | 0 | 1 | 7 | 0 | 0 |
| 127 | 0 | 8 | 15 | 2 | 1 | 1 | 7 | 1 | 0 |
| 128 | 0 | 9 | 12 | 2 | 0 | 1 | 7 | 0 | 0 |
| 129 | 0 | 9 | 13 | 2 | 1 | 1 | 7 | 0 | 0 |
| 130 | 0 | 10 | 14 | 2 | 0 | 1 | 7 | 0 | 0 |
| 131 | 0 | 10 | 15 | 2 | 1 | 1 | 7 | 1 | 0 |
| 132 | 0 | 11 | 14 | 2 | 0 | 1 | 7 | 0 | 0 |
| 133 | 0 | 11 | 15 | 2 | 1 | 1 | 7 | 1 | 0 |
| 134 | 0 | 12 | 12 | 2 | 0 | 1 | 7 | 0 | 0 |
| 135 | 0 | 12 | 13 | 2 | 1 | 1 | 7 | 0 | 0 |

FIG. 28A-2

| 136 | 0 | 13 | 14 | 2 | 0 | 1 | 7 | 0 | 0 |
|---|---|---|---|---|---|---|---|---|---|
| 137 | 0 | 13 | 15 | 2 | 1 | 1 | 7 | 1 | 0 |
| 138 | 0 | 14 | 14 | 2 | 0 | 1 | 7 | 0 | 0 |
| 139 | 1 | 14 | 15 | 2 | 1 | 1 | 7 | 1 | 0 |
| • | | | | | | | | | |
| • | | | | | | | | | |
| 234 | 0 | 12 | 14 | 2 | 0 | 1 | 7 | 0 | 0 |
| 235 | 1 | 12 | 15 | 2 | 1 | 1 | 7 | 1 | 0 |
| 236 | 0 | 0 | 8 | 2 | 0 | 1 | 7 | 0 | 0 |
| 237 | 0 | 0 | 9 | 2 | 1 | 1 | 7 | 0 | 0 |
| 238 | 0 | 1 | 10 | 2 | 0 | 1 | 7 | 0 | 0 |
| 239 | 0 | 1 | 11 | 2 | 1 | 1 | 7 | 0 | 0 |
| 240 | 0 | 2 | 12 | 2 | 0 | 1 | 7 | 0 | 0 |
| 241 | 0 | 2 | 13 | 2 | 1 | 1 | 7 | 0 | 0 |
| 242 | 0 | 3 | 14 | 2 | 0 | 1 | 7 | 0 | 0 |
| 243 | 0 | 3 | 15 | 2 | 1 | 1 | 7 | 1 | 0 |
| 244 | 0 | 4 | 14 | 2 | 0 | 1 | 7 | 0 | 0 |
| 245 | 0 | 4 | 15 | 2 | 1 | 1 | 7 | 1 | 0 |
| 246 | 0 | 5 | 12 | 2 | 0 | 1 | 7 | 0 | 0 |
| 247 | 0 | 5 | 13 | 2 | 1 | 1 | 7 | 0 | 0 |
| 248 | 0 | 6 | 14 | 2 | 0 | 1 | 7 | 0 | 0 |
| 249 | 0 | 6 | 15 | 2 | 1 | 1 | 7 | 1 | 0 |
| 250 | 0 | 7 | 14 | 2 | 0 | 1 | 7 | 0 | 0 |
| 251 | 0 | 7 | 15 | 2 | 1 | 1 | 7 | 1 | 0 |
| 252 | 0 | 8 | 12 | 2 | 0 | 1 | 7 | 0 | 0 |
| 253 | 0 | 8 | 13 | 2 | 1 | 1 | 7 | 0 | 0 |
| 254 | 0 | 9 | 14 | 2 | 0 | 1 | 7 | 0 | 0 |
| 255 | 1 | 9 | 15 | 2 | 1 | 1 | 7 | 1 | 0 |

MULTICHANNEL COCHLEAR PROSTHESIS WITH FLEXIBLE CONTROL OF STIMULUS WAVEFORMS

CROSS REFERENCE TO RELATED APPLICATIONS

This application is a continuation-in-part of U.S. application Ser. No. 08/945,661, filed Oct. 24, 1997 now U.S. Pat. No. 6,002,966; which is a continuation-in-part of U.S. application Ser. No. 08/429,749, filed Apr. 26, 1995, now U.S. Pat. No. 5,601,617, which application and patent are incorporated herein by reference. The invention described in this application is further closely related to the invention described in copending patent application Ser. No. 09/322,712, filed concurrently herewith, entitled "Strategy Selector For Multichannel Cochlear Prosthesis", which application is also incorporated herein by reference.

STATEMENT—FEDERALLY SPONSORED RESEARCH OR DEVELOPMENT

Not applicable.

BACKGROUND OF THE INVENTION

The present invention relates to multichannel cochlear prosthesis, and more particularly to a multichannel cochlear prosthesis that offers flexible control of the stimulus waveforms.

Cochlear prostheses produce sensations of sound in deaf patients by direct electrical stimulation of the auditory nerve. In modern, multichannel cochlear prostheses, several different sites are stimulated at various distances along the cochlea to evoke the different pitches of sound perception that are normally encoded by nerve activity originating from the respective sites. The patterns of electrical stimulation are derived from acoustic signals picked up by a microphone and transformed by a so-called speech processor that is programmed to meet the particular requirements of each patient. Several different schemes for processing the acoustic signal and transforming it into electrical stimuli have been developed and are well-described in the scientific literature and various patents. All of these schemes can be divided into two basic types on the basis of the waveforms of the electrical stimuli:

i) Analog waveforms, which are essentially filtered versions of the continuous acoustic waveform. Analog waveforms usually involve dynamic range compression, bandpass filtering and scaling to the stimulus current ranges that evoke a satisfactory range of auditory sensations from threshold of perception to maximal comfortable loudness. This produces a rich but poorly controlled set of resultant waveforms.

ii) Biphasic pulses, or more generally, multiphasic pulses, commonly referred to as "pulsatile" waveforms. Biphasic pulses consist of a single cycle of a square wave in which current flows in one direction at a specified magnitude and for a specified brief period of time and is followed immediately by an opposite direction of current of a similar magnitude and duration. Multiphasic pulses comprise a plurality of pulsed waves, i.e., a train of pulses, in which current flows first in one direction, then in another direction, and so on, as required, at specified magnitudes and brief periods of time, in such a way that the charge associated with the total of all the plural pulses is balanced, whereby the net electrical charge delivered to the tissue over one multiphasic cycle is zero. Multiphasic pulses, including biphasic pulses, as used in the prior art are most often delivered in sequence to various sites, with the instantaneous magnitude at each site proportional to some measure of the amount of energy present in a particular frequency band of the acoustic waveform. The result is an impoverished but precisely controlled set of stimulus waveforms.

Both of these stimulus waveform types have been selected because they are relatively easy to produce and modulate electronically for real-time encoding of speech and because they guarantee a charge-balanced alternating current at the electrodes, avoiding net direct current that is known to cause electrolytic damage to both electrodes and body tissues.

Recent findings regarding the complex biophysical phenomena associated with the electrical excitation of neurons and psychophysical phenomena regarding the interpretation of neural activity by the auditory nervous system suggest that the quality and intelligibility of speech percepts evoked by a cochlear prosthesis may be improved in a given patient by more specific manipulations of the electrical stimulus waveforms tailored to that patient. In particular, more complex sequences of polarities, with or without pauses between phases and sites, and with or without simultaneous current delivery at more than one site, appear to be desirable. There is thus a need in the art for a cochlear stimulation system that allows complex stimulation waveforms to be individually tailored for each stimulation site.

The recurring or cyclical manner in which complex or other stimulation waveforms are individually tailored for application to each stimulation site is referred to as a "speech processing strategy". For purposes of the present application, a speech processing strategy thus defines the spatiotemporal manner in which either of the above two types of stimulus waveforms are applied to the cochlea of a patient. The spatial application of the stimulus waveforms is controlled by the type of electrode coupling, e.g., bipolar or monopolar, through which the stimuli are applied to various locations along the inside of the scala tympani duct of the spiral-shaped cochlea. The temporal application of the stimulation waveforms is derived by the timing of the stimuli.

Traditionally, speech processing strategies have thus been classified as either: (1) a simultaneous strategy, or (2) a non-simultaneous, or sequential, strategy. Analog waveforms have traditionally been applied as part of a simultaneous strategy, relying on the more highly focused stimulation provided by bipolar coupling to produce an electrical pattern that will yield speech intelligibility. Short, non-simultaneous, biphasic or multiphasic pulses, on the other hand, are usually applied as part of a sequential speech processing strategy, relying on the highly precise sequence of stimulation pulses through monopolar coupling to produce the electrical pattern that yields speech intelligibility. In a typical sequential, or non-simultaneous, strategy, short biphasic or multiphasic pulses are applied in rapid succession (with little or no time overlap) in a specified pattern to each of multiple channels.

Not all patients benefit from the same speech processing strategy. That is, the complex biophysical phenomena associated with the electrical excitation of neurons and psychophysical phenomena regarding the interpretation of neural activity by the auditory nervous system suggest that the quality and intelligibility of speech percepts evoked by a cochlear prosthesis may be improved in a given patient by more specific manipulations of the electrical stimulus waveforms tailored to that patient. However, heretofore it has been particularly difficult and problematic to manipulate the electrical stimuli in a meaningful manner. There is thus a need in the art for an improved technique or method through which specific manipulations of the electrical stimuli may be tailored and tested by a given patient.

One of the difficulties encountered when trying to formulate or manipulate electrical stimuli in a more meaningful and specific manner has been to efficiently send or transmit all of the needed control data associated with a selected speech processing strategy to the implanted stimulator. This difficulty is compounded when one considers the complexity of, e.g., the multichannel pulsatile speech processing strategies that have recently been developed. A representative description of some of these speech processing strategies may be found in Applicant Faltys' copending U.S. patent application Ser. No. 09/322,712, filed concurrently herewith (Attorney Docket No. AB-072A), which application is incorporated herein by reference. Disadvantageously, the limited bandwidth characteristics of most data information channels established with an implant device have heretofore prevented the efficient transfer of data to the implant device. Here, by "efficient transfer", it is meant a transfer of data at sufficiently low power and at a sufficiently high data rate to allow the data, when received in the implant device, to be effectively used for its intended purpose of defining complex spatiotemporal stimulous patterns on a multiplicity of channels without unduly slowing down the operation of the device. There is thus a need for a more efficient transfer link to an implant device, such as cochlear stimulator.

When a cochlear implant system is first provided to a patient, including implanting any implantable components of the system into the patient (which implantable components typically include at least an electrode and a stimulator, and may also include, for fully implantable systems, a speech processor, a microphone and/or a rechargeable power source), it is necessary to initially "fit" or "adjust" the system. As used herein, it should be noted that the terms "fit", "adjust","fitting" or "adjusting" relate to making electronic or software-programming changes to the system, as opposed to making physical or hardware changes, for the purpose of making the system better perform its intended function of helping the deaf patient to sense sound. Where more than one speech processing strategy is available within the implant system, selecting a speech processing strategy that is best suited for a particular patient thus becomes a key part of the "fitting" or "adjusting" process. Moreover, it should be recognized that the fitting or adjusting process will typically continue to occur at regular or as-needed maintenance/check-up intervals after the initial fitting. Thus, it is seen that where more than one speech processing strategy is available within the implant system, the patient, e.g., through the assistance of his or her physician or audiologist, may receive the benefit of, or at least try out during a trial period, one or more different speech processing strategies than was used initially.

Disadvantageously, not all cochlear implant systems are capable of providing more than one speech processing strategy, or of providing both simultaneous and non-simultaneous speech processing strategies. Rather, most commercially-available cochlear implant systems provide just one type of strategy (simultaneous or non-simultaneous), although some may offer, for example, multiple non-simultaneous strategies. Hence, with these one-type-strategy devices, the patient, and/or the physician/audiologist fitting the patient, has no, or only a very limited, ability to select a suitable speech processing strategy that is most effective for that patient. It is therefore seen that there is a need in the art for a more effective way of making different types of speech processing strategies available to a cochlear implant user.

BRIEF SUMMARY OF THE INVENTION

The present invention addresses the above and other needs by providing a cochlear implant system that includes an implant portion and an external portion, and wherein the external portion performs at least the function of sensing acoustic signals and converting such sensed signals to electrical signals, and wherein the implant portion performs at least the function of generating electrical stimuli, modulated and classified in response to the sensed acoustic signals, and intended for direct electrical stimulation of the auditory nerve. A key feature of the present invention is that control data which defines a selected pulsatile stimulation pattern to be used by implantable portion, i.e., the control data that defines a portion of the particular speech processing strategy to be used, is transmitted to and stored within the implantable portion of the system just once, when selected, thereby eliminating the need to continually resend such data over a bandwidth-limited link between the implantable and external portions of the system.

The cochlear implant system of the present invention further provides a method and/or system whereby a rich set of spatiotemporal patterns of electrical stimulation can be defined and tested by an audiologist in the process of fitting the cochlear prosthesis, and in which desirable patterns of pulsatile stimuli of almost arbitrary complexity can be modulated in real-time by the acoustic signal to produce useful perceptions of sound in otherwise deaf patients.

As indicated above, a cochlear implant system provided in accordance with the present invention typically includes an external (non-implanted) portion and an implanted portion. The external portion includes at least a microphone and appropriate amplification circuitry, typically referred to as analog front end (AFE) circuitry, for sensing acoustic sounds and converting them to corresponding electrical signals. The implanted portion includes at least an implantable cochlear stimulator (ICS), including an electrode array inserted into the cochlea and connected to the ICS. The cochlear implant system further includes, in between the external AFE circuitry and the implanted ICS, a speech processor (SP). It is the function of the SP to respond to the electrical signals produced by the microphone and AFE circuitry and generate a set of control signals in accordance with a selected speech processing strategy, modulated as required by the microphone-produced electrical signals, that are sent to the ICS. The ICS, in turn, responds to this set of control signals to produce the spatiotemporal electrical stimuli defined by the speech processing strategy for application to the auditory nerve through the electrode array implanted within the cochlea. A key feature of the present invention is that some or all of the processing circuitry used within the SP may be included within the implanted portion of the implant system, thereby minimizing the amount of information that must be transmitted through a bandwidth-limited transcutaneous communication link established between the external portion and the implanted portion of the system. This is in contrast to prior art cochlear implant systems wherein the SP portion of the system has always resided exclusively within the external portion of the system.

The external portion of the system typically includes a headpiece of some kind. The headpiece, when used, is typically adapted to be worn by a patient in or behind the ear. The microphone is usually incorporated into the headpiece.

Also within the headpiece, or coupled to the headpiece, is a battery, or equivalent power source, and other electronic circuitry as needed to operate the microphone, establish a transcutaneous communication link (over which both data and power may be sent to the implanted portion of the system), and perform appropriate SP functions that are not included within the implanted portion of the system. That is, the headpiece generally includes an antenna, or coil, for transmitting signals to, and receiving signals from, the implantable portion of the system.

The implantable portion of the implant system is adapted to be implanted so that it can readily receive signals from, and (in some embodiments) send signals to, the externally-worn headpiece and/or other external components.

Typically, the implantable portion of the system, frequently referred to as an implantable cochlear stimulator (ICS), contains no power source, but rather receives its operating power from the signals that are coupled or transmitted to it from the external portion of the system. However, it is to be emphasized that the present invention is not limited to an ICS that is powered only from the external system, but applies to any implantable stimulation system that is controlled by an external system or that operates autonomously by means of batteries and internal means for detecting and processing sound information.

The implantable portion of the system or ICS employs a multiplicity of electrical current sources, each connected to at least one electrode contact that defines a stimulation site within the cochlea. Electronic circuitry is also included in the implantable system that permits the sign (polarity) and magnitude of the output current of each of the current sources to be electronically re-specified at frequent or other specified intervals.

In operation, the speech processor defines or specifies the complex stimulation waveforms that are to be used by the ICS, and transmits such definition/specification to the ICS at frequent, predetermined intervals. The ICS responds by generating such complex stimulation waveforms at the times, and for the durations, indicated in the received definition/specification, and then applies such generated waveforms to designated tissue sites, i.e., to specific electrode contacts that are positioned within the cochlea (or other living tissue).

In accordance with one aspect of the invention, a template (also referred to as a "pulse table") of the desired temporal sequence of output currents from the various current sources within the ICS is stored digitally within the speech processor as a table of weighting coefficients (or weighting factors). Such table may be realized using any suitable memory element having addressable memory storage locations. In such a table, the columns (or, alternatively, rows, or other addressable memory locations) represent the different current sources, or "stimulous channels", of the ICS, and the rows (or, alternatively, columns, or other addressable memory locations) represent intervals of time. The "stimulous channels" and increments of time thus form the two ordinates of the table (or other memory means). Such table may also contain additional columns that control other aspects of the stimulation, such as the connection of electrode contacts to the current sources. The template thus consists of a modest number of intervals (typically 20–100) whose total duration defines a complete "cycle" of stimulation. At the beginning of each new stimulation cycle, for example, information derived from the acoustical signal during a previous cycle (or other data-gathering time period), also referred to herein as "modulation data", is used to compute the magnitude of stimulation current required for each of the current sources of the ICS during the new cycle. In each successive interval of the new cycle, the instantaneous current flow to be generated from each of the current sources during the new cycle is determined by a product signal. The product signal is obtained by multiplying the magnitude of stimulation (obtained from the sensed acoustic information, i.e., the modulation data) by the corresponding weighting factor stored in a particular location within the pulse table or other memory means (where such weighting factor and its stored location within the table, i.e., its address, define the speech processing strategy that is to be used). This product signal is thus transferred to the ICS during each interval of the new cycle, where it is acted upon by the electronic circuitry within the ICS to generate the specified instantaneous current flow at the appropriate time.

It is a feature of the present invention that the product signal which is transferred to the ICS during each interval of a new cycle does not have to be sent across a limited-bandwidth transcutaneous transmission link. Rather, in an implant system realized in accordance with the present invention, the template or pulse table, or equivalent memory element, is stored or otherwise located in the implanted portion of the system. This means that, after the appropriate weighting factors and other data been loaded into the pulse table at the specified storage locations (addresses), which loading need only occur once each time a different speech processing strategy is selected or other data needs to be updated, the only information that must be transmitted across the limited-bandwidth transcutaneous transmission link during each stimulation cycle is the modulation data, i.e., the acoustical information sensed through the microphone. Advantageously, such modulation data typically has a much lower bandwidth requirement than does the product signal that has heretofore been sent across the transcutaneous transmission link.

Another important aspect of the invention relates to the use of an internal digital signal generator that adds its generated signal to the modulated signal, which modulated signal is representative of the acoustical signal sensed through the external microphone or other acoustical-to-electrical transducer. The signal generated by such internal digital signal generator is used as a neural conditioning signal to place the nuerons associated with the spiral ganglion cells in a stochastic mode where they will be more receptive to the stimuli to be provided for the purpose of extracting speech features from such stimulation. Advantageously, such neural conditioning signal may be generated within the implant portion of the system using a pattern of data stored in the pulse table.

The present invention may thus be characterized as a multichannel cochlear implant system that includes: (1) an external portion that includes at least an acoustic transducer, e.g., a microphone, for sensing acoustic signals and converting them to electrical signals, and analog front end (AFE) circuitry for preliminarily processing the electrical signals produced by the microphone; (2) an implantable portion that includes at least an electrode array for implantation in the cochlea, and an implantable cochlear stimulator (ICS) connected to the electrode array for generating electrical stimuli defined by control signals; and (3) a speech processor (SP) that generates the control signals used by the ICS so that the electrical stimuli generated by the ICS are modulated by the sensed acoustic signals in accordance with a selected speech processing strategy. Advantageously, that portion of the speech processor responsible for defining the speech processing strategy is located within the implantable portion of the system, whereby only modulation data corresponding to the sensed acoustic signals need be continuously sent to the implantable portion of the system from the external portion of the system during use of the system. one embodiment of the invention, that portion of the speech processor included within the implantable portion of the system includes: (i) template table wherein a set of coefficients are stored that represent a particular spatiotemporal pattern of stimulus waveforms, and (ii) a multiplier that multiplies the set of coefficients stored in the template table with modulation data derived from the sensed acoustic signals to produce a product signal, wherein the product signal specifies a particular spatiotemporal pattern of controlled stimulus waveforms associated with the selected speech processing strategy.

It is thus a feature of the present invention to facilitate the definition/specification of a wide range of different spatiotemporal patterns of electrical stimulation current that can be generated by an implantable cochlear stimulator.

It is another feature of the invention to allow complex stimulation waveforms to be defined/specified in a simple manner.

It is yet an additional feature of the invention, in accordance with one aspect thereof, to allow the definition/specification of the stimulation current to be created simply by writing appropriate numbers or data values (e.g., alpha-numerical values) into a table that defines a current stimulation template, with one of the rows or columns of the table defining time, and with the other of the rows or columns defining electrode pairs (which electrode pairs, once implanted, define specific stimulation sites within the cochlea). Thus, the intersection of a given row and column of the table simply specifies the magnitude, polarity, and time during which the specified stimulation current is applied to one or more given electrode pairs (stimulation site).

It is a further feature of the invention to allow the cycles of stimulation information that are sent to an implanted stimulator to be selectively shortened so that the stimulation information on higher frequency channels can be sent at a higher rate, while lower frequency channels can be updated less frequently.

It is yet another feature of the present invention to provide a cochlear implant system that facilitates the definition of complex stimulation waveforms to be used as part of the selected speech processing strategy, thereby enhancing the ability of the system to produce useful perceptions of sound for a deaf patient.

It is an additional feature of the invention to provide such a cochlear implant system wherein the speech processing functions of such system are allocated between both external and implanted portions of the system in such a way that the amount of information that must be coupled between the external and implanted portions in order for the system to function is minimized, thereby decreasing the bandwidth requirements for whatever type of data transmission link is established between the external and implanted portions of the system.

BRIEF DESCRIPTION OF THE DRAWINGS

The above and other aspects, features and advantages of the present invention will be more apparent from the following more particular description thereof, presented in conjunction with the following drawings wherein:

FIG. 3C presents a preferred frequency map for the filter bank used within the speech processor for two different speech processing strategies;

FIG. 17 is a waveform diagram that illustrates the forward telemetry data encoding used with the ICS;

FIG. 18 is a block diagram that illustrates the forward telemetry data detector used within the preferred ICS;

FIG. 19 illustrates the forward telemetry data formats used with the preferred ICS of FIG. 15;

FIG. 20 shows the back telemetry data format used with the preferred ICS of FIG. 15;

FIG. 21 shows the Pulse Table Word Format, and accompanying Pulse Table Field Descriptions;

FIG. 26A is an exemplary Pulse Table in accordance with the present invention used with a 16channel CIS speech processing strategy;

FIG. 26B is a table that presents exemplary amplitude frames used with the 16-channel CIS speech processing strategy;

FIG. 28A is a exemplary Pulse Table used with an 8-channel SAS speech processing strategy;

FIG. 28B is a table that shows exemplary amplitude frames used with the 8-channel SAS speech processing strategy.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention relates to a method and system for permitting a wide variety of complex stimulation patterns and waveforms to be used by a multi-channel implantable cochlear stimulator. The invention may be used with any multi-channel stimulator that includes the ability to set a prescribed pattern of stimulation waveforms for each channel of the stimulator. As indicated previously, the invention relates to a cochlear implant system that includes an implant portion and an external portion, and wherein the external portion performs at least the function of sensing acoustic signals and converting such sensed signals to electrical signals, and wherein the implant portion performs at least the function of generating electrical stimuli, modulated and classified in response to the sensed acoustic signals, and intended for direct electrical stimulation of the auditory nerve. A key feature of the invention is that control data which defines a selected pulsatile stimulation pattern to be used by the implantable portion, i.e., the control data that defines the particular speech processing strategy to be used, is transmitted to and stored within the implantable portion of the system just once, when selected, thereby eliminating the need to continually resend such data over a bandwidth-limited link between the implantable and external portions of the system.

It is to be noted that much of the description of the invention which follows describes the invention in terms of the Clarion® cochlear implant system, commercially available from Advanced Bionics Corporation, of Sylmar Calif. However, it is to be understood that the invention is not limited to the Clarion® cochlear implant system, per se. Rather, the invention is directed to any cochlear implant system wherein, once a particular speech processing strategy has been selected for use by the implant system, the speech-processing-strategy-defining-data that implements the selected strategy is sent to and stored within the implantable portion of the system so that thereafter only acoustic modulating data need be continuously sent to the implantable portion when the system is in use.

Figure 1:
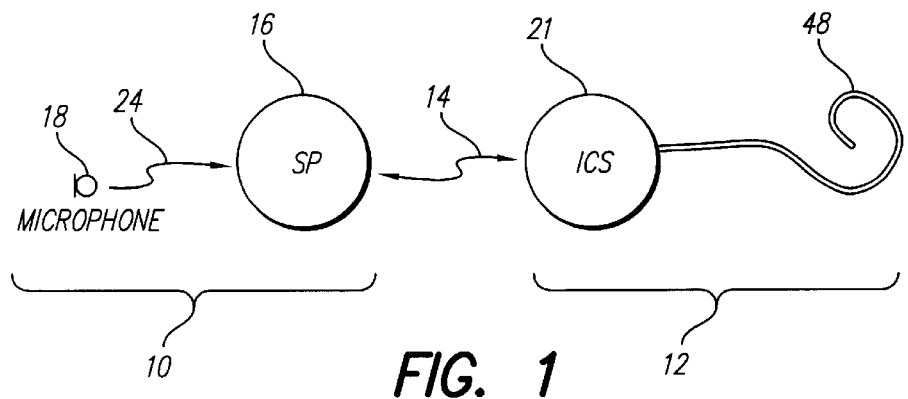
FIG. 1 shows a generalized block diagram of a cochlear implant system, including a microphone, a speech processor (SP), an implantable cochlear stimulator (ICS) and an electrode array.

Turning then to FIG. 1, the present invention will be described. As seen in FIG. 1, a cochlear stimulation system is shown that includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. The cochlear stimulation portion 12 includes an implantable cochlear stimulator (ICS) 21, and an electrode array 48. The electrode array 48 is adapted to be inserted within the cochlea of a patient. The array 48 includes a multiplicity of electrodes, e.g., sixteen electrodes, spaced along its length that are selectively connected to the ICS 21. The electrode array 48 may be substantially as shown and described in U.S. Pat. No. 4,819,647, incorporated herein by reference, or U.S. patent application Ser. No. 09/247,734, filed Feb. 9, 1999 (Attorney Docket AB-034A3), "Cochlear Electrode Array With Electrode Contacts on Medial Side", also incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 1 as being linked together electronically through a suitable data or communications link 14. In some cochlear implant systems, e.g., prior art systems, the SP 16 and microphone 18 comprise the external portion of the cochlear implant system; and the ICS 21 and electrode array 48 comprise the implantable portion of the system. Thus, the data link 14 is a transcutaneous data link that allows power and control signals to be sent from the SP16 to the ICS 21. In some embodiments, data and status signals may also be sent from the ICS 21 to the SP 16.

In accordance with the present invention, and as shown more particularly below in FIG. 3A, and FIGS. 14–29, at least certain portions of the SP 16 are included within the implantable portion of the overall cochlear implant system, while other portions of the SP 16 remain in the external portion of the system. In general, at least the microphone 18 and associated analog front end (AFE) circuitry will be part of the external portion of the system; and at least the ICS 21 and electrode array 48 are part of the implantable portion of the invention. As used herein, "external" means not implanted under the skin or residing within the inner ear. However, "external" may mean within the outer ear, including in the ear canal, and may also include within the middle ear.

Typically, where a transcutaneous data link must be established between the external portion and implantable portions of the system, such link is realized by an internal antenna coil within the implantable portion, and an external antenna coil within the external portion. In use, the external antenna coil is positioned so as to be aligned over the location where the internal antenna coil is implanted, allowing such coils to be inductively coupled to each other, thereby allowing data (e.g., the magnitude and polarity of a sensed acoustic signals) and power to be transmitted from the external portion to the implantable portion. Note, in other embodiments of the invention, both the SP 16 and the ICS 21 may be implanted within the patient, either in the same housing or in separate housings. If in the same housing, the link 14 may be realized with a direct wire connection within such housing. If in separate housings, as taught, e.g., in U.S. patent application Ser. No. 09/126,615, filed Jul., 31, 1998, the link 14 may be an inductive link using a coil or a wire loop coupled to the respective parts.

The microphone 18 senses acoustic signals and converts such sensed signals to corresponding electrical signals, and may thus be considered as an acoustic transducer. The electrical signals are sent to the SP 16 over a suitable electrical or other link 24. The SP 16 processes these converted acoustic signals in accordance with a selected speech processing strategy in order to generate appropriate control signals for controlling the ICS 21. Such control signals specify or define the polarity, magnitude, location (which electrode pair receives the stimulation current), and timing (when the stimulation current is applied to the electrode pair) of the stimulation current that is generated by the ICS. Such control signals thus combine to produce a desired spatiotemporal pattern of electrical stimuli in accordance with the desired speech processing strategy. Unlike prior art cochlear implant systems, the present invention advantageously confines such control signals to circuitry within the implantable portion of the system, thereby avoiding the need to continually send or transmit such control signals across a transcutaneous link.

The speech processing strategy is used, inter alia, to condition the magnitude and polarity of the stimulation current applied to the implanted electrodes of the electrode array 48. Such speech processing strategy involves defining a pattern of stimulation waveforms that are to be applied to the electrodes as controlled electrical currents. If multiple electrode pairs exist, as is the case with a multichannel cochlear implant system, then the types of stimulation patterns applied to the multiple channels may be conveniently categorized as: (1) simultaneous stimulation patterns, or (2) non-simultaneous stimulation patterns. Simultaneous stimulation patterns may be "fully" simultaneous or partially simultaneous. A fully simultaneous stimulation pattern is one wherein stimulation currents, either analog or pulsatile, are applied to the electrodes of all of the available channels at the same time. A partially simultaneous stimulation pattern is one wherein stimulation currents, either analog or pulsatile, are applied to the electrodes of two or more channels, but not necessarily all of the channels, at the same time. Examples of each type are given in the referenced patent application, Ser. No. 09/322,712, filed concurrently herewith.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy.

Current pulses applied in pulsatile stimulation patterns are generally biphasic pulses, but may also be multiphasic pulses, applied to the electrodes of each channel. The biphasic/multiphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators of the type used with the present invention, it is common to sample the acoustic signal at a rapid rate, and apply a biphasic stimulation pulse in sequence (i.e., non-simultaneously) to each of the pairs of electrodes of each channel in accordance with a specified pattern and cycle time, with the magnitude of the stimulation current being a function of information contained within the sensed acoustic signal at a given (e.g., the most recent) sample time. An example of such sequential, non-simultaneous stimulation pattern is a continuous interleaved sampler (CIS) strategy.

It is important to recognize that in between the two extremes of fully simultaneous stimulation patterns (wherein analog stimulation currents are continuously applied to all channels, e.g., using the SAS strategy) and non-simultaneous pulsatile patterns (wherein biphasic pules are applied in a specified sequence to all channels without time overlap, e.g., using the CIS strategy), there are a great number of other stimulation patterns that may be formulated. Such other simulation patterns may prove more efficacious for a given patient than either of the SAS or CIS strategies. Thus, an important part of the fitting process is identifying which of several speech processing strategies is most beneficial for a given patient. The present invention assumes that an appropriate speech processing strategy has been identified, or can be easily identified.

Figure 2A:
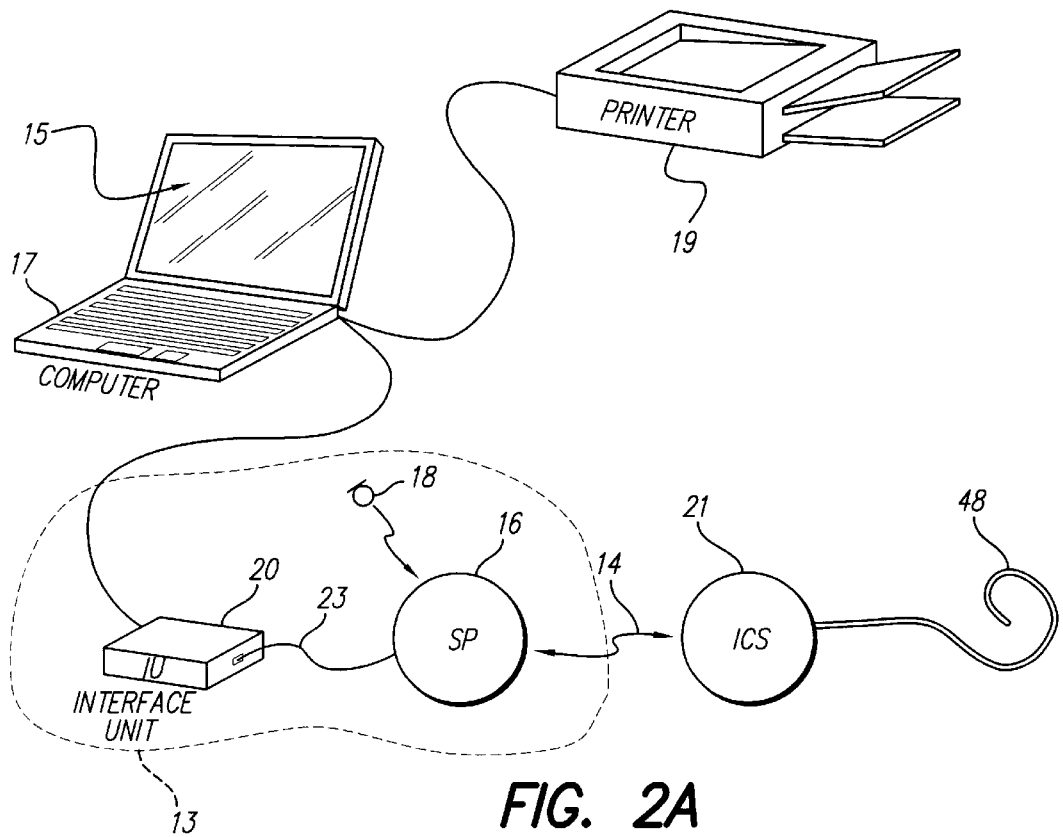
FIG. 2A depicts the elements of a typical fitting system used with the cochlear stimulation system of FIG. 1.

Referring next to FIG. 2A, a block diagram of the basic components used to fit a given patient with a cochlear implant system is shown. While the present invention is not directed to the fitting process, per se, it will nonetheless be helpful to an understanding of the present invention to know how the fitting process occurs, and in particular how a speech processing strategy is selected. As seen in FIG. 2A, the implant system is as shown in FIG. 1, and includes the SP 16 linked to an ICS 21 with electrode array 48. A microphone 18 is also linked to the SP 16 through a suitable communication link 24. A laptop computer 17, or other type of computer, or equivalent device, is coupled to the external portions of the speech processor 16 through an interface unit (IU) 20, or equivalent device. The type of linkage 23 established between the IU 20 and the SP 16 will vary depending upon whether the SP 16 is implanted or not. Any suitable communications link 23 may be used, as is known in the art. It should be noted that for some applications, the IU 20 may be included within the computer 17 (e.g., as a communications interface already present within the computer, e.g., a serial port, or other built-in port, e.g., an IR port).

The computer 17, with or without the IU 20, provides input signals to the SP 16 that simulate acoustical signals sensed by the microphone 18 and/or provide command signals to the SP 16. In some instances, e.g., when testing the patient's threshold levels, the signals generated by the computer 17 replace the signals normally sensed through the microphone 18. In other instances, e.g., when testing the patient's ability to comprehend speech, the signals generated by the computer 17 provide command signals that supplement the signals sensed through the microphone 18.

The laptop computer 17 (or equivalent device) provides a display screen 15 on which selection screens, stimulation templates and other information may be displayed and defined. Such computer 17 thus provides a very simple way for the audiologist or other medical personnel, or even the patient, to easily select and/or specify a particular pattern of stimulation parameters that may be thereafter used by the ICS, even if for just a short testing period, regardless of whether such stimulation pattern is simple or complex. Also shown in FIG. 2A is a printer 19 which may be connected to the computer 17, if desired, in order to allow a record of the selection criteria, stimulation templates and pattern(s) that have been selected and/or specified to be printed.

Figure 2B:
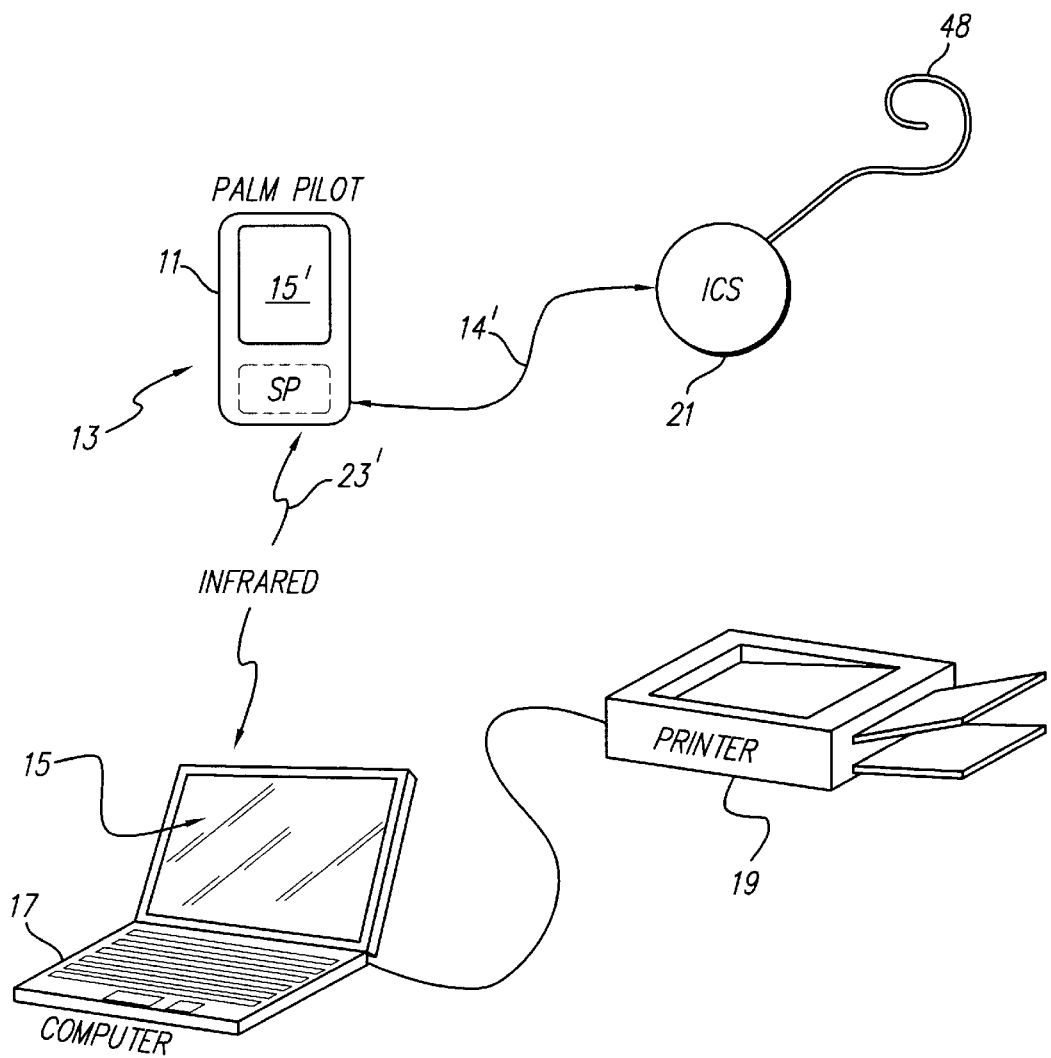
FIG. 2B depicts the elements of an alternate fitting system.

FIG. 2B illustrates an alternative fitting system that may also be used with the invention. In FIG. 2B, the ICS 21 is linked to a speech processor configured or emulated within a palm personal computer (PPC) 11, such as a Palm Pilot, or equivalent processor, commercially available, e.g., from Hewlett Packard. Such PPC 11 includes its own display screen 15' on which some graphical and textual information may be displayed. In use, the PPC 11 is linked, e.g., through an infrared link 23', to another computer, 17, as necessary. Typically, the functions of the SP and related devices are stored in a flashcard (a removable memory card that may be loaded into the PPC 11), thereby enabling the PPC 11 to perform the same functions of those elements encircled by the dotted line 13 in FIG. 2A. The PPC 11 is coupled to the ICS 21 through a suitable data/power communications link 14'.

Figure 3A:
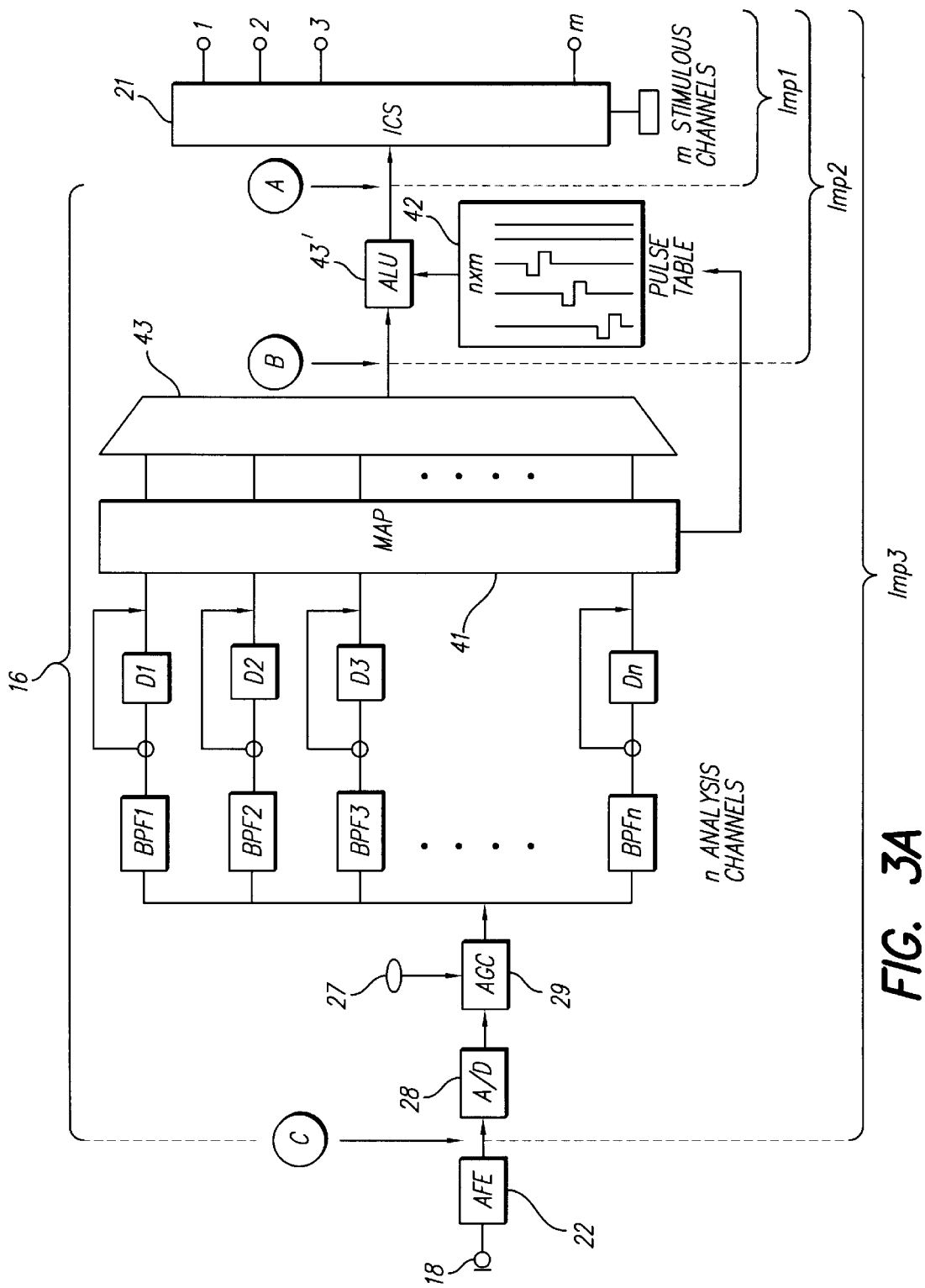
FIG. 3A shows a block diagram that illustrates various allocations of the external and implantable portions of the implant system of FIG. 1.

Turning next to FIG. 3A, a partial functional block diagram of the SP 16 and the ICS 21 of a cochlear implant system is shown. That which is shown in FIG. 3A depicts the functions that are carried out by the SP 16 and the ICS 21. The actual electronic circuitry that is used to carry out these functions is not critical to the present invention., although a representation of circuitry that may be used for this function is described below in conjunction with FIGS. 14–19. It should also be pointed out that the particular functions shown in FIG. 3A are representative of just one type of signal processing strategy that may be employed (which divides the incoming signal into frequency bands, and independently processes each band). Other signal processing strategies could just as easily be used to process the incoming acoustical signal, and the present invention could still be used to provide added flexibility in specifying the stimulation patterns and waveforms that are selected and used with such additional signal processing strategies.

In FIG. 3A, it is seen that a microphone 18 senses acoustical information and converts it to electrical signals. These signals are then amplified in audio front-end (AFE) circuitry 22. The amplified audio signal, at point (C) in FIG. 3A, is then converted to a digital signal by analog-to-digital (A/D) converter 28. The resulting digital signal is then subjected to automatic gain control (AGC) processing using a suitable AGC algorithm 29. The function of the AGC algorithm is to compress the dynamic range of the speech signals so as to provide a more consistent overall level of stimulus to the electrodes, as well as to equalize the level between close and more distant speakers in a given area, e.g., within a room. The AGC algorithm 29 operates by measuring the volume level of the signal and using the measurement result to control a variable gain stage. The gain is controlled by two loops, where the lowest control voltage of the two loops is selected. One loop performs syllabic compression by responding slowly to sounds above about 55 dB SPL, the second loop performs as a compression amplifier by responding quickly to sounds over about 67 dB SPL. [For a discussion of sound levels, and a definition of dB SPL, see "Moore, Brian C. J., "An Introduction to the Psychology of Hearing", Fourth Edition, pp. 9–12 (Academic Press 1997).] A sensitivity control 27 is coupled to the AGC circuit 29. The sensitivity control 27 may be either a dial or remote control, preferably a remote control, and may vary either front-end gain and/or AGC parameters.

As further seen in FIG. 3A, after signal processing by the AGC algorithm 29, the signal is processed in one of a multiplicity of digital signal processing channels. For example, eight separate analysis channels may be used, each responding to a different frequency content of the sensed acoustical signal. In other words, the incoming signal is divided into a multiplicity of n frequency channels, as defined by a bank of respective bandpass or other filters BPF1, BPF2, BPF3, . . . BPFn. The lowest frequency filter may be a lowpass filter, and the highest frequency filter may be a high-pass filter.

Figure 3B:
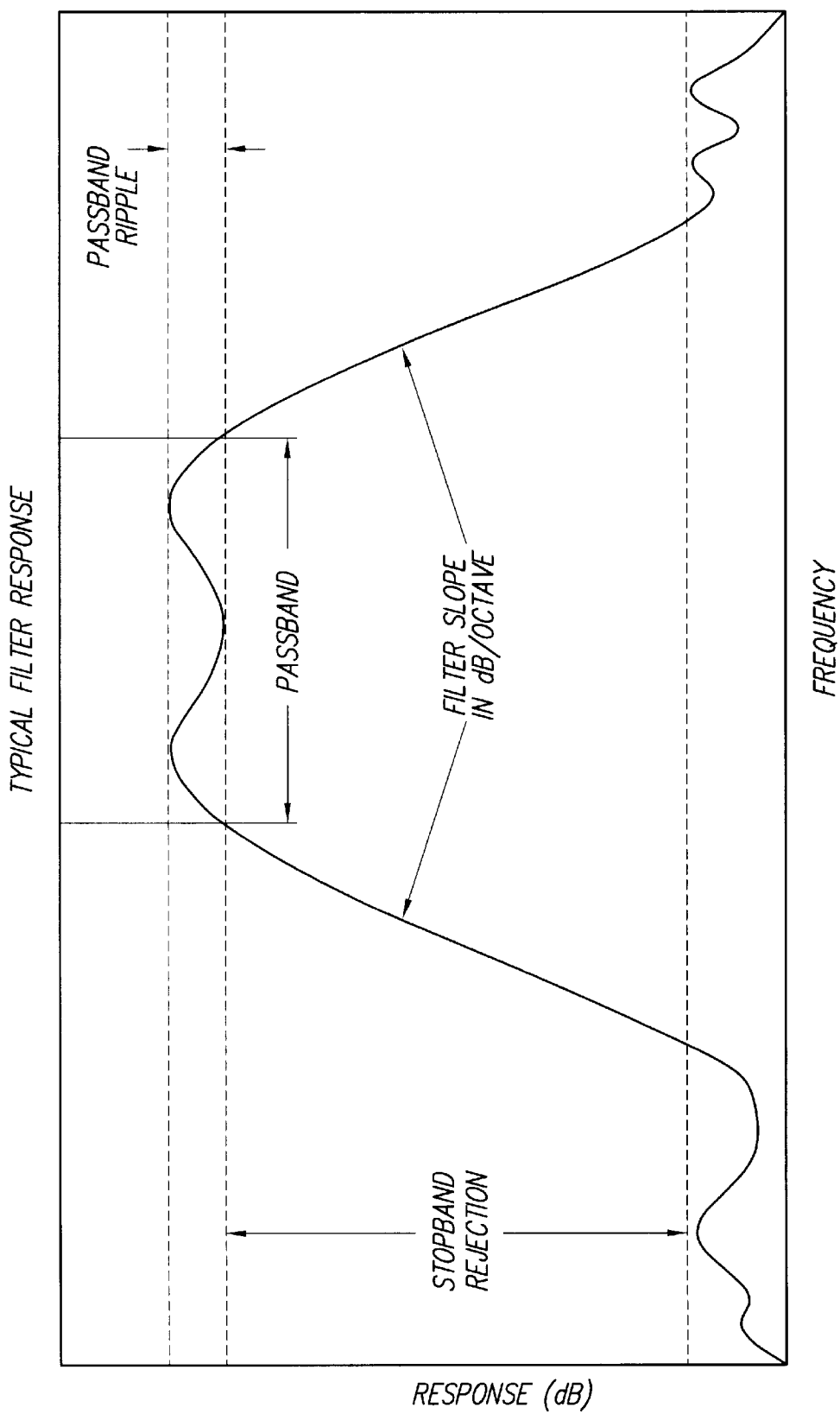
FIG. 3B depicts a typical filter response of the bandpass filter used in most of the channels of the speech processor of a multichannel cochlear stimulation system.

Typical characteristics of the passband filters are illustrated as shown in FIG. 3B. All of the filters have a maximum pass band ripple of 3 dB, a stop band rejection of at least 50 dB, a filter slope of 39 dB/octave, and internal filter noise of at least 50 dB below the signal.

The gain of each filter is equal for all channels by default, but may be modified by a user in ±10 dB increments, if desired. Representative frequency maps for the filters BPF1, BPF2, BPF3, . . . BPFn are shown in FIG. 3C. As seen in FIG. 3C, a slightly different frequency map is used by default for SAS than is used for CIS. Still other frequency maps may be readily used and new ones defined, as required, for whatever type of speech processing strategy is selected.

Returning back to FIG. 3A, it is seen that after the received signal is filtered, it passes through a respective detection stage D1, D2, D3., . . . Dn. As its name implies, the detection stage involves some type of energy detection circuit, which may be realized, e.g., through a rectification circuit followed by an integrator circuit. The rectification may be either full-wave, or half-wave. Full-wave rectification provides a more spectrally pure signal than half-wave, but the spiral ganglion nerve cells, under certain conditions, seem to perform a type of half-wave rectification. Other types of energy-detection stages could also be used, e.g., a simple envelope detector. All that is required is an appropriate energy-content determination be made of the signal that passes through the bandpass filter. Most continuous analog speech processing strategies bypass the detection stage.

Figure 3D:
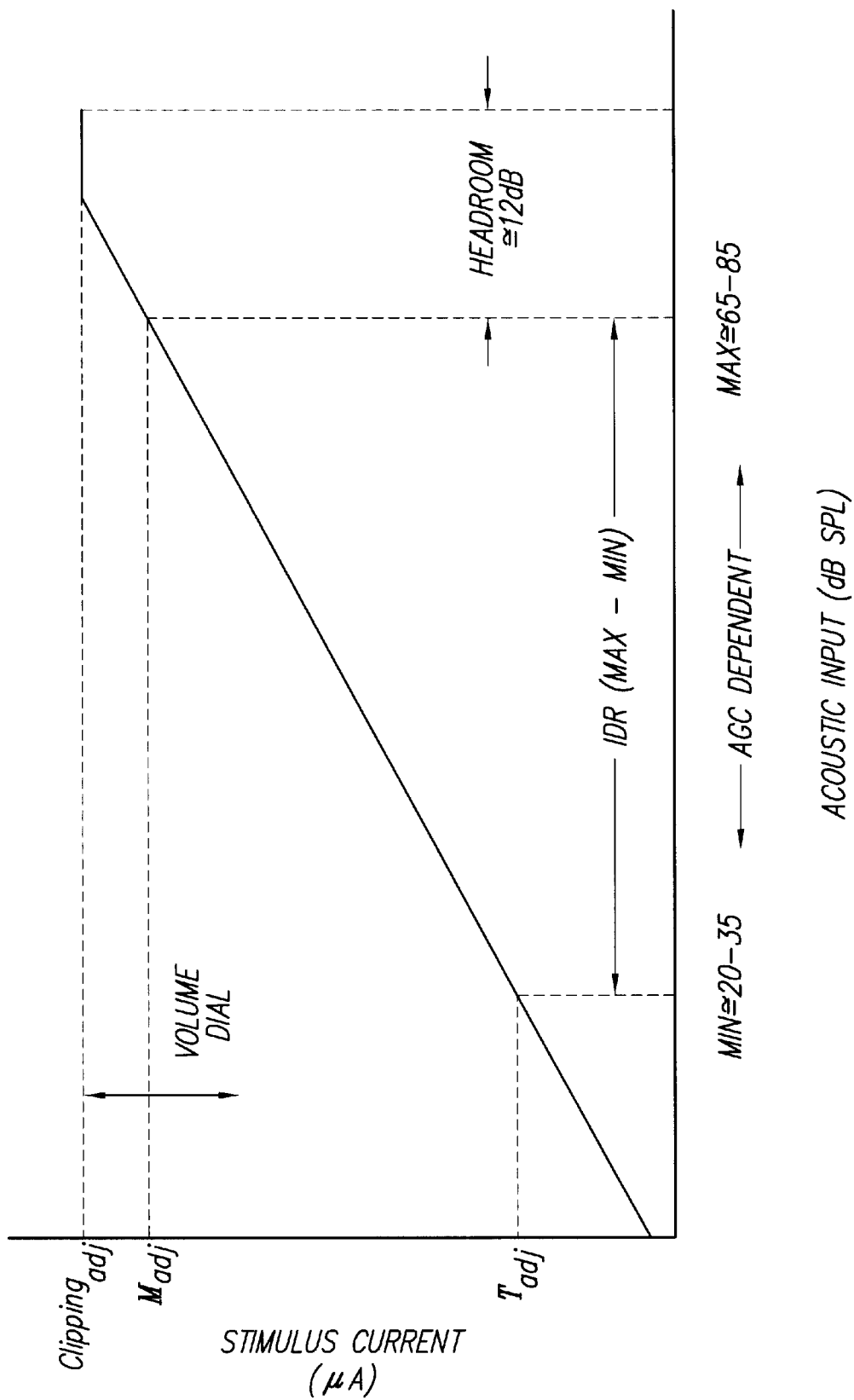
FIG. 3D shows a preferred channel compression transfer function used within each channel of the speech processor of a multichannel cochlear stimulation system.

After energy detection, or bypassing of such, the signal from each of the n analysis channels is forwarded to a mapping stage 41. The mapping stage performs additional processing of the signal, as required. More particularly, the mapping stage 41 typically splits the signal into two paths. In a first path, the signal is compared to a reference threshold signal, and if the threshold is exceeded, then that information is forwarded to a pulse table 42 for use with certain pulsatile speech processing strategies. The function of the pulse table 42 is explained more fully below. In a second path, the additional processing includes signal compression, pursuant to an appropriate signal compression algorithm, as taught in applicant's copending patent application, "Strategy Selector for Multichannel Cochlear Prosthesis", previously referenced. A suitable compression algorithm is illustrated in FIG. 3D. The compressed signal is then mapped between the patient's T and M levels, and/or between other set levels, as explained in the referenced patent application. A volume function is also implemented in conjunction with the compression and mapping function.

After compression and mapping in the mapping stage 41, the n analysis channels are serialized through a multiplexer 43, or equivalent circuitry, into one serial data channel, present at point (B) in FIG. 3A. As the data stream passes through the serial data channel, it is acted upon by data from the pulse table 42 in an arithmetic logic unit (ALU) 43'. As explained more fully below, the operation performed by the ALU 43' is usually a simple multiplication, at least with respect to pulsatile strategies. The result of this multiplication is a "product" signal, present at point (A) in FIG. 3A. This product signal represents a control signal that is then passed through to the ICS 21, where it is used to control the precise stimulation currents that are delivered through each of the m stimulous channels. The manner in which the pulse table 42 produces this useful result is explained more fully below.

Note that the pulse table 42 is effectively an n×m table, having n columns and m rows, or the equivalent. As the serial data stream passes through point (B), it effectively represents, in appropriate time increments, an n×1 matrix, or data word. As this n×1 matrix, or word, is acted upon in the ALU 43' by the n×m table, the result is an m×1 data matrix, or data word, for each of the n columns of the table. These n m×1 words pass through point (A) in the data path and are applied, one word at a time, to each of the m stimulous channels in order to control the stimulous current at each of the m stimulous channels. In this manner, the complex spatiotemporal current stimulation patterns associated with the selected speech processing strategy is applied to the auditory nerve through the patient's cochlea.

In the manner described above, each of the n analysis channels may be mapped to one or more stimulous channels. That is, it is seen that the system as configured in FIG. 3A provides a multiplicity of channels, n, wherein the incoming signal is analyzed. The information contained in these n "analysis channels" is then appropriately processed, compressed and mapped in order to control the actual stimulus patterns that will be applied to the patient by the ICS 21 and its associated electrode array 48. The electrode array 48 includes a multiplicity of electrode contacts, connected through appropriate conductors, to respective current generators, or pulse generators, within the ICS. Through these multiplicity of electrode contacts, a multiplicity of stimulus channels, e.g., m stimulus channels, exist through which individual electrical stimuli may be applied at m different stimulation sites within the patient's cochlea.

Figure 3E:
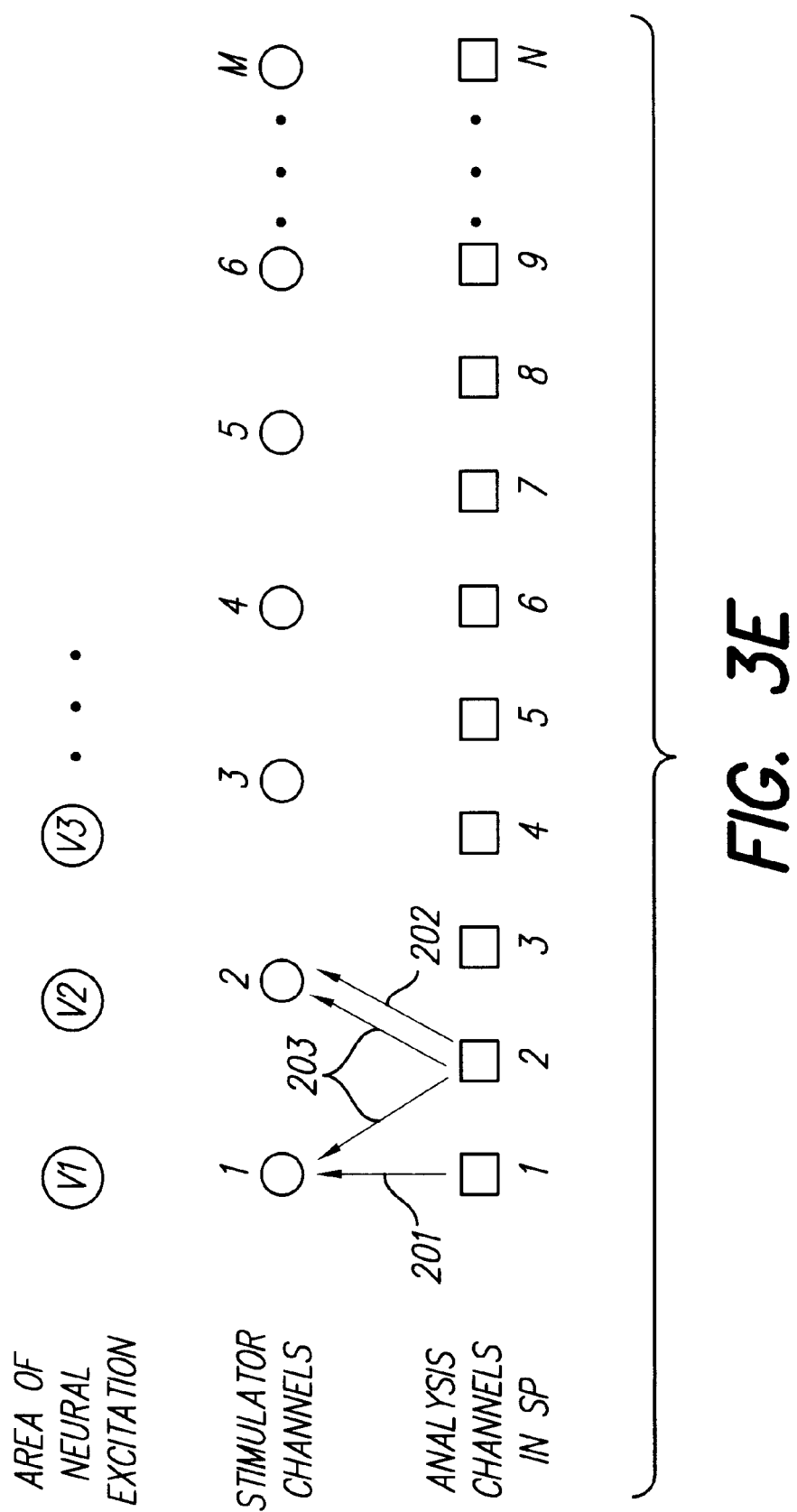
FIG. 3E shows how multiple analysis channels in the speech processor may be mapped with multiple stimulator channels in the cochlear stimulator in order to provide multiple neural excitation sites.

The above-described concept of having n analysis channels controlling m stimulation channels is schematically illustrated in FIG. 3E. While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Rather, in some instances, a different mapping scheme may prove beneficial to the patient. For example, as depicted in FIG. 3E. assume that n is not equal to m (n, for example, could be at least 20 or as high as 32, while m may be no greater than sixteen, e.g., 8 to 16). The signal resulting from analysis in the first analysis channel may be mapped to the first stimulation channel via a first map link 201 (FIG. 3E), resulting in a first stimulation site (or first area of neural excitation) V1. Similarly, the signal resulting from analysis in the second analysis channel of the SP may be mapped to the second stimulation channel via a second map link 202, resulting in a second stimulation site V3. Also, as seen in FIG. 3E, the signal resulting from analysis in the second analysis channel may be jointly mapped to the first and second stimulation channels via a joint map link 203. This joint link 203 would result in a stimulation site V2 that is somewhere in between the V1 and V3 stimulation sites. The V2 site is sometimes referred to as a virtual stimulation site. Advantageously, this possibility of using different mapping schemes between n SP analysis channels and m ICS stimulation channels to thereby produce a large number of virtual and other stimulation sites provides a great deal of flexibility with respect to positioning the neural excitation areas in a location that proves most beneficial to the patient.

With reference again to FIG. 3A, it should be noted that the speech processing circuitry 16 generally includes all of the circuitry from point (C) to point (A). In prior art cochlear implant systems, the entire SP circuitry was housed in a speech processor that was part of the external (or non-implanted) portion of the system. That is, in such prior art systems, only the ICS 21, and its associated electrode array, were implanted, as indicated by the bracket labeled "Imp1" (for "Implant-1"). This means that in such prior art systems, the signal passing through the serial data stream at point (A) is also the signal that must pass through the transcutaneous communication link from the external unit to the implanted unit. Because such signal contains all of the defining control data for the selected speech processing strategy, for all m stimulation channels, it therefore has a fairly high data rate associated therewith. As a result of such high data rate, either the system operation must be slowed down, which is generally not desirable, or the bandwidth of the link must be increased, which is also not desirable because the operating power increases.

In contrast to prior art systems, the present invention advantageously puts at least a portion of the speech processor 16 within the implanted portion of the system. For example, the present invention places the Pulse Table 42 and ALU 43' inside of the implanted portion, as indicated by the bracket labeled "Imp2" in FIG. 3A. Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained.

It is contemplated that future generations of the implant system will incorporate more and more of the speech processor 16 within the implanted portion of the system. For example, a fully implanted speech processor 16 would incorporate all of the SP in the implanted portion, as indicated by the bracket labeled Imp3 in FIG. 3A. Such a fully implanted speech processor would offer the advantage that the data input into the system, i.e., the data stream that passes through point (C), would need only have rate commensurate with the input acoustic signal.

Figure 4:
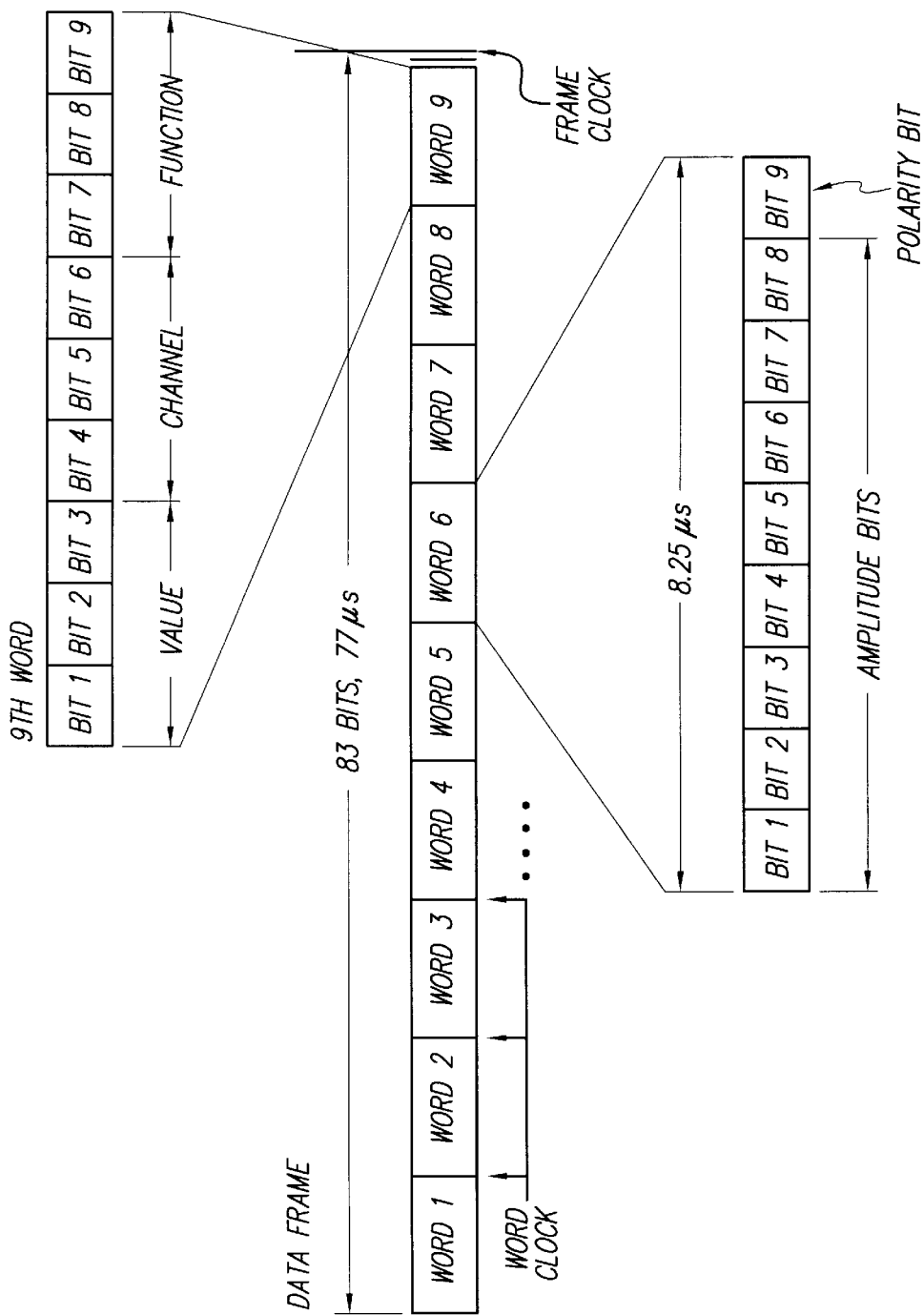
FIG. 4 shows one format for a data frame that may be used with a cochlear implant system.

Next, to further explain how the pulse template or table 42 (FIG. 3A) defines a particular speech processing strategy, reference is made to FIG. 4. Shown in FIG. 4 is the makeup of a typical data frame that may be used with a representative cochlear stimulation system, e.g., of the type described in U.S. Pat. No. 5,603,726, incorporated herein by reference,. It is noted that the cochlear stimulator described in the 726 patent is the type commonly used in the prior art, i.e., one wherein the speech processor is totally contained within the external portion. Nonetheless, it will be instructive to first understand how a pulse table 42 functions when used with such a prior art system, before explaining its use within an implanted system. The use of such a data frame as shown in FIG. 4 is necessary due to the fact that multiple channels of stimulation information are needed by the ICS 21, yet there is only a single telecommunications channel 14 (FIGS. 1 or 2) through which information may be transferred to the ICS. In other words, use of the data frame shown in FIG. 4 allows parallel data channels to be temporarily reformatted into a serial data channel to facilitate transmission of the information to the ICS. Such serial transmission is needed when the transmission is through a single serial data channel realized via a transcutaneous or other link from an external speech processor to an implanted cochlear stimulator. As FIG. 3A above illustrates, even when the speech processor is implanted, e.g., in a separate case or housing than is the cochlear stimulator, or when portions of the speech processor are implanted, a serial link may still be needed or utilized. Thus, it is seen that it may be necessary to use a serial data channel somewhere in the system even though parallel data channels are used to process sensed data and to stimulate the patient.

As seen in FIG. 4, the representative data frame is made up of 9 nine-bit words, plus a parity bit and an end-of-frame bit, or a total of 83 bits. The clock rate is such that the overall duration of a complete data frame is about 77 $\mu$sec.

The first eight words in the data frame are data words, and each contains amplitude bits (the first eight bits) and a polarity bit. Each data word corresponds to the stimulation information for a given channel. The last word of the data frame, or the ninth word, is a control word. Such word is used to control and/or set various functions within the ICS, e.g., the electrode configuration (bipolar or monopolar) that the ICS will use. The general format of the control word is also shown in FIG. 4.

Figure 5:
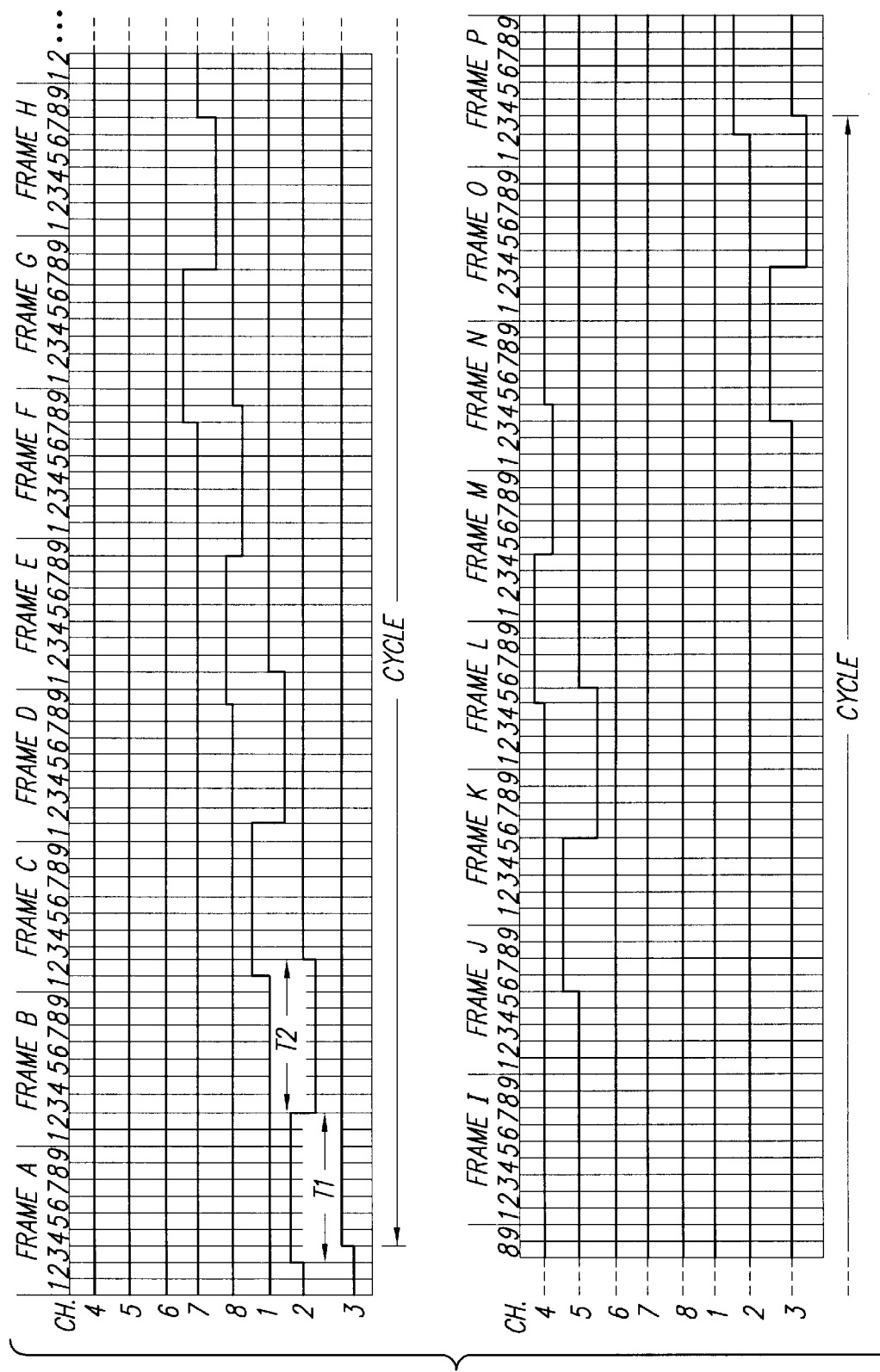
FIG. 5 illustrates how multiple data frames may be used with the system of FIG. 3A in order to achieve a desired stimulation pattern that repeats itself in cycles.

FIG. 5 illustrates bow multiple data frames may be used to achieve a desired stimulation pattern that repeats itself in cycles. The particular stimulation pattern shown in FIG. 5 approximates a simple CIS strategy because, for the most part, only one electrode pair (channel) is stimulated with a biphasic pulse at any given time. To understand FIG. 5, it is important to recognize that the data word in each data frame specifies the amplitude and polarity for the stimulation current of the corresponding channel. Such amplitude and polarity, once set by a data words, remains unchanged until a new data word, in a new data frame, is received to make a change. Thus, to produce a biphasic stimulation pulse, it is necessary to specify an amplitude and polarity for the channel in a first data frame, specify the amplitude and opposite polarity in a second data frame, and finally, specify a zero amplitude in a third data frame. If a CIS strategy is employed, as approximated in FIG. 5, then each channel is maintained at a zero amplitude until such time in the cycle as it is that channel's turn to be stimulated in the specified sequence.

As shown in FIG. 5, for example, the specified sequence comprises (starting at the left of the figure) stimulating the electrode pair of channel 2, then channel 1, then channel 8, then channel 7, then channel 6, then channel 5, then channel 4, and then channel 3. In a first data frame, Frame A, a positive stimulation current is applied to the electrodes of channel 2. The magnitude of this stimulation current is a function of the sensed acoustic signal falling within the frequency band corresponding to channel 2, and as otherwise processed by the speech processor 16. Note that during data Frame A, not only is channel 2 stimulated, but the stimulation current already present in channel 3 is turned off. This process continues, as shown, with each phase of the biphasic pulse lasting for a time equal to the length of a data frame, and with the complete stimulation cycle requiring 16 data frames.

Still referring to FIG. 5, the numbers 1–9 included for each data frame correspond to the nine data words present in each data frame. Thus, when a change is included in the first word of the data frame, such change occurs early in the data frame, whereas a change that occurs in the last word of the data frame, occurs late in the data frame. Given this restriction, one aspect of the present invention relates to mapping the particular electrode pair associated with the words of the data frame so that the electrode pair in contact with the basal end of the cochlea, which receives high frequency information and thus has the most information capacity, is mapped to the first word in the data frame. The apex of the cochlea, which receives low frequency information and thus has the least information capacity, is mapped to the last word in the data frame. This mapping scheme, in combination with sending partial frames (as described below) advantageously permits a two-to-three times faster update rate to occur at the base of the cochlea than has heretofore been possible.

It should be noted that the stimulation pattern depicted in FIG. 5 represents a simple (non-complex) stimulation pattern. The present invention advantageously utilizes simple and easy-to-define stimulation templates that permit the ICS to generate much more complex stimulation patterns without having to significantly alter the basic operating programs of the speech processor 16, and without having to alter the circuitry of the ICS 12. In fact, the stimulation templates of the present invention may advantageously be used with any type of stimulation system that provides an implanted stimulator that follows the commands of an external processor in a master/slave relationship. That is, so long as the individual channels (or specific tissue stimulation locations as defined by a selected electrode pair) of the implanted stimulator can be set to a specific stimulation current value (including a zero value) as controlled by the processor, and remain at those values until reset by the processor to a new stimulation current value, then the present invention can advantageously be used by such system.

Figure 6:
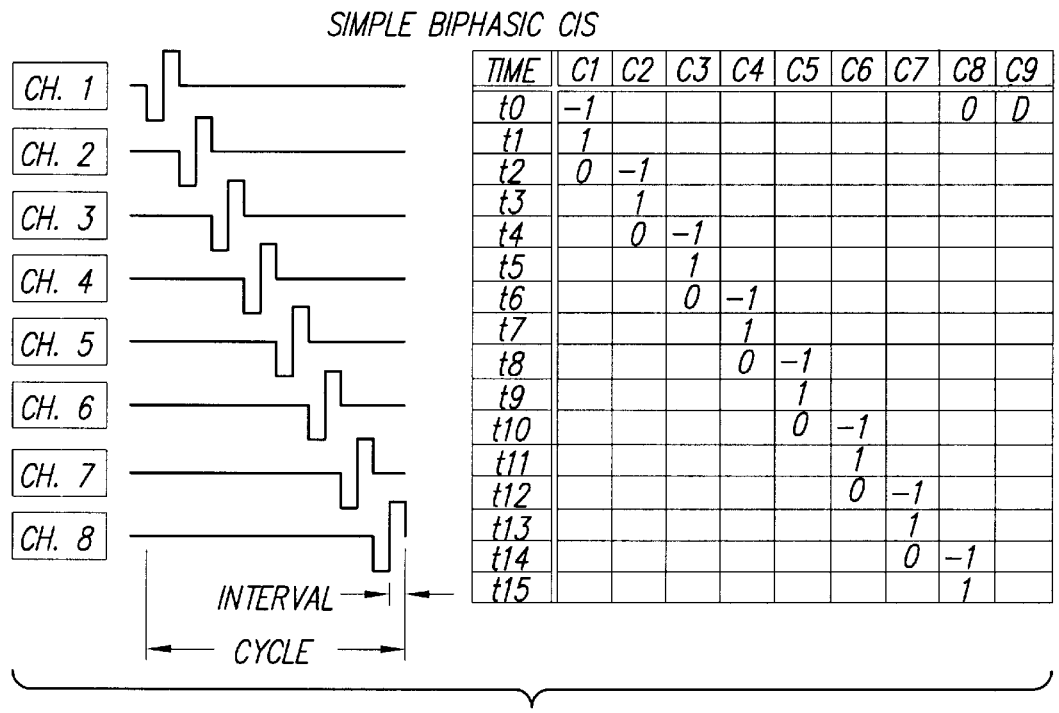
FIG. 6 illustrates a simple biphasic CIS stimulation template for use with the invention that provides a CIS stimulation pattern for an eight-channel stimulator device.

To illustrate, FIG. 6 shows one representation of a simple biphasic CIS stimulation template for use with the present invention that provides a CIS stimulation pattern for an eight-channel stimulator device. The template is in the form of a stimulation table, shown on the right side of FIG. 6, which table may be stored in the memory of the processor 16. The biphasic stimulation currents that result from using such template are represented on the left side of FIG. 6. Note that the stimulation table or template comprises rows and columns. Each row represents an increment of time, which increment of time may be set to an appropriate value for the particular application. For the table shown in FIG. 6, it is presumed that all of the increments of time, t0–t15, are equal increments of time. However, as will be demonstrated by other possible templates shown below, the time increments need not be equal, but can be specified to any appropriate value.

Each column of the template table shown in FIG. 6 represents a channel, or stimulation location, Thus, referring to FIG. 6, it is seen that each cell (i.e., each intersection of a row and column) of the template table defines a particular stimulation current that is to be applied to a specific location (the channel, or column) at a particular time (the specified time, or row). The combination of all the cells of the template table thus defines a particular temporospatial stimulation pattern, or a particular cycle of stimulation waveforms, that are to be applied to specific stimulation locations at specific times within the stimulation cycle.

The numerical values inserted into the cells of the template table represent weighting factors which are to be used to modify the amplitude of the processed signals (derived from the incoming acoustical signal). (It should be noted that data values other than numeric values could also be used for this purpose, e.g., a hexadecimal or other alphanumeric value could be inserted into the cells of the template table as a code.) A null value (blank) table cell indicates that a zero stimulus waveform has been in effect and should continue in effect for the channel and time specified by the column/row of the template. Typically, the weighting factor will simply be used as a multiplication factor. Thus, if the template table contains a "+1" in a given cell, then that means the processed signal for that channel is to be multiplied by a "+1", with the product of such multiplication serving to define or specify the amplitude of the desired stimulation current to be applied to the electrode pair of the channel at the indicated time increment. An explicit zero, or "0", denotes the time at which a previously non-zero channel is first set to zero output.

It is to be emphasized that the rows and columns of the template table can be reversed and the template table will still serve its intended function of clearly and easily defining a particular stimulation pattern, even a complex stimulation pattern (as is demonstrated below) for use by an ICS or equivalent stimulator device. That is to say, each column of the table may represent an increment of time, and each row of the table may represent a channel, or stimulation location. Further, it is to be emphasized that any circuitry equivalent to a table, having rows and columns, may likewise be used, e.g., a multi-bit register that is temporarily loaded by a clock signal with column (or row) data as stored in a memory element, e.g., a random access memory (RAM).

Referring to FIG. 6, it is seen that at time t0, the first channel, C1, has a value "−1" inserted therein. All other cells in the table at time t0 are blank (null values), except for C8 (which has a "0" inserted therein), and C9 (which corresponds to the control column or word and which has a "D" inserted therein). The "−1" in the cell corresponding to channel C1 at time t0 means that whatever magnitude is present in the channel 1 signal at time to will be multiplied by a "−1". The "0" simply means that channel C8 is to be reset back to zero (null) at time t0. The "D" in channel C9 (which is the control word channel) means that the 9th word command is to be set to its default value. At time t1, the weighting factor for channel C1 changes to a "+1". At time t2, the weighting factor for channel C1 is set to "0", and the weighting factor for channel C2 is set to "−1". The timing associated with the actual waveforms for the stimulation currents thus take the form as illustrated on the left side of FIG. 6.

Figure 7:
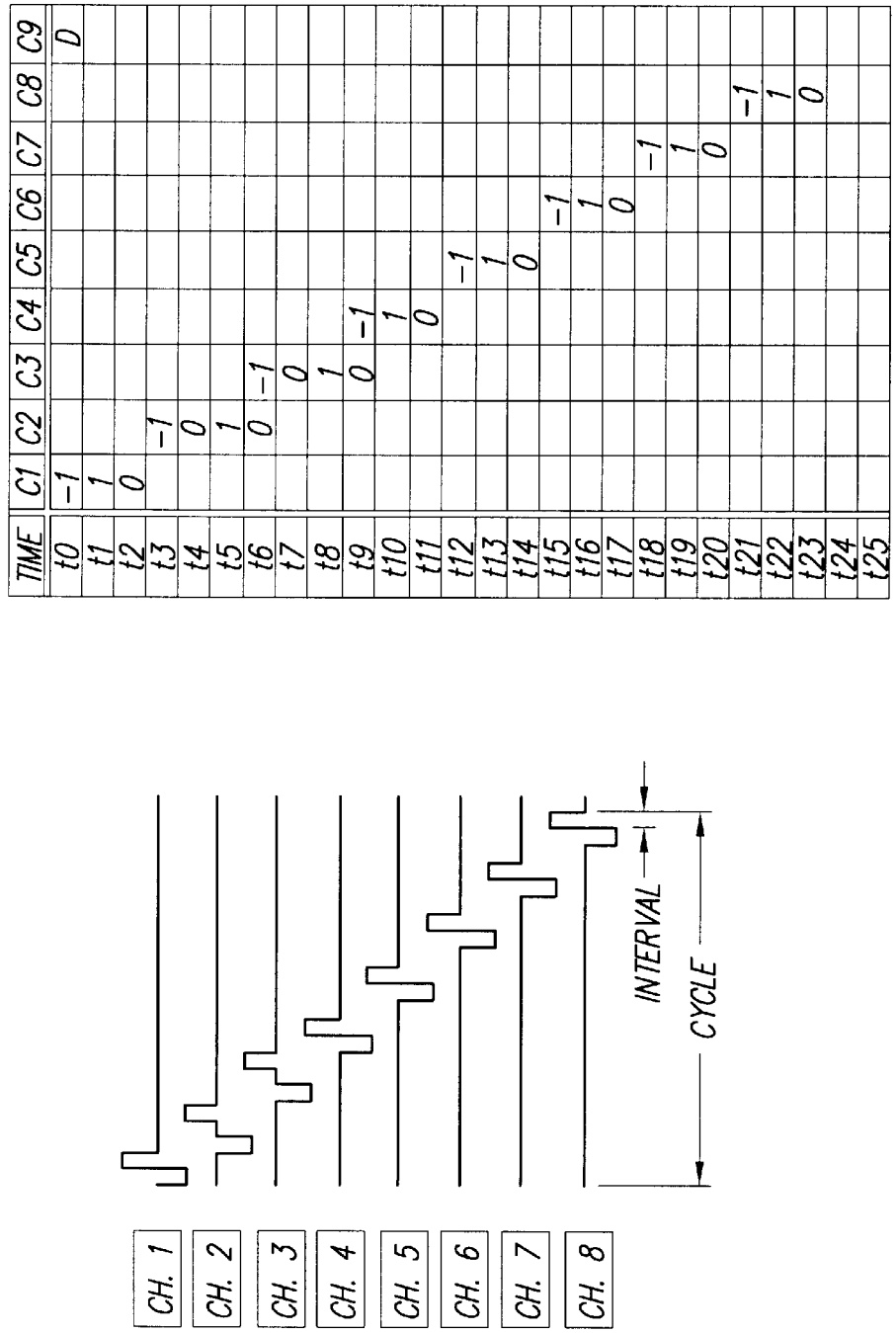
FIG. 7 shows the stimulation template for a somewhat more complex biphasic stimulation pattern that includes time delays between phases and channels.

FIG. 7 shows the stimulation template table as in FIG. 6, but for a somewhat more complex biphasic stimulation pattern that includes time delays between phases and channels.

Figure 8:
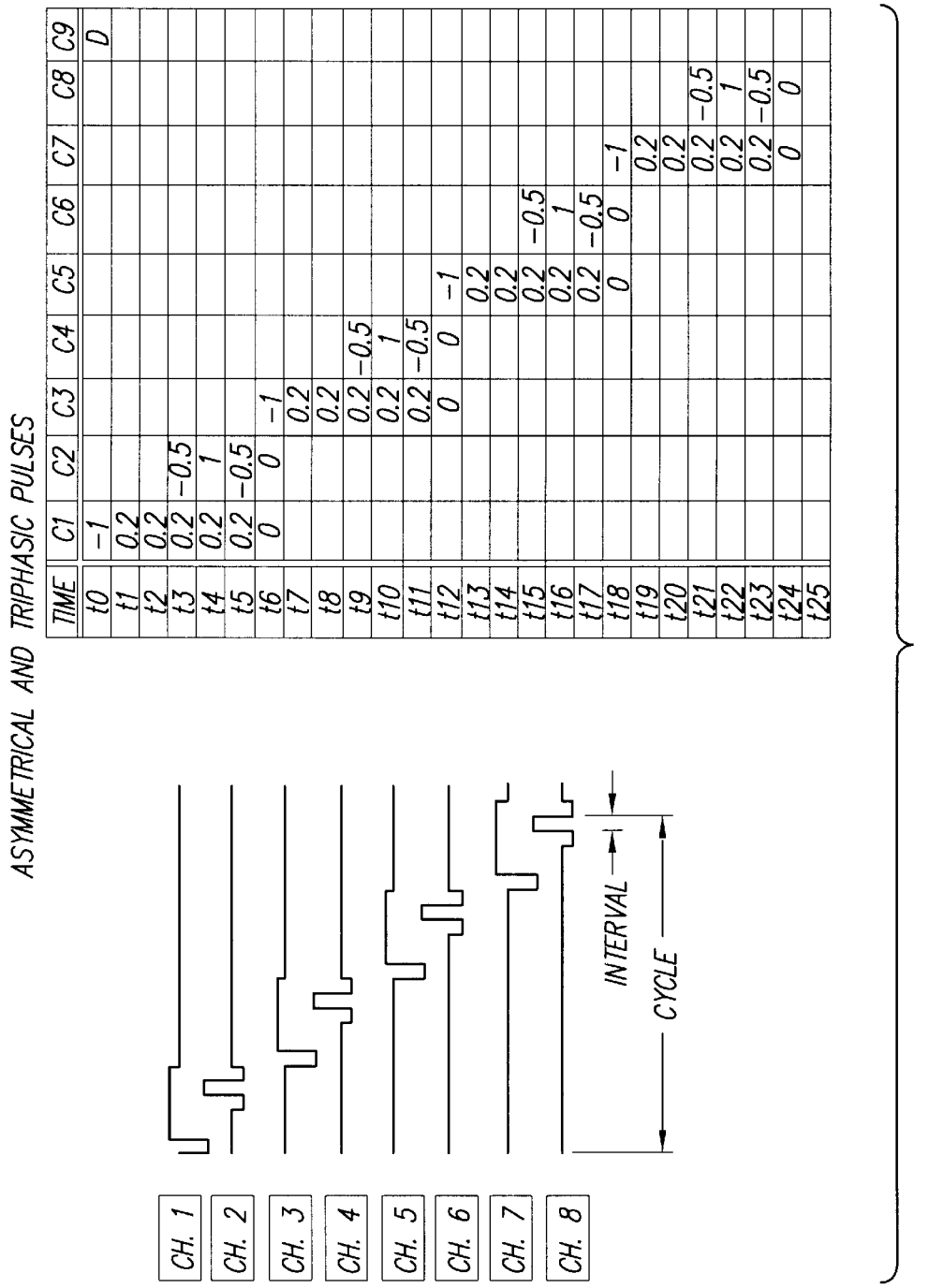
FIG. 8 depicts the stimulation template for a much more complex stimulation pattern that includes asymmetrical and triphasic pulses.

Similarly, FIG. 8 depicts the stimulation template table for a much more complex stimulation pattern that includes asymmetrical and triphasic pulses. Note that the weighting factors are selected so that the sum of the positive factors always equals the sum of the negative factors, thereby assuring a charge balance in the stimulation waveform that is ultimately generated.

Figure 9:
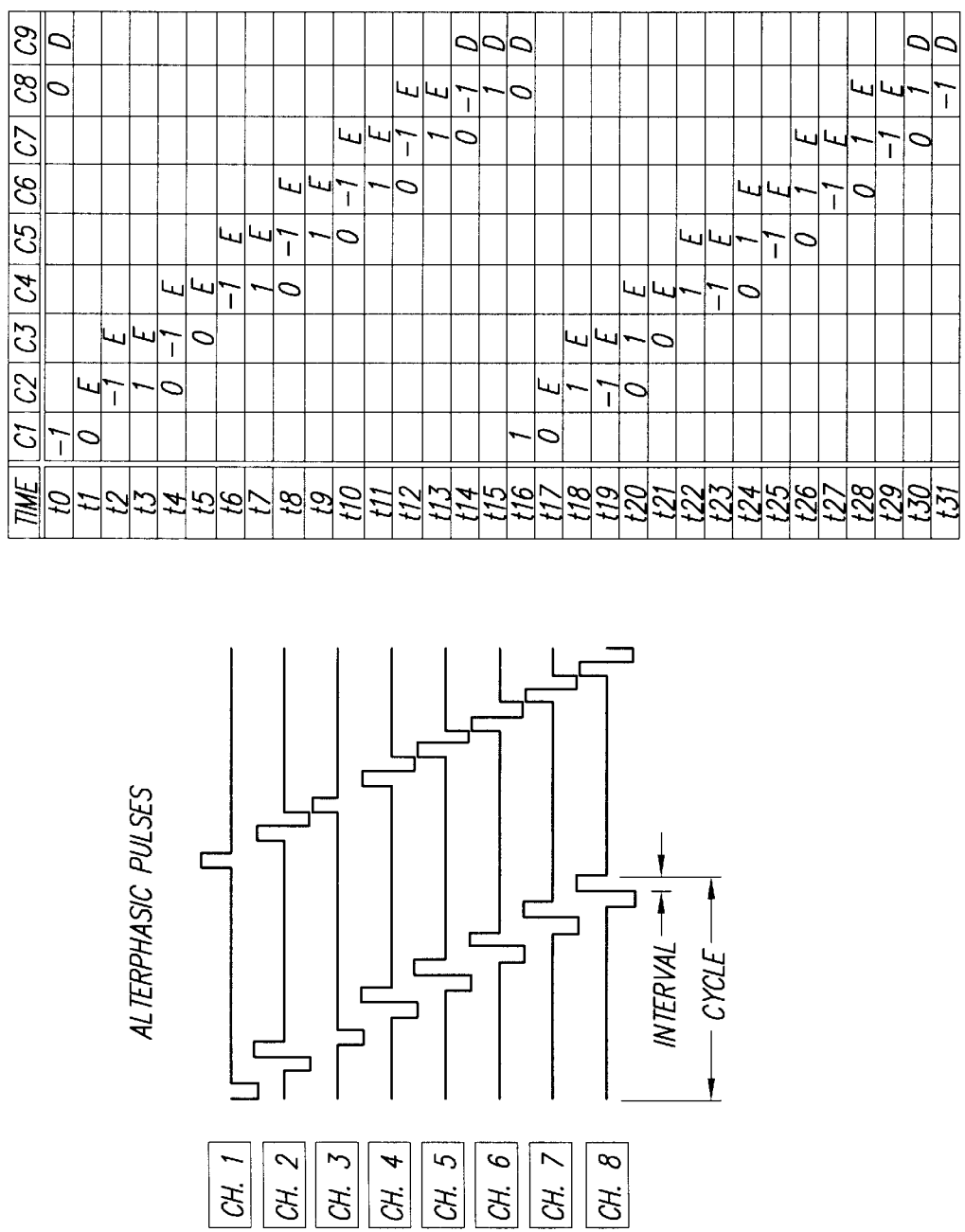
FIG. 9 shows the stimulation template for a stimulation pattern that includes "alterphasic" pulses in which charge balance is achieved by two monophasic pulses with opposite polarity presented at different times in the cycle.

FIG. 9 shows the stimulation template table for a stimulation pattern that includes alterphasic pulses. An alterphasic pulse is a pulse as shown for channel C1 and channel C3—a pulse of one polarity followed in the next cycle by a pulse of the opposite polarity.

FIG. 9 also illustrates another feature in which a special code "E" is used to indicate that the remainder of the row contains no changes of output state. This permits the microprocessor to save computation time to conserve power or facilitate other concurrent operations.

It is thus seen that the numbers or other alphanumeric codes written into the cells of the template table allow diverse and complex patterns to be specified. Such patterns can easily be produced in real-time by a microprocessor that is programmed to read the cells of the table as input data. Because the possible output states are entirely specified by the template table, there is no possibility of unexpected delays occurring during real-time execution of the program. This is a critical feature, because the charge-balance of the waveforms produced by each current source depends on computing the weighting coefficients or factors such that the sum of the products of each weighting coefficient times the respective time interval for that row of the template table adds to zero for all weighting coefficients in each column. That is, the amount of time that each of the current sources stays in any particular output state must be predictable and reproducible from cycle to cycle.

As should be evident from an examination of the template tables presented above (and below), the length of a given row represents the length or duration of a data frame. The length of a data frame, in turn, specifies the minimum pulse width that may be included within a biphasic stimulation pulse (or other stimulation waveform). One advantage of the present invention is that means are included within the speech processor for shortening selected rows of the table in order to reduce the number of blank cells in a given row. Such shortening, in turn, thereby reduces the minimum pulse width that may be utilized in the stimulus waveform, thereby allowing a more rapid rate of pulses in the stimulus waveform. When such pulses are applied to the basal electrodes of the cochlea, it is thus possible to convey more information to the cochlea than has previously been possible.

Figure 10:
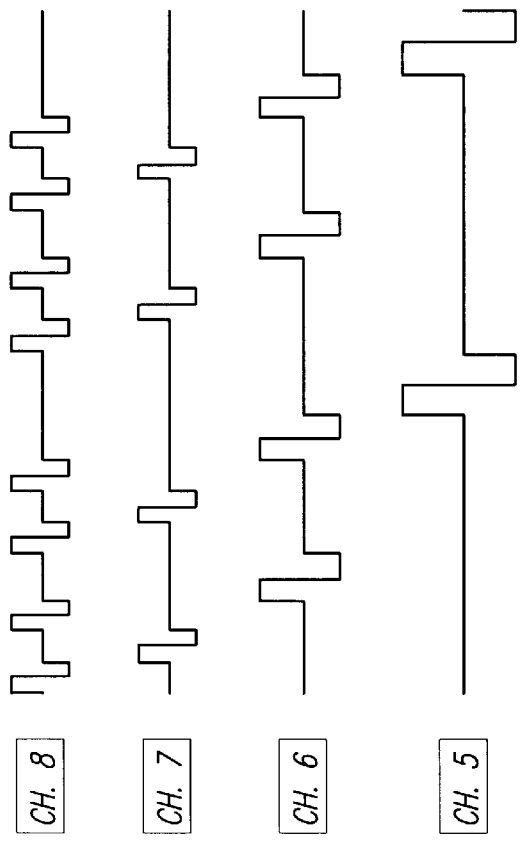
FIG. 10 illustrates the stimulation template for a stimulation pattern that includes more frequent narrow biphasic stimulation pulses in some channels, and less frequent wider biphasic stimulation pulses in other channels.

Referring next to FIG. 10, a stimulation template is illustrated for a stimulation pattern that includes more frequent narrow biphasic stimulation pulses in some channels, and less frequent wider biphasic stimulation pulses in other channels. Also note that only four of the stimulation channels are used in the pattern shown in FIG. 10: channels C5, C6, C7 and C8. In use, the C8 channel, which has the most frequent pulses applied thereto, preferably corresponds to the electrode pair placed at the basal end of the cochlea. This is because, as previously indicated, the basal end of the cochlea receives high frequency information and thus has the most information capacity. The time intervals used in FIG. 10 may be much shorter than the time intervals used, e.g., in the templates of FIGS. 6–9, so that the overall cycle length in FIG. 10 need not be any longer than, and may even be shorter than, the cycle lengths in FIGS. 6–9.

Figure 11:
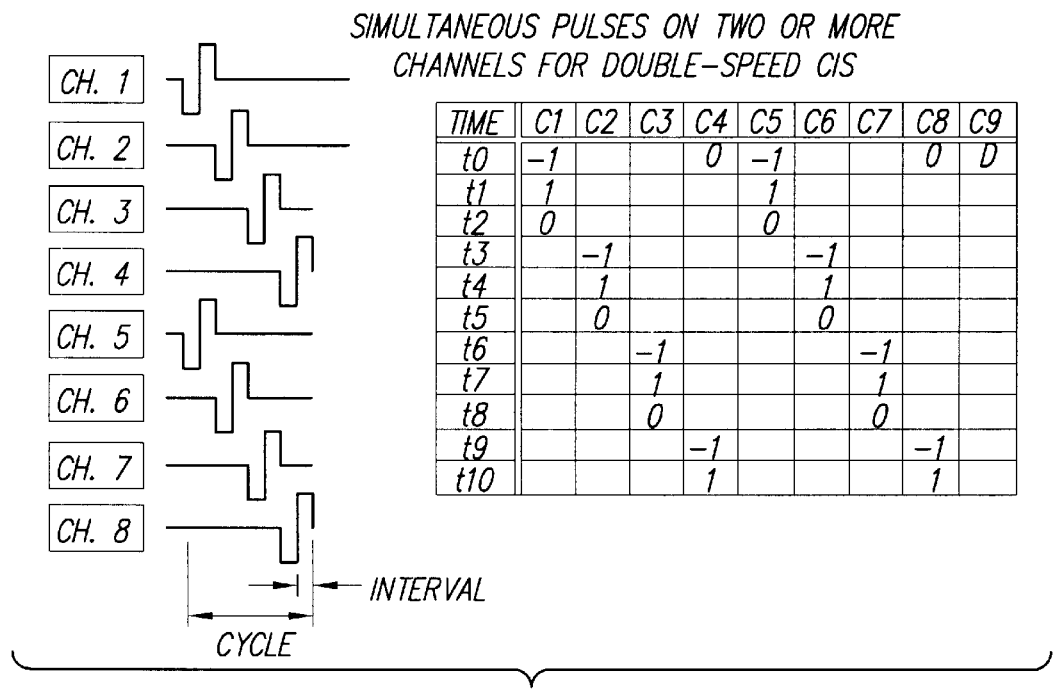
FIG. 11 depicts the stimulation template for a stimulation pattern that provides simultaneous or substantially overlapping biphasic pulses on two or more channels.

FIG. 11 depicts a stimulation template for a stimulation pattern that provides simultaneous biphasic pulses on two or more channels. Such a pattern allows the overall cycle length to be decreased significantly. The stimulation pattern shown in FIG. 11 is of particular interest because of the delivery of pulses more or less simultaneously at two or more different sites. Note that the CIS strategy is designed to minimize electrotonic interactions between the stimulus currents applied at adjacent sites by delivering brief stimulation pulses in a sequential, interleaved, i.e. non-overlapping manner. It is also desirable, however, to complete the stimulation of all sites in as short a cycle time as possible, permitting the information from the acoustic signal to be sampled and presented at a relatively high rate. In order to sequence through a large number of stimulation sites at a relatively rapid rate, the length of time available to deliver each individual stimulation pulse must be made very short. The efficacy of a given stimulus pulse in activating neurons depends on the product of the magnitude and duration of the current, i.e. the total charge delivered in each phase of the waveform. In order to activate neurons with a very brief current pulse, the magnitude of the current must be made proportionately higher. Because the electrode contacts and surrounding tissue represent a significant impedance to the flow of electrical current, the applied voltage and dissipated power will also be much higher. The problem is even worse for biphasic stimulus pulses shorter than about 60–80 microseconds because the reverse polarity of the second phase partially cancels the effects of the first phase before the neurons can respond to the first phase.

Advantageously, as shown in FIG. 11, the CIS frame rate for a given number of channels each with a given pulse width can be doubled by stimulating two separate sites at the same time. This violation of the non-overlap requirement for the CIS strategy is useful only if the amount of electrotonic interaction between those sites is minimal. That condition is likely to be met when the simultaneously activated sites are selected to be physically distant from each other and when the intensity of stimulation required to produce a full range of loudness at each site is fairly low. Thus, it is a particular advantage of this invention that the pattern of overlap between pulses at various sites can be readily selected and changed simply by altering the values in the template table rather than reprogramming a new algorithm for each stimulus paradigm.

Figure 12A:
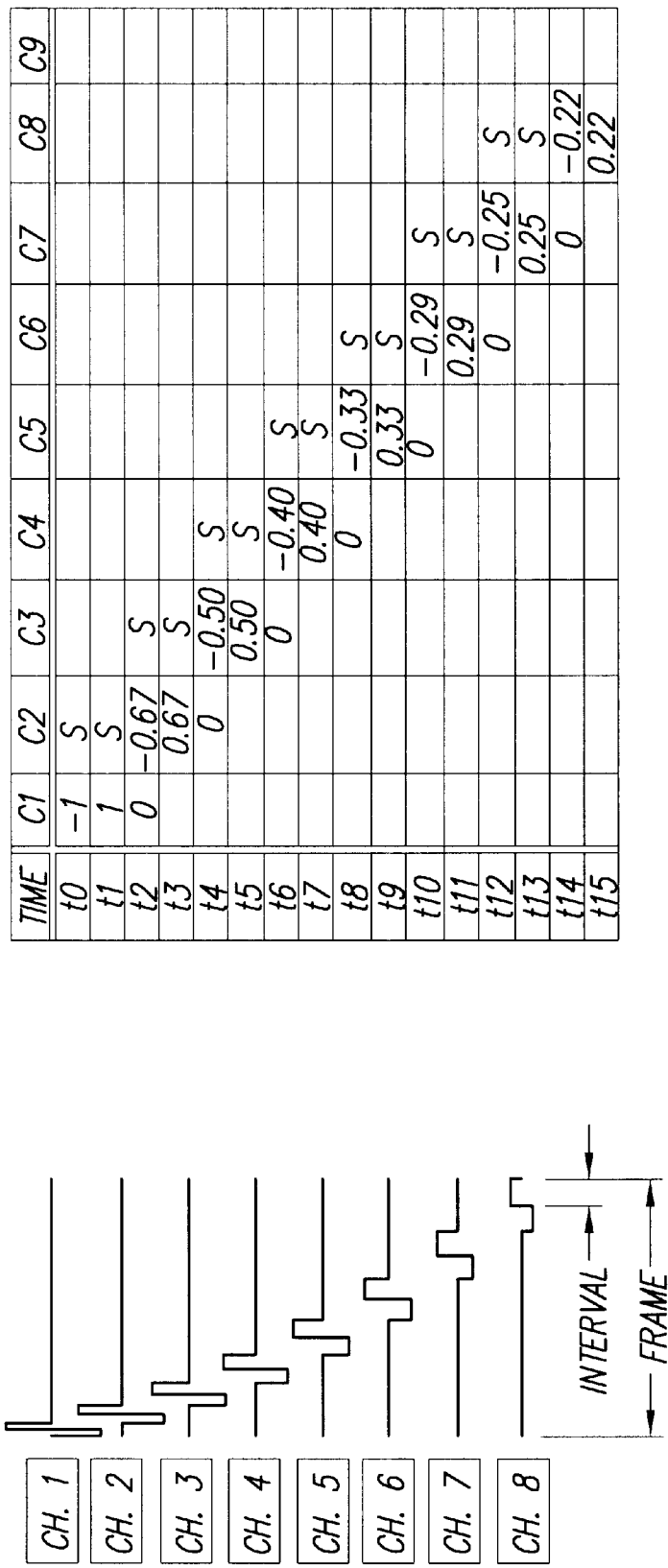
FIG. 12A shows the stimulation template for a stimulation pattern that uses short-interval transmissions to create narrow pulses and a faster overall cycle rate.

Referring next to FIG. 12A, there is shown the stimulation template for a stimulation pattern that uses short-interval transmissions to create narrow pulses and a faster overall cycle rate. A special code "S" in each row indicates that no further information will be transmitted in that frame, permitting the duration of the frame to be truncated. This also means that the time intervals used in FIG. 12A need not be equal. Rather, t0 is shorter than t1, which is shorter than t2, and so on. Further, as depicted in FIG. 12A, the weighting factors decrease with increasing time intervals in order to equalize the relative efficacy of the various durations of stimulus pulses created by the changing time intervals. Other codes and features provide additional options regarding the duration of each phase of electrical stimulation according to the programmability of the implanted circuitry that generates the output currents.

Figure 12B:
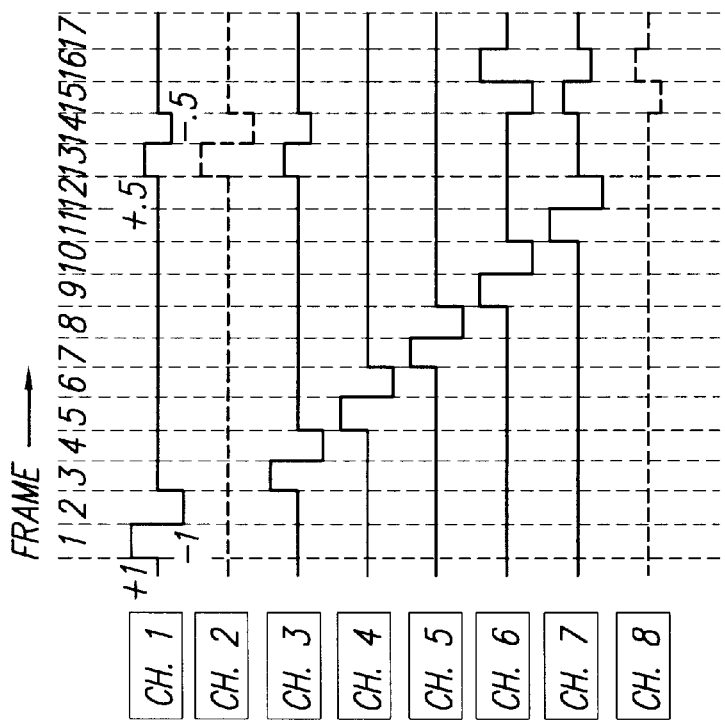
FIG. 12B illustrates an example of a virtual channel stimulation template that may be used to create two virtual channels by mapping information from eight channels into only six output stages.

Referring next to FIG. 12B, a virtual stimulation strategy is shown wherein eight bandpass filter channels are mapped into only six output stages and electrodes. This is accomplished by creating two virtual channels, identified in FIG. 12B as codes V1 and V3 (a first virtual channel), and V6 and V7 (a second virtual channel). The first virtual channel, V1–V3, is shown in column C2 to indicate that the two output stages C1 and C3 are to be summed in phase according to the weighting coefficients in rows 13 and 14.

Similarly, codes V6 and V7, in column C8, indicate that the second virtual channel is comprised of output stages C6 and C7, stimulated out of phase according to the weighting coefficients in rows 15 and 16.

From the above figures, it is seen that a great deal of flexibility may be achieved relative to the stimulation patterns and waveforms that are implemented by the ICS or equivalent stimulator device. The following codes and features are supported, as an example of the capabilities of the general scheme of the invention:

First, the output current of each current source remains at a given value unless and until it is explicitly set to a new value, so a special "null" code in the table indicates that no change is required during a particular interval, obviating the need to recompute the output current during a phase of stimulation that lasts longer than one interval or when the desired output is zero for more than one interval.

Second, if a row of the table contains no non-null codes after a given column, then a special "end" code "E" in the table can be used to signal that no further computations are required in that interval.

Third, if a row of the table contains no non-null codes after a given column, then a special "short interval" code "S" in the table can be used to abridge the normal transmission of information to the implanted electronics and immediately beginning transmitting the output states specified by the next row in the table, resulting in a shorter-than-normal interval for the output states specified in the abbreviated row.

Fourth, if the table contains an extra column for mode control of the implanted electronics, the mode value stored in the template table for each row can be transmitted to the implanted electronics at each interval. Such mode values can, for example, specify that the output current that is requested of one or more of the current sources in the subsequent interval be delayed in its onset or terminated prematurely during the course of that interval, thus creating stimulus phases whose duration is a fraction of the interval represented by each row of the table.

Fifth, the output channel designated by a column of the table may be assigned to a virtual channel composed of two or more other output channels. The virtual channel is identified by the code "Vn", where n is the number of a real output channel It should next be pointed out that the template table used by the present invention is a tool to facilitate abstraction of the desired stimulation pattern and waveforms. Other tools that achieve the same end result may also be used. For example, a list or series specification of desired spatial/temporal events may be mathematically or logically defined, and such list may then be used as input data to the microprocessor used within the speech processor. For example, the stimulation pattern and waveforms defined by the template table shown in FIG. 12A may alternately be generated by the following series:

$$C_n(t, \text{amplitude}): (2*(n-1),-1),(2*(n-1)+1,1),(2*(n-1)+2,0)$$

$$F_t(n, \text{code}): (INT(t/2)+2, S)$$

where
t=step number (t0–t15) or frame number;
n=channel number [1–9] or position in frame;
code=[S]hort,[D]efault, . . . all possible codes.

Figure 13:
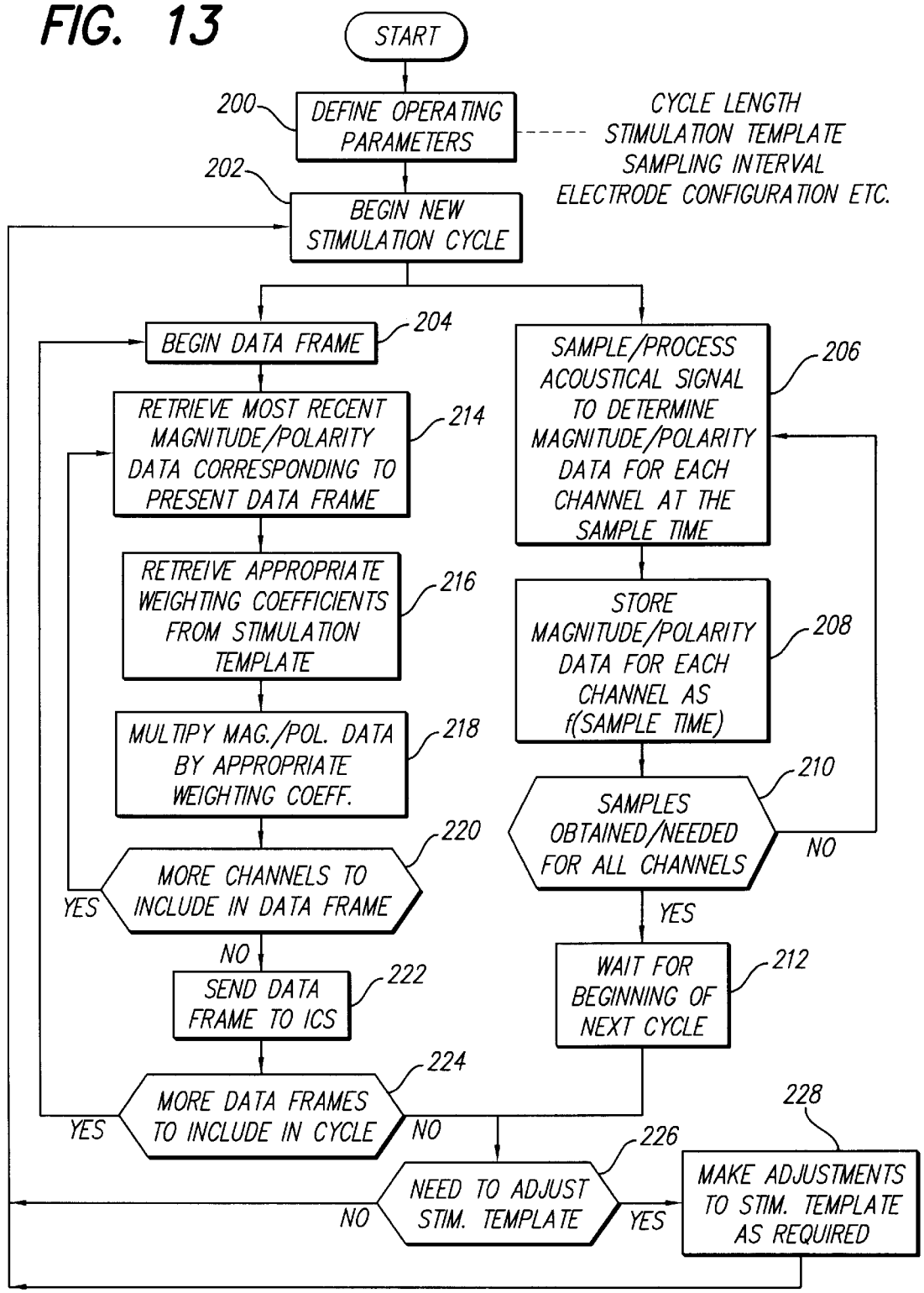
FIG. 13 is a simplified flow chart that shows how the above or other stimulation templates may be used within the speech processor portion of the invention to control the stimulation current patterns generated by the implantable stimulator portion of the invention.

Referring next to FIG. 13, a simplified flow chart is shown that depicts one method (certainly not the only method) by which the above or other stimulation templates may be used within the speech processor of the stimulator system to control the stimulation current patterns and waveforms generated by the implantable portion of the invention. Each main step of the method depicted in FIG. 13 is represented as a "block", where each block has a reference numeral assigned thereto.

As seen in FIG. 13, an initial step (block 200) is to define the appropriate operating parameters used within the speech processor 16. Such operating parameters may include such items as: the data frame interval (the time interval separating the rows in the template table), the cycle length (the number of rows in the template table), the number of channels to be used (the number of columns in the table), the electrode configuration (bipolar, monopolar, etc.), and the like.

Once the initial operating parameters are defined, a new stimulation cycle begins (block 202). As the new stimulation cycle begins, two parallel paths are initiated. In a first path, the acoustic signal is sampled and processed (block 206). Such processing results in a determination of the magnitude and polarity associated with each channel at the sample time. For the preferred ICS described herein, such processing results in generating the eight data words that make up a data frame. This magnitude/polarity information is then stored as a function of the sample time (block 208). Once such magnitude/polarity data has been obtained for each of the available channels (block 210), then this branch of the stimulation cycle waits for the beginning of the next cycle (block 212), at which time a new sample is taken and the process repeats (blocks 206, 208, 210, 212).

Meanwhile, in the parallel path initiated at the beginning of the stimulation cycle, the data frame is initiated. This is accomplished by retrieving the most recent magnitude/polarity data corresponding to the first channel to be included in the data frame (block 214). Once this data has been retrieved, the appropriate weighting factors or weighting coefficients corresponding to the first channel and time interval are also retrieved (block 216). Such retrieval of the weighting coefficients is greatly facilitated through the use of the template table or other list as described above. The magnitude/polarity data is then multiplied by the appropriate weighting coefficient (block 218) to produce weighted magnitude/polarity data. Such weighted data effectively defines the desired stimulation current for the current data frame. Accordingly, such weighted data is formatted into the data word of the frame in anticipation of sending the data frame to the ICS. If additional channel information/data is required to complete the frame data (YES branch of block 220), then such information/data is retrieved (blocks 214, 216, 218). If all of the information/data needed within the current frame has been accumulated (NO branch of block 220), then the weighted information/data is transferred to the ICS (block 222). A determination is then made as to whether additional frames are needed to complete the cycle (block 224). If so (YES branch of block 224), then the next data frame is initiated and the process repeats (blocks 204, 214, 216, 218, 220, 222, and 224).

If the cycle is complete (NO branch of block 224), i.e., if all of the data frames needed to complete the cycle have been generated, a determination may be made as to whether there is a need to adjust the stimulation template (block 226). Such determination is preferably made in cooperation with the patient, i.e., using feedback from the patient as to how well he or see is discerning certain sounds generated as part of a fitting test. If not, then the next stimulation cycle begins and the process repeats as described above (beginning at block 202).

If a need does exist for an adjustment of the stimulation template (YES branch of block 226), then such adjustment is made (block 228). Advantageously, the template table provided by the present invention, or other list of the spatial/temporal events, makes such an adjustment a very easy task. Such task may be undertaken manually, on a trial and error basis, e.g., by simply changing the weighting factors in the template table; or may be performed systematically following a prescribed adjustment algorithm.

Implantable ICS Having a Pulse Table Therein

Next, with reference to FIGS. 14–29, a preferred ICS will be described wherein a Pulse Table is incorporated with the ICS as part of the implantable portion of the system. Such an ICS will hereafter be referred to as an ICS2 to distinguish it from a prior art ICS, e.g., of the type disclosed in '726 patent. The ICS2 comprises the implantable portion of a cochlear implant system which includes receiver/transmitter electronics, stimulation electronics, mechanical packaging, and an electrode array. The mechanical packaging and electrode array may be of conventional design, or as described in the referenced patent documents.

In operation, the ICS2 receives power and commands from an external unit in order to provide controlled, customizable current stimulus signals to the electrode array. In addition, the stimulator monitors internal voltages such as power supply levels and electrode potentials and transmits that information back to the external unit on demand.

Figure 14:
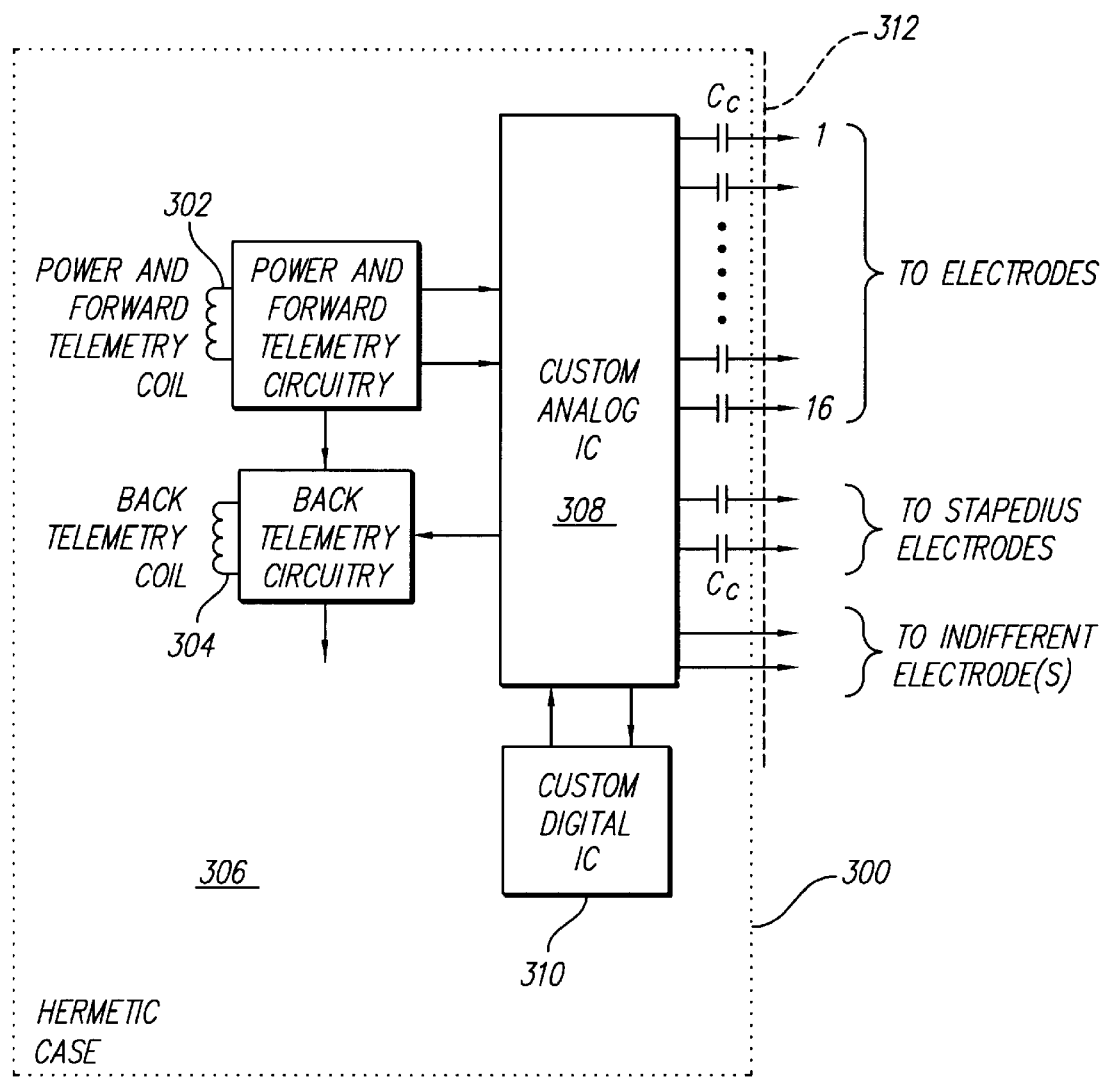
FIG. 14 depicts the physical partitioning of the ICS circuitry in accordance with a preferred embodiment of the invention.

The physical partitioning of the ICS2 is illustrated in FIG. 14. As seen in FIG. 14, the ICS2 consists of electronic circuitry that fits inside a hermetically sealed, U-shaped ceramic case 300, e.g., of the type disclosed in U.S. Pat. No. 4,991,582, incorporated herein by reference. The package design may be the same as is used by ICS described in the '726 patent, previously referenced. The power and telemetry coils 302, and the back telemetry coil 304, and all circuitry are mounted on a ceramic hybrid 306 inside the case 300. The majority of the circuitry is integrated into custom integrated circuits (ICs). Two IC's are employed—one analog IC 308 and one digital IC 310. Discrete components are used as necessary, e..g, coupling capacitors Cc. Attachment of the circuitry to the sixteen external electrodes and one indifferent (reference) electrode is through a bulkhead connector 312 at one end of the case. (Note that Electrodes are numbered 1 through 16, with 1 the most apical and 16 the most basal.) Provision for an additional indifferent electrode and two stapedius electrodes are also made in the ICs.

Figures 1, 15:
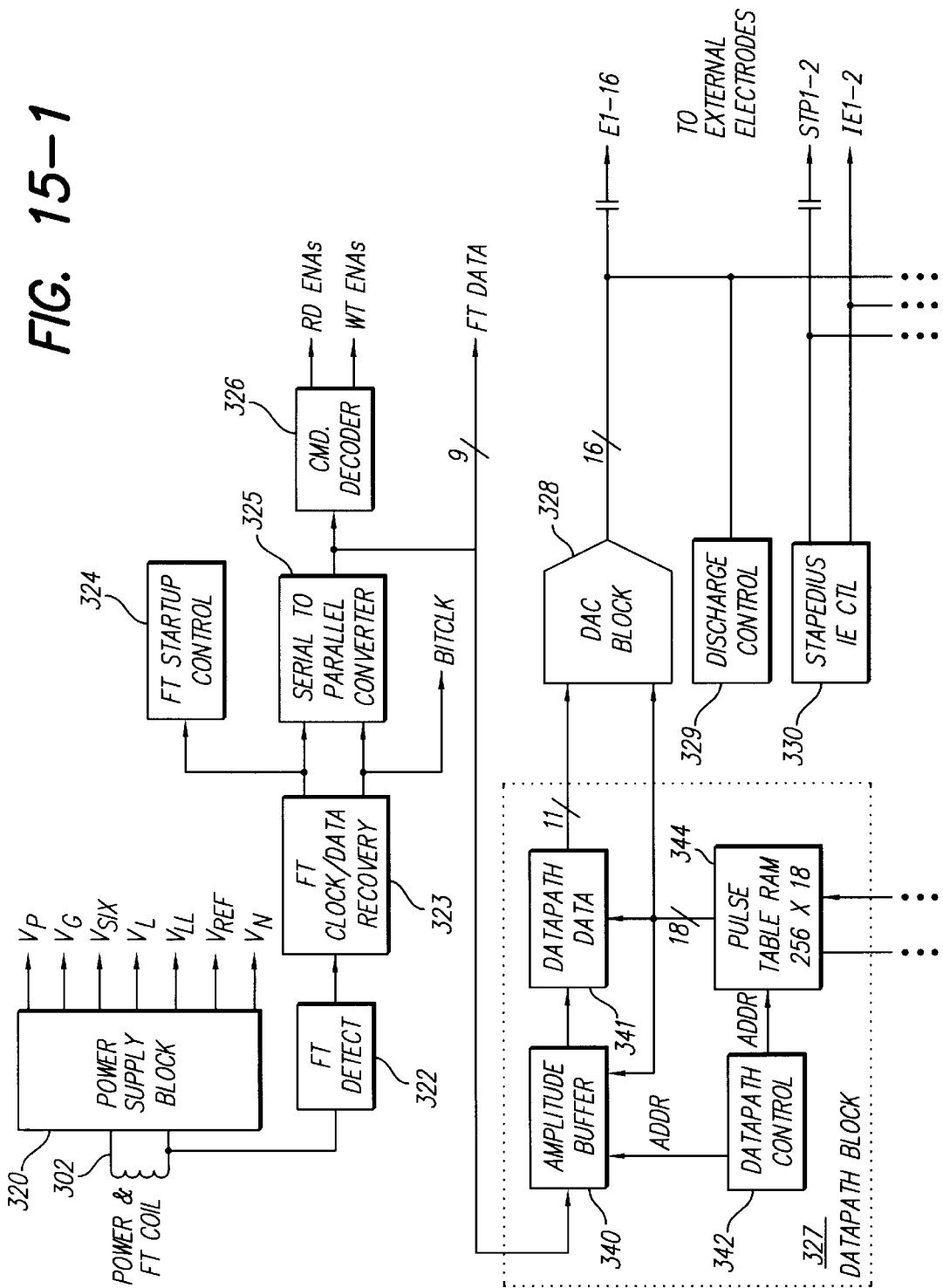
FIG. 15 shows the functional partitioning of the preferred ICS.
Figures 2, 15:
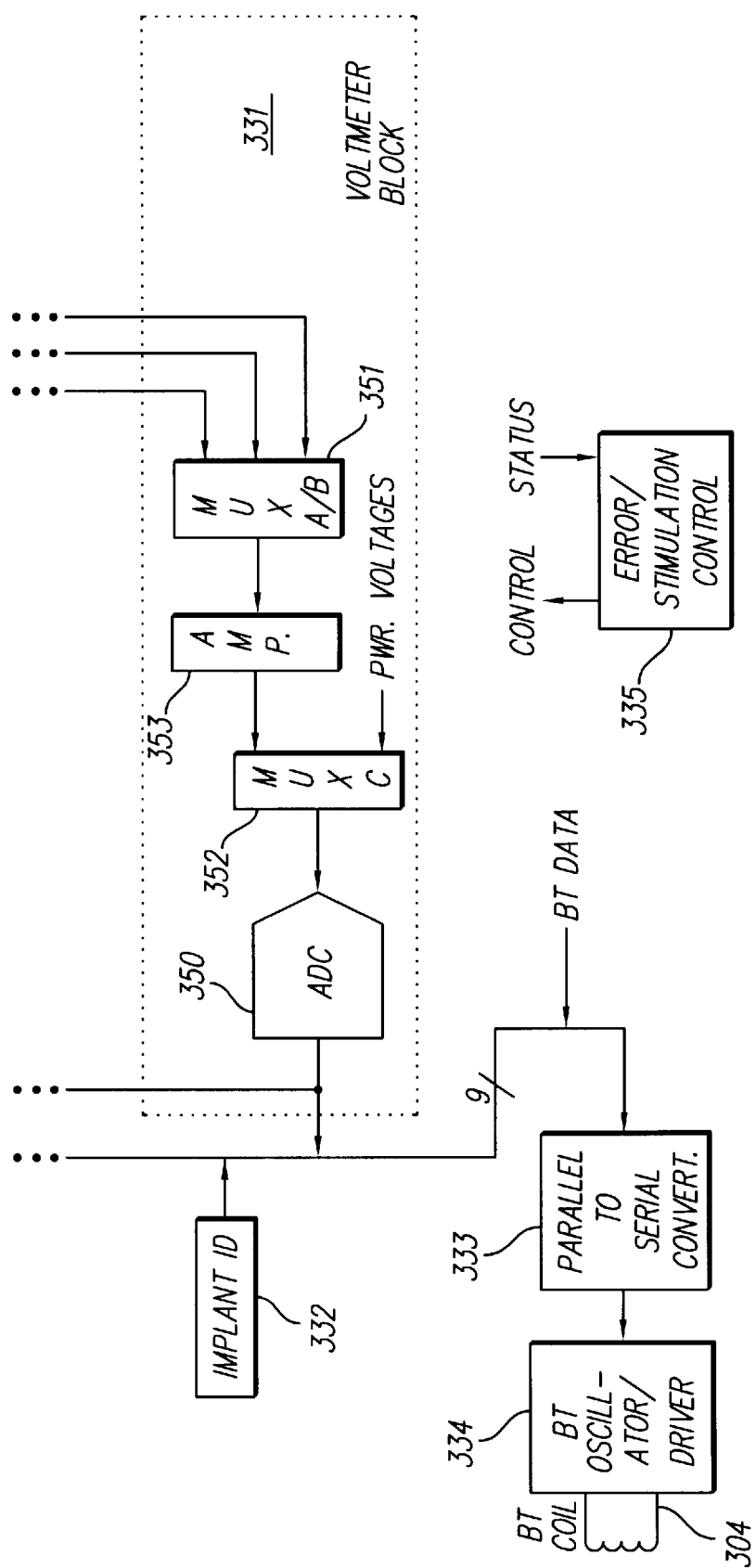

The functional partitioning of the ICS2 is shown in FIG. 15. As seen in FIG. 15, the ICS2 functionally includes a power supply block 320, a forward-telemetry (FT) detector 322, a FT Clock/Data Recovery circuit 323, a FT startup control circuit 324, a serial-to-parallel converter 325, a command decoder 326, a data path block 327, a digital-to-analog (DAC) block 328, a discharge control circuit 329, a stapedius/indifferent electrode control circuit 330, a voltmeter block 331, an implant identification block 332, a parallel-to-serial converter 333, a back telemetry (BT) oscillator and driver circuit 334, and an error and stimulation control circuit 335.

The Power Supply Block 320 receives a 49 Mhz RF carrier from the Power and Forward Telemetry (FT) Coil 302 and provides the following DC voltages to the ICS:

$V_P$—Highest positive voltage: +6.6 V to +16 V above IC substrate This is the positive analog supply.

$V_G$–$V_P$ divided by two. This is analog ground, and is normally at body potential.

$V_{SIX}$—ADC regulated supply, +6 volts above IC substrate.

$V_L$—Logic regulated supply, analog chip, +3 volts above IC substrate.

$V_{LL}$—Logic regulated supply, digital chip, +1.8 volts above IC substrate.

$V_{REF}$—Regulated voltage reference, +1.2 volts above IC substrate.

$V_N$—IC substrate level and digital ground

The $V_P$ and $V_G$ levels are unregulated and are controlled externally by varying the power level of the 49 Mhz carrier. The Power Supply Block also furnishes the power-on reset signal, which is active when $V_L$<2.25 V (nom).

The Forward Telemetry (FT) Detector 322 receives the amplitude-modulated 49 Mhz carrier (generated by the external speech processor) from the coil 302 and outputs a logic-level 1.11 Mbit/sec FM-encoded serial data stream.

The FT Clock/Data Recovery circuit 323 takes the FM- (to be specific, biphase-mark-) encoded data stream and outputs a 1.11 MHz clock and the decoded serial data stream. The 1.11 Mhz clock is the main system clock (also known as BITCLK), and all timing is based on this clock.

The FT Startup Control circuit 324 monitors the decoded serial stream and determines when the phase-locked-loop (PLL) in the recovery circuit has achieved lock. (Lock time is approx. 100 usec.) The FT Startup Control waits for 200 usec. of correctly-decoded all-zeros startup pattern to determine that lock has occurred.

The Serial to Parallel Converter 325 receives the decoded FT serial data stream and packs the data into 12-bit words. This block also checks for odd parity in each 12-bit word. The lower 9 bits of this word can be used as amplitude or write-command data, depending on the particular command.

The command decoder 326 takes the parallel FT data, and decodes read and write commands to registers and memory in the ICS. In the case of write commands, 9 bits of the FT data are written into a selected register or memory location, for initialization and control purposes. In the case of read commands, a selected location is read and the data is transmitted to the external portions of the speech processor via the back-telemetry (BT) link. This block outputs the read- and write-enable signals to the rest of the ICS2.

The Datapath Block 327 generates the digital representation of the stimulus signals, which are then output to the DAC block 328. The Datapath is a programmable state-machine that generates repetitive waveforms on 16 channels. These waveforms are amplitude-modulated by data that is supplied on a real-time basis by the external portions of the speech processor. The Datapath Block 327 is further broken down into the Amplitude Buffer 340, the Datapath Data logic 341, the Datapath Control logic 342, and the Pulse Table RAM 344.

The Pulse Table RAM 344 functions as the Pulse Table 42 (FIG. 3A). The Pulse Table RAM 344 controls the shape and relative timing of the stimulus signals. It is a 256-word-by-18-bit block of memory. Each word in the table defines one output transition for one of the 16 DACs included in the DAC block 328. Various fields in the Table address the particular DAC, provide a read address for the Amplitude Buffer, control arithmetic and logic functions on the stimulus data, and provide sequence control for the state machine. The Pulse Table 344 is written by the external portions of the speech processor prior to the start of stimulation.

The Amplitude Buffer 340 is smaller memory (32 by 9) that stores the audio-derived amplitude data received through the external portions of the speech processor. Amplitude data is in the form of 9-bit sign-magnitude words, and is organized into frames of up to 16 words each. The Amplitude Buffer 340 double-buffers the data, receiving a one frame while the Pulse Table 344 addresses the previous frame.

The Datapath Data block 341 performs various arithmetic and logic functions on the amplitude data and outputs the signed, 11-bit result to the DACs within the DAC block 328.

The Datapath Control block 342 controls overall timing for the state machine. This logic is driven by the 1.11 MHz system clock, and so all stimulus timing is based on a programmable time interval, which is an integral number of system clock periods. This logic generates the read address for the Pulse Table RAM 344 and the write address for the Amplitude Buffer 340.

The DAC Block contains 16 11-bit current mode DACS that drive the stimulation electrodes. The DACs are bipolar, so they each sink or source current depending on the state off the sign bit. Specifications for the each DAC is as follows:

Input: 11-bit sign-magnitude data

Output Current Ranges: 0–255 uA, 0–510 uA, 0–1020 uA, 0–2040 uA (current range is programmed globally.)

Rise Time: <1 usec to 66% point with 10 Kohm load.

Setting Time: <3 usec

Minimum Pulse Width: 10 usec

Compliance voltage: +/−3.3–8 V relative to $V_G$ as determine by $V_P$ level.

Differential Non-Linearity: TBD

Integral Non-Linearity: TBD

Monotonacity: TBD

In addition, each DAC input is double buffered so that DAC outputs can be updated simultaneously after the Datapath data logic 341 sequentially sets up the next value for each channel. A detailed description of the DACS used within the DAC Block 328 may be found in copending patent application Ser. No. 60/090,833, filed Jun. 26, 1998, which application is assigned to the same assignee as is the present application, and which application is incorporated herein by reference.

Still with reference to FIG. 15, the Discharge Control block 329 allows a discharge resistor to be programmably connected to each stimulation electrode in order to drain off any charge unbalance. The follow resistor values are available:

None (open)

150 Kohm

300 Kohm

150 K∥300 Kohm

In addition to the discharge resistors (which are programmed statically), this block 329 also contains switches to dynamically short each electrode to analog ground ($V_G$), under control of the pulse table and/or the amplitude data from the external speech processor.

The Stapedius/Indifferent Electrode Control block 330 contains switches that can programmably connect the Indifferent and Stapedius Electrodes to analog ground ($V_G$).

The voltmeter block 331 contains an analog-to-digital converter (ADC) 350 along with analog multiplexors 351, 352 and a high-gain amplifier 353. This block 331 digitizes potentials present on the ceramic hybrid 306 as well as internal power supply voltages. The voltmeter block 331 is used for three basic functions:

(1) Monitoring of power supplies during normal operation;

(2) Measurement of electrode impedance during fitting; and (3) Measurement of evoked neural response to stimulus for fitting and Research purposes.

The "A/B" multiplexor 351 advantageously can select any of the electrodes as sources for the differential inputs of the amplifier 353. The amplifier 353 is programmable with a gain of 1 to 1000, and is designed for recovery of input overloads, to facilitate the measurement of low-level neural response signals following a stimulus pulse. The "C" multiplexor 352 selects between the output of the amplifer 353 or the power supply voltages as inputs to the ADC 350.

The ADC 350 has a 9-bit twos-complement output, with programmable sampling rates of 60 Khz, 30 Khz, and 10 Khz. Combined with the amplifier gain, the ADC 350 can resolve input signals as small as 10 uV. The ADC output can either read directly over the back-telemetry link (in the case of a single-sample capture), or can be automatically stored in unused locations in the Pulse Table RAM 344. In the latter case, the RAM contents would be read back over the BT link after the capture has completed.

Additional details associated with the function of the Voltmeter block 331 may be found in copending patent application Ser. No. 60/090,820, filed Jun. 26, 1998, assigned to the same assignee as is the present application, which application is incorporated herein by reference.

The Implant Identification block 332 provides a 16-bit ID number that is unique to each ICS2, to support tracking and calibration functions in software. The ID number is assigned by means of bond wires on the hybrid during manufacture The Parallel-to-Serial Converter 333 takes the 9 bits of BT data generated by a read command and serializes it, adding start, top and parity bits. The resulting 111 Mbit/sec NRZ serial data stream goes to the driver electronics of the BT Oscillator/Driver circuit 334 for transmission to the external portions of the speech processor.

The BT Oscillator/Driver circuit 334 takes the 123 Mbit/sec BT serial data stream output from the Parallel to Serial Converter 333 and outputs an FSK modulated signal with a 10.7 Mhz carrier, which drives the back telemetry coil 304.

The Error and Stimulation Control block 335 enables stimulation, and monitors various error signals from the rest of the ICS2. Various responses to errors may be programmably selected.

Power Supply

Figure 16:
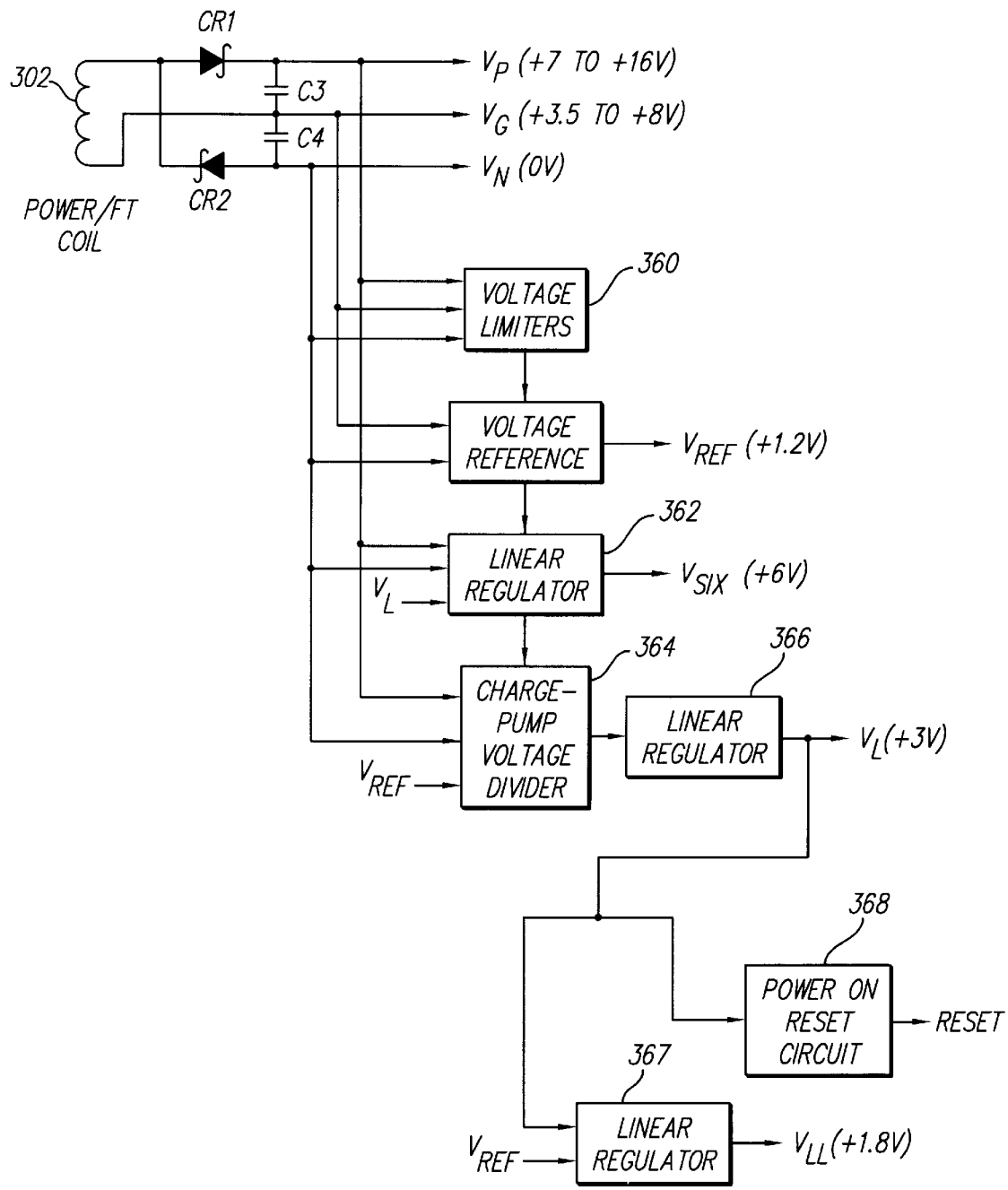
FIG. 16 is a block diagram of the power supply portion of the ICS.

Turning next to FIG. 16, a block diagram of the power supply block 320 is shown. As seen in FIG. 16, $V_P$ and $V_G$ are the full-wave rectified by diodes CR1 and CR2 and filtered by capacitors C3 and C4 from the 49 Mhz carrier received from the coil 302. The center tap of the capacitors C3 and C4 provides a voltage reference, $V_{Ref}$, which is about +1.2 volts. The $V_P$ and $V_G$ voltages are unregulated, but have limiters 360 to control the maximum voltage to 16 V and 8 V above substrate, respectively. The $V_{SIX}$ supply has a linear regulator 362, whose efficiency is determined by the voltage levels of $V_P$. The Vsix supply uses the +3 V $V_L$ voltage as a reference, so that Vsix is exactly twice $V_L$. The $V_L$ supply uses a charge-pump 364 to divide $V_P$ by 2,3, or 4. The output of the charge-pump feeds a linear regulator 366 to produce the +3 V output. This scheme gives a worst-case conversion efficiency of about 60%. The $V_L$ output feeds another linear regulator 367, which outputs the +1.8 V $V_{LL}$ supply. The charge-pump 364 is disabled at startup and under program control when low-noise operation is needed. In that case the $V_L$ regulators are fed by $V_G$. Finally, $V_L$ is monitored by a power-reset circuit 368, which asserts reset whenever $V_L$ is below approx. 2.25 V.

The serial data stream delivered to the ICS2 is amplitude-modulated on a 49 MHz carrier with an FM encoding scheme (not to be confused with Frequency Modulation of the carrier) known as bi-phase mark. This coding scheme allows extraction of both clock and data from the serial stream and has zero DC component over time. The format of the bi-phase mark encoding scheme is as follows: at every bit time there is a level transition, and in the middle of each bit time there is a transition if data is a 1. Such coding scheme is illustrated in FIG. 17.

Forward Telemetry

Turning next to FIG. 18, the method of forward telemetry data detection is illustrated. As seen in FIG. 18, data detection is accomplished by sensing current in one of the legs of the coil 302, between the rectifier diode CR2 and the filter capacitor C4. Current flowing through the resistor R1 is sensed as a voltage by an ac-coupled comparator 370. A second, dc-coupled comparator 372 detects when the voltage level drops below ground ($V_N$), to determine if any signal is present. A second series diode CR3 is used to limit the voltage drop across R1 in high-current-draw situations.

In the preferred ICS2 embodiment, the serial data rate is 1.1136364 Mbits/sec (49/44 Mbits/sec). Data recovery is accomplished using a phase-locked loop. The transitions in the data stream are differentiated, and the resulting pulses are input to a phase detector. The other phase-detector input is the 1.11 MHz divided-down output of a VCO. At initialization time an all-zeros data stream allows the PLL to lock. Once the loop locks, data transitions occurring in the middle of the bit time (for 1s) are gated off, so that the phase detector only sees the transitions at the start of each bit time. The data separator checks for these transitions and signals a "missing clock" error if a transition is not seen at start of the bit time.

To initialize the forward telemetry (FT) link, the external portion of the speech processor must first send all zeros for approximately 300 usec. (This gives enough time for the loop to lock, and for the ICS2 to detect lock.) The external portion of the speech processor then sends a special word consisting of 12 ones. This establishes word boundaries and signifies the start of actual data transmission.

Forward telemetry data is organized as 12-bit data words. These data words are transmitted serially with the LSB first, and last bit is an odd parity bit. Data words are broken down into two basic types: command words and amplitude words. Command words are distinguished from amplitude words by the 11th bit (Bit 10, where the first bit is Bit 0), which is a "0" for a command word, and a "1" for an amplitude word. The format for the forward telemetry command words and amplitude words is illustrated in FIG. 19.

Command words allow the reading and writing of control/status registers and of the Pulse Table RAM 344. Commands can be either single- or multi-word. All reads are single-word and all writes are multi-word. In the case of a write, the first word is as shown in FIG. 19, with a 1 in the CMDSEQ field. The second word contains the write data: bits 9–11 are as described above for a command word, and bits 0–8 contain the 9-bit value to be written. This format continues for as many data words are in the multi-word command. The last data word in that command has a 0 in the CMDSEQ field (Bit 9).

In the case of the Pulse Table RAM 344, there are not enough bits in the command word to directly address the RAM, which appears to the telemetry interface as 512 9-bit words. Thus, a separate address register is used, and a special register number (0×3 F) in the command selects the RAM. The address register supplies the address within RAM, and can be auto-incremented after each access. (The address register is initialized through a normal register write.) Up to 512 words can be written to RAM in a multi-word command.

A checksum mechanism is provided to help insure data integrity in write operations. If a write is initiated with the CRC bit set, both the write command word and the subsequent data word(s) are added to a checksum register. A status bit indicates to the software if the checksum equals zero. In addition, the checksum state can be used to interlock the start of stimulation. A write to a dedicated register location initializes the checksum total. (Note the name "CRC" is a misnomer that exists for historical reasons; the operation is a simple checksum rather than a cyclic redundancy check.)

Read commands return a single 9-bit word from the selected register or RAM location, and the data is transmitted through the back telemetry link.

Amplitude words represent audio-derived data that are supplied in real-time by the external portions of the speech processor. Amplitude words are used to modulate the stimulus outputs of the ICS2. These are 9-bit, sign-magnitude values that are organized in frames of up to 16 words each. (The sign bit can be configured to operate as a "skip" bit for NofM strategies.) A SYNC bit in the amplitude word (Bit 9) denotes the start of each amplitude frame.

In the ICS2, no word-framing bits are used in the forward telemetry format. Hence, data must be transmitted continuously once the link has been established. A special command word, termed NOP, is used to fill time slots when neither command words nor amplitude words need to be sent. The NOP is a command word where both the DIR and CMDSEQ bits are zero.

Back Telemetry

The back telemetry (BT) link supports a 123 Kbit/sec serial data steam, which is "NRZ-space" encoded. The carrier is 10.7 Mhz, and frequency-shift key (FSK) modulation is used. The frequency shift is plus or minus 70 Khz. In other words, the BT transmitter outputs carrier at 10.63 Mhz for a 0 bit, and 10.77 Mhz for a 1 bit. Either of two alternate schemes may be used for generating the back-telemetry signal: In the first scheme, the back-telemetry carrier is generated by an LC oscillator, with the frequency shift is accomplished by switching an additional capacitor into the tuning circuit. Carrier center-frequency tolerance is 50 Khz, and is adjusted during manufacture. In the second scheme, a PLL-based frequency synthesizer is used, with the reference derived from the forward-telemetry PLL. The second scheme requires no factory adjustment, but is sensitive to spectral purity in the forward-telemetry PLL. The back-telemetry carrier can be turned on and off under program control in order to save power when read commands are not being issued.

Back-telemetry data uses an "NRZ space" data encoding scheme. In this scheme, a 0 bit is represented by a change in level, and a 1 bit is represented by no change in level.

The maximum transition rate for an "NRZ space" scheme is the same as with "standard" NRZ (also known as "NRZ level"), but a high minimum transition rate is guaranteed at startup time and between data words, assuming that zeros are transmitted during those times. Also, the use of a zero stop bit and an odd parity bit guarantee at least two transitions per word.

The back telemetry data format is organized as 12-bit words, which include start and stop bits. Thus, back-telemetry data need not be transmitted continuously while the carrier is on. Back telemetry data is transmitted with the least-significant bit first. The back telemetry word format is shown in FIG. 20.

The back-telemetry data rate of 123 Kbits/sec is equal to the forward-telemetry bit rate divided by 9. The clock divider is initialized to a known state upon receipt of the FSYNC word that establishes forward-telemetry communication. Thus the speech processor can determine the back-telemetry bit boundary times.

Pulse Table

The Pulse Table RAM 344 (FIG. 15) comprises a 256-by-18 memory that defines the speech processing strategy to be used by the ICS2, i.e., the Pulse Table RAM controls the basic waveform shape and relative timing for the output stimulus. The format of the Pulse Table word, including a description of the fields used in the Pulse Table word, is shown in FIG. 21.

The Pulse Table RAM is in effect dual-ported. One port is addressed by the Datapath Control logic 341 and supplies the 18-bit table entry that controls the Datapath. The other port appears as 512 9-bit words, and can either be accessed by FT read and write commands, or can receive data from the ADC 350 for block captures. During the time that a block capture is in process, the read/write command access is disabled.

Advantageously, some of the information stored within the pulse table may be used to help fashion a neural conditioning signal that may be added to amplitude data (i.e., real-time modulation data) stored in the amplitude buffer memory. Such neural conditioning signal is used to place the neurons associated with the spiral ganglion cells in a stochastic mode where they may be more receptive to the stimuli to be provided. This allows the applied stimulation to be more effective in extracting understandable speech features from the stimulation.

Datapath Data

Figure 22:
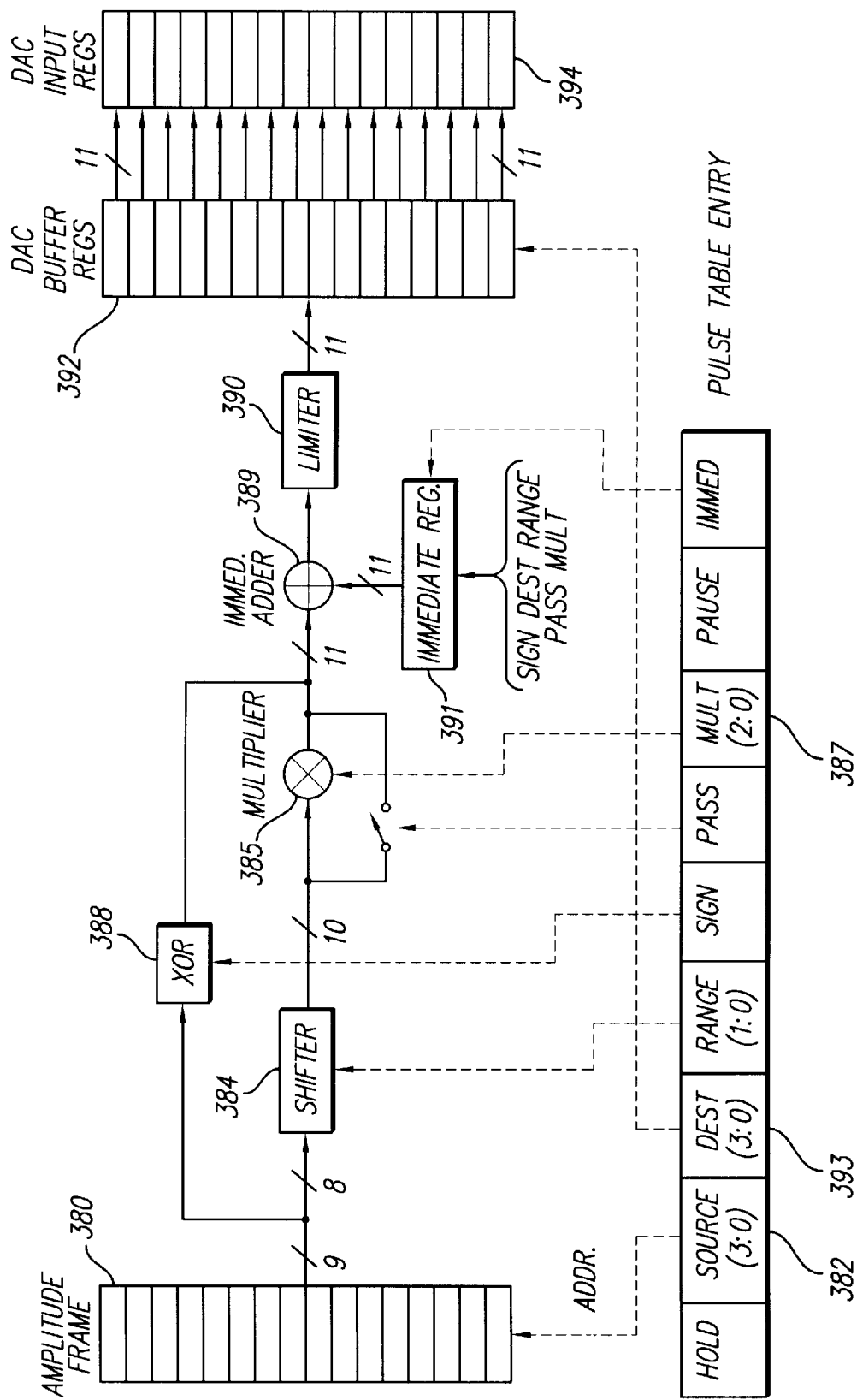
FIG. 22 is a block diagram that illustrates the data path through the ICS.

FIG. 22 is a block diagram of the Datapath, showing the manner by which the data in the Pulse Table word fields controls the data path. As seen in FIG. 22, one of 16 signed, 9-bit amplitude words is selected from the amplitude frame 380 by the Pulse Table SOURCE field 382. Next, the 8-bit magnitude portion of the selected amplitude word is shifted left, in shifter 384, by 0, 1, or 2 bits, as determined by the RANGE field. The 10-bit result is then multiplied, in multiplier 385, by from 0 to 1 in $\frac{1}{8}$ increments, under control of the PASS field 386 and MULT field 387. Meanwhile, the amplitude sign bit is XORed with the SIGN bit from the table entry in XOR circuit 388. The combined 11-bit value is added, in adder 389, to a previously-stored immediate value, stored in register 391, if the IMMED bit in the prior table entry was set. Finally, the upper 9 bits of the magnitude of this sum are compared to a limit value stored in a static register, and the output is clamped to that value by limiter 390. This result is stored in one of 16 DAC buffer registers 392, as determined by the DEST field 393. At the end of each update interval, the contents of all 16 DAC buffer registers are clocked into DAC input registers 394, so that all DACs are updated simultaneously.

Datapath Control

Figure 23:
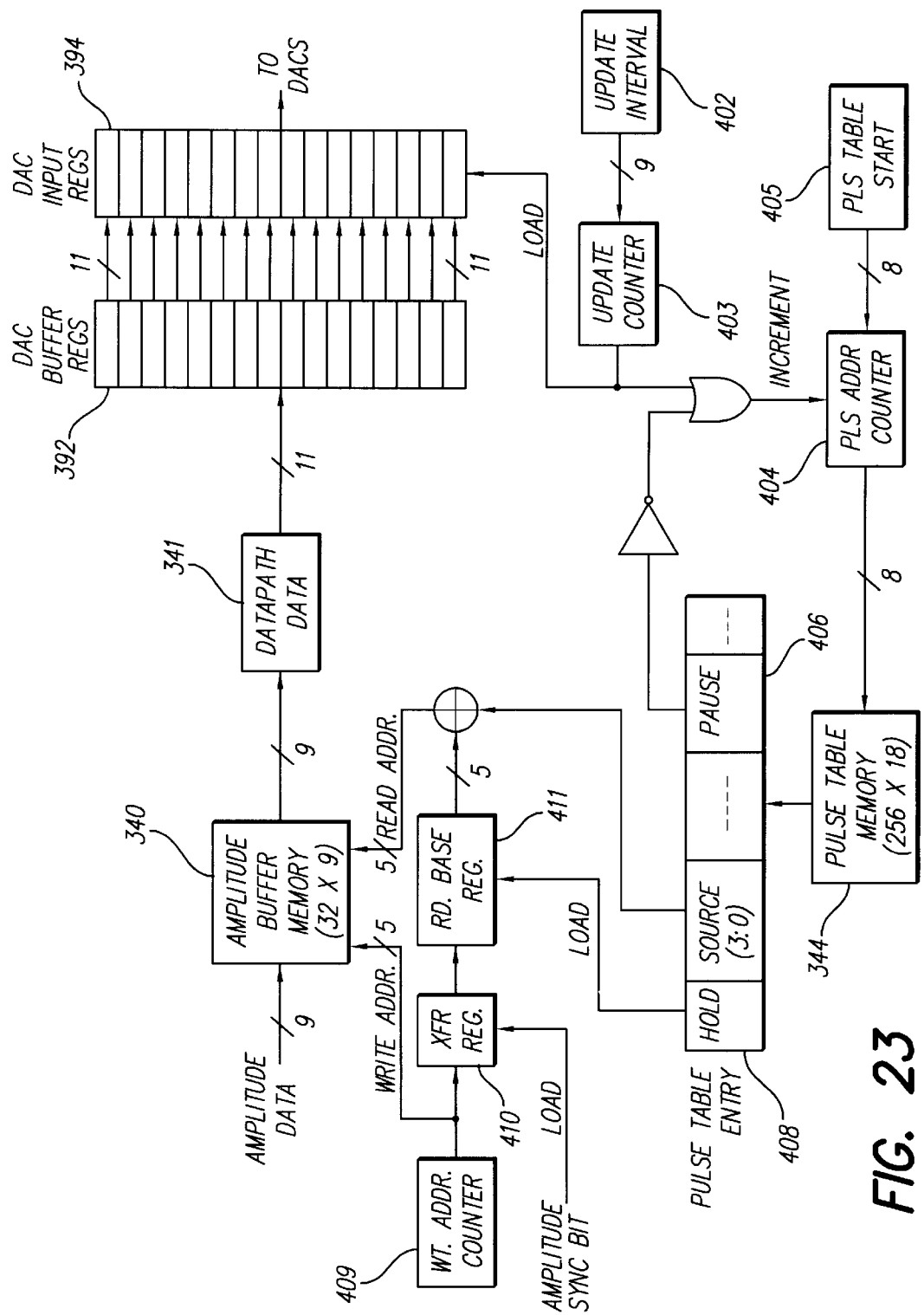
FIG. 23 is block diagram that shows the control data path through the ICS.

FIG. 23 shows the Datapath Control logic block diagram. The basic stimulation timing is controlled by an Update Interval register 402, which determines the number of 0.898 usec BITCLK periods in the update interval. The register 402 is the starting value for a 9-bit counter 403, which increments every BITCLK. Each time this counter rolls over, the DAC input registers 394 are loaded. Thus, the update interval represents the minimum time resolution of the DAC outputs, also referred to as the pulse width.

The address for the Pulse Table Memory 344 comes from another counter 404, whose starting value is held in the Pulse Table Start register 405. The counter 404 counts up every bit clock, provided either the PAUSE bit 406 in the pulse table entry 408 is zero, or the update counter 403 rolls over. In other words, if a pulse table entry contains a 1 in the PAUSE field, the instruction won't be executed and the next pulse table entry won't be fetched until the update counter rolls over.

Also shown in FIG. 23 is the addressing mechanism for the Amplitude Buffer Memory 340, although this hardware is not directly visible to the programmer. The Amplitude Buffer Memory 340 is physically implemented as a 32-by-9 memory. The write address comes from a 5-bit counter 409, and each time an amplitude word comes in from the forward telemetry link, the counter is decremented. When an amplitude word comes in with its SYNC bit set, the contents of the write address register are copied into a holding register 410, called the XFR register. In effect, this register 410 contains the starting address of the most recently received data frame.

When a pulse table entry word whose HOLD bit is a 1 is executed, the contents of the XFR register are copied to another register 411, called the Read Base. This means that subsequent pulse table entries will access the new data frame. The Read Base is added to the SRC field in the pulse table entry to produce the actual read address for the Amplitude buffer 340.

DAC Outputs and Electrode Connections

Figure 24:
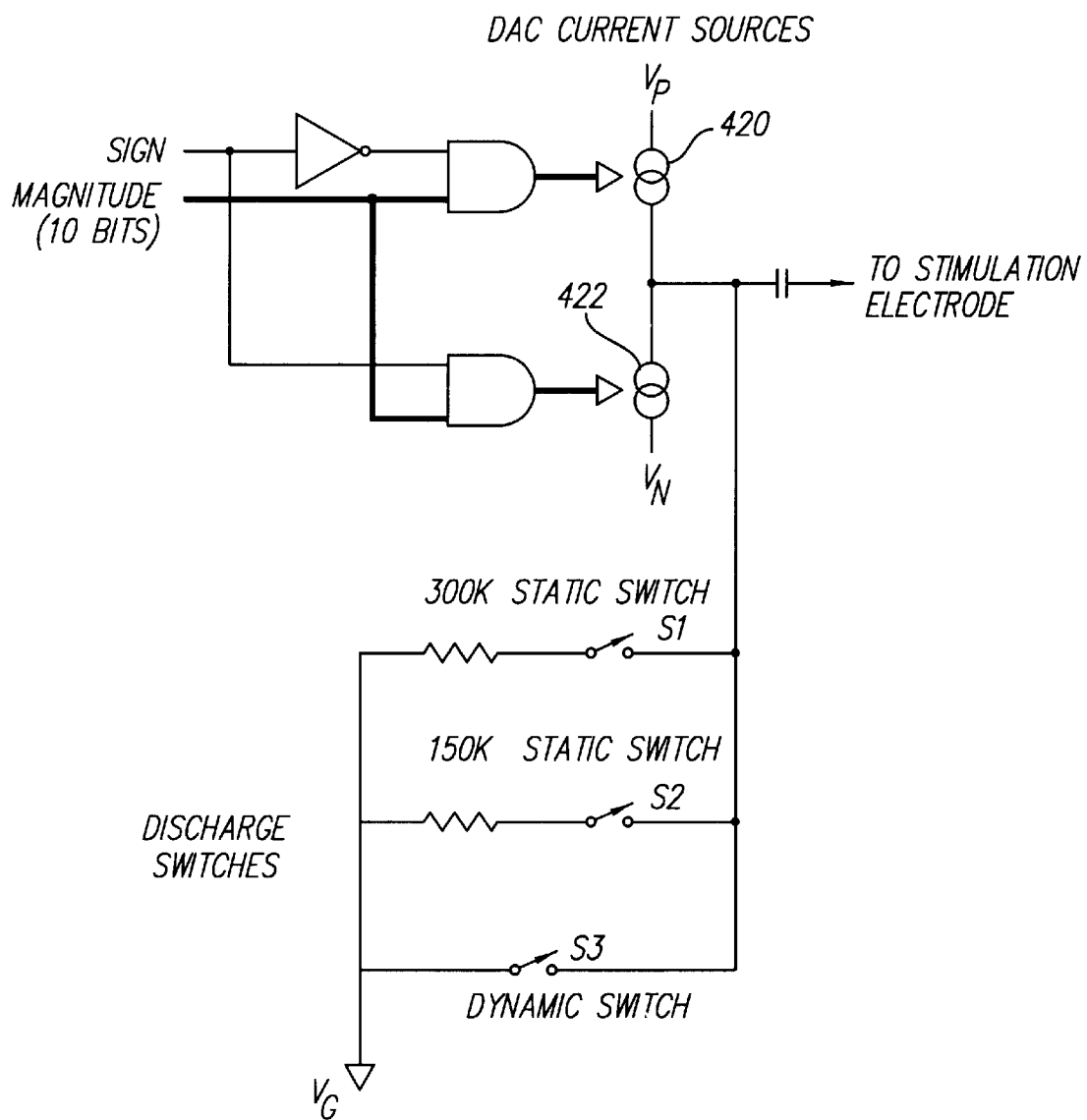
FIG. 24 is a schematic diagram of the output circuits of the ICS which are connected to most of the stimulation electrodes.

FIG. 24 illustrates the stimulation output structure for electrodes 1–15. Each electrode has its own current-mode DAC 420 and 422, which has an 11-bit sign/magnitude digital input. Depending on the sign, the DAC either sources current (DAC 420) from $V_P$, the most positive supply voltage, or sinks current (DAC 422) to $V_N$, the most negative. Each electrode also has three discharge switches S1, S2, and S3. Two of these, S1 and S2, are static, meaning that they are enabled by bits in a writable register. The switches S1 and S2 can connect a 300 K or a 150 K ohm resistor between the DAC output and $V_G$, which is analog ground (halfway between $V_N$ and $V_P$). The third switch S3 is dynamic, meaning that it is closed by a "negative zero" condition in either the amplitude word or the pulse table. The switch S3 shorts the DAC output to $V_G$.

Figure 25:
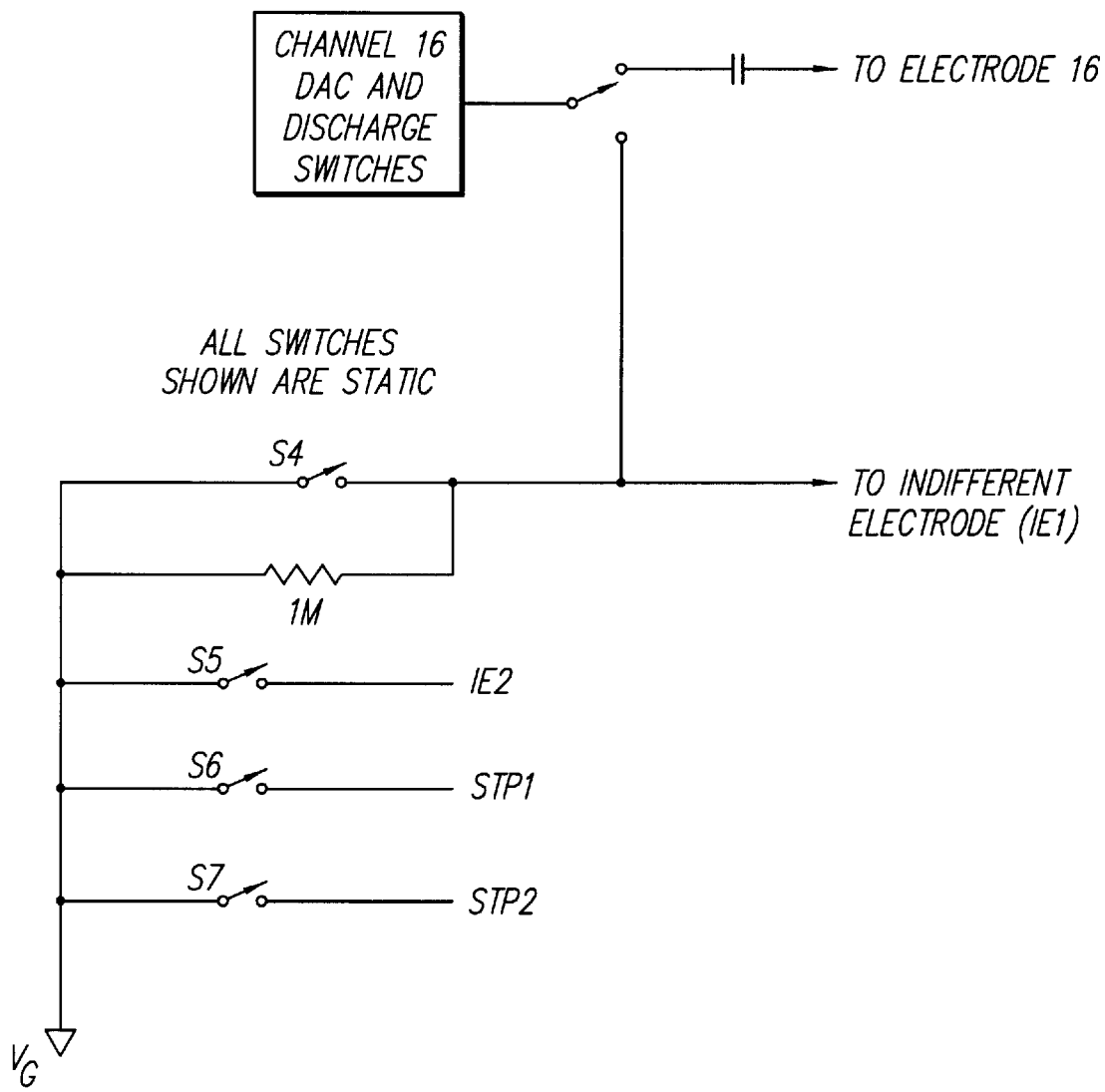
FIG. 25 is a schematic diagram of the output circuit connected to the most basal electrode of the electrode array and to an indifferent (reference) electrode.

Turning next to FIG. 25, the output structure of the Indifferent Electrode (reference electrode) and for stimulation electrode 16 (the most basal electrode) are shown. As seen in FIG. 25, a static switch S4 is used between IE1 and $V_G$. This is left open for bipolar operation and closed for monopolar operation. In addition, IE1 can be connected to the output DAC for channel 16. This allows the compliance voltage to be effectively doubled when using the monopolar, non-simultaneous stimulation. In this case IE1 would be driven with the opposite value of the stimulating electrode at any given time. The tradeoff of this scheme is that only 15 electrodes are available for stimulation. Note that IE1 also includes a 1 M ohm resistor connected to $V_G$, which permits a gradual discharge of that electrode at power-up time. Also shown are the grounding switches S5, S6 and S7 for electrodes IE2, STP1, and STP2.

Modes of Operation

ICS2 Initialization

Power-up initialization consists of the following: At power-on reset, the ICS2 FT Startup Control logic 324 (FIG. 15) puts the forward-telemetry data separator into an "acquire" mode, where all transitions in the forward-telemetry data stream are delivered to the PLL phase detector. Initially the speech-processor must send an all-zeros data stream so that the PLL locks to the "1F" frequency. The logic waits until it has correctly received 200 "zero" data bits, and uses this to determine that the PLL has locked. ("Correctly received", as used here, means there are no missing transitions at bit boundaries and no additional transitions between bit boundaries.) The logic then takes the data separator out of acquire mode, so that subsequent transitions occurring in the middle of a bit time do not affect the phase detector.

During initialization, the speech processor must transmit the all-zeros pattern long enough for the ICS2 power supply voltages to reach operating levels (the FT carrier also supplies power), for the PLL to lock, and for the FT Startup Control logic 324 to count 200 zeros.

Once at least 200 zeros have been sent, the speech processor sends a special data word consisting of 12 ones. This is known as the FSYNC word and its transmission signifies the start of data transmission. The ICS2 uses this to delineate word boundaries. All subsequent data is treated as 12-bit command or amplitude words, as described above.

To verify that forward telemetry has been established, the speech processor may send a command word to turn on back telemetry. If the speech processor thereafter detects the presence of the back-telemetry carrier, then this provides the verification that forward telemetry has been established.

Stimulation Startup

Prior to starting stimulation, the external portions of the speech processor sends various command words to write the pulse table RAM 344 and to set the contents of various control registers. Integrity of the RAM initialization is verified by use of the checksum feature, and individual control registers may be read back for verification.

The speech processor then performs two sequential writes to the Stimulation Enable Register, with data values of first 0×003 and then 0×100. This is known as the "Mother May I" sequence, and puts the ICS2 in a state where it will commence stimulation upon the receipt of an amplitude word with the SYNC bit set. At this point the speech processor starts sending amplitude words, and stimulation starts once the first frame has been received by the ICS2. There is one additional lockout feature—stimulation cannot start if the CRCBAD (checksum error) bit in the Status Register is set.

CIS Strategy

Figure 27:
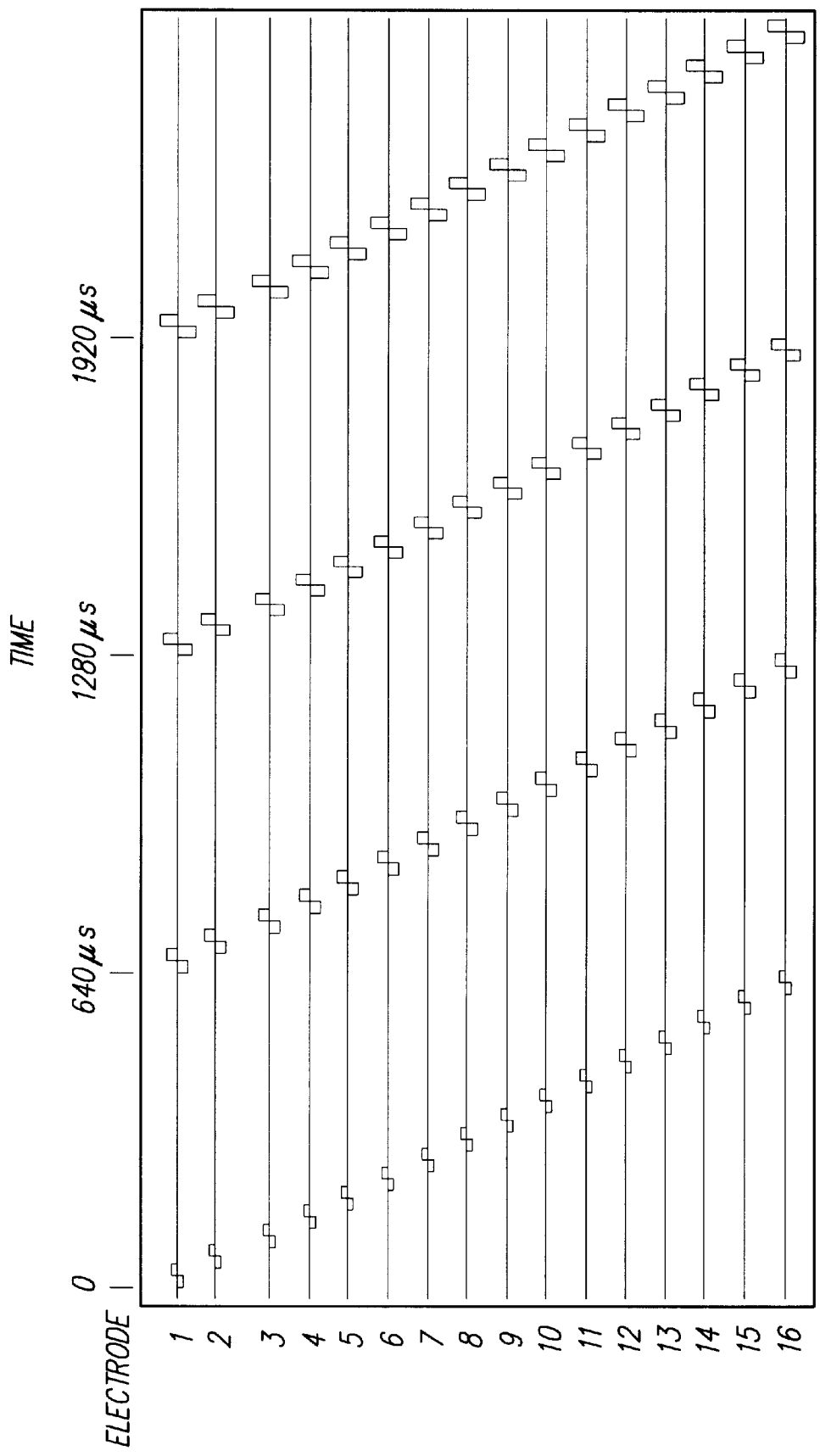
FIG. 27 shows the 16-channel CIS waveform produced using the Pulse Table and amplitude frames shown in FIGS. 26A and 26B.

Next, with reference to FIGS. 26A and 26B, the Pulse Table format (FIG. 26A) and four example amplitude frames (FIG. 26B) for a 16-channel CIS strategy are illustrated. This is a monopolar strategy, where the Indifferent Electrode provides the return path. FIG. 27 illustrates the corresponding waveforms at the electrodes. The times given assume a 20 usec pulse width.

SAS Strategy

Figure 29:
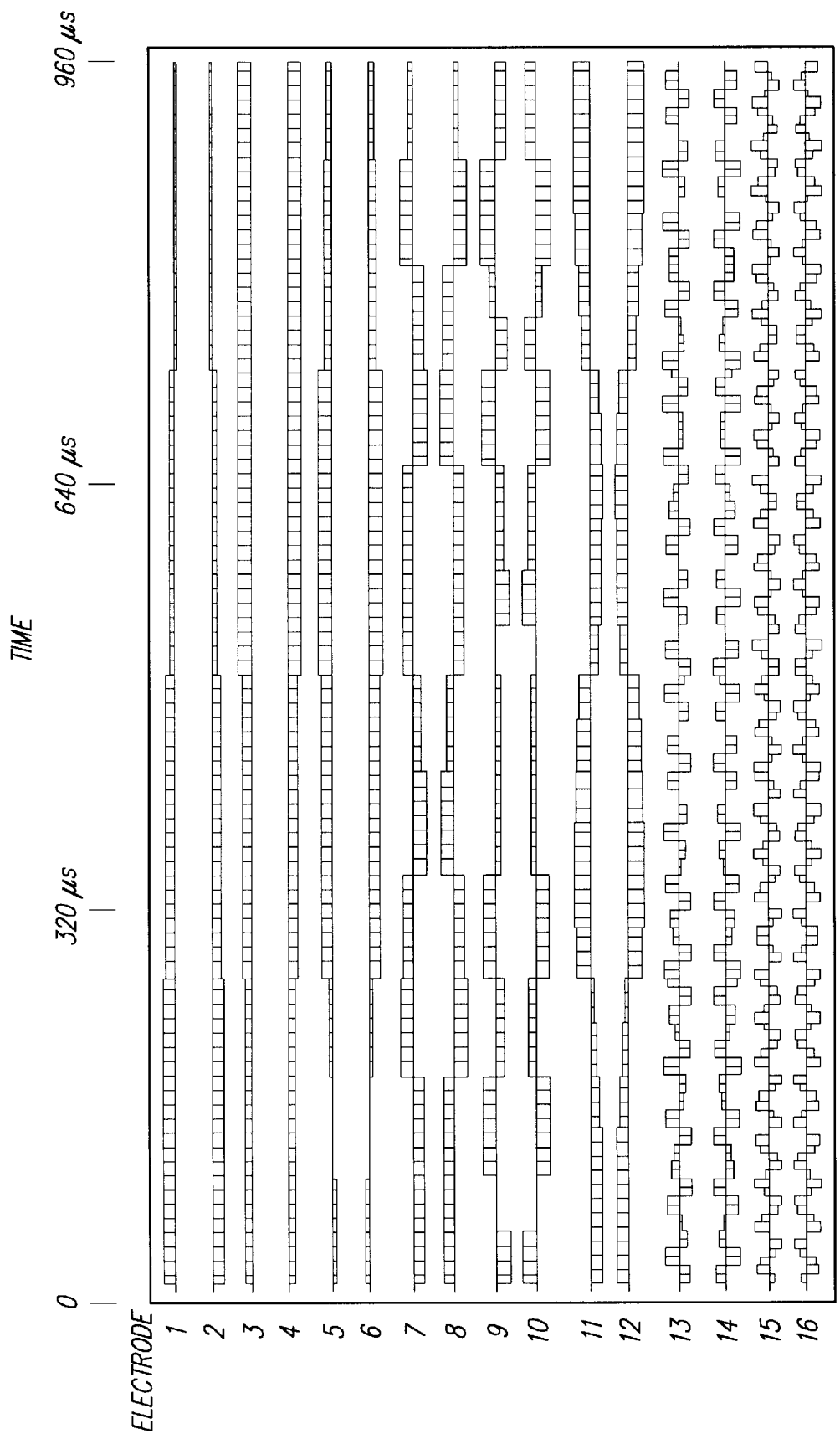
FIG. 29 illustrates the 8-channel SAS waveform produced using the Pulse Table and amplitude frames shown in FIGS. 28A and 28B.

FIG. 28A shows a partial pulse table for an 8-channel SAS strategy. This is a bipolar strategy, where electrodes are paired and the return path is between the two electrodes in each pair. FIG. 28B shows four example amplitude frames for the 8-channel SAS strategy. Finally, FIG. 29 shows the resulting waveform.

Error Handling

The response of the ICS2 to errors is programmable. Errors are broken down into two types, communication and stimulation errors.

Communication errors include the following:
- FT parity error—even parity was detected in a forward telemetry data word.
- Missing edge—no transition was detected at a bit boundary time
- RF level error—no signal transition was seen by the dc-coupled FT detector within the last bit time.

the response to communication errors is usually programmed on a per-error basis. The possible responses include: do nothing; shutdown forward telemetry but continue stimulation; shutdown forward telemetry and "gracefully" shutdown stimulation (allow current amplitude frame to complete first); or perform a global reset (i.e., shut down telemetry and immediately halt stimulation).

Stimulation errors include the following:
- Input underflow error—the pulse table entry with the LOAD bit set was read before a new amplitude frame was received.

- Input overflow error—a second new amplitude frame was received without a pulse table LOAD being executed.
- Stimulation overflow error—an update (pulse width) interval transpired without a pulse table PAUSE bit being executed.

Possible responses to stimulation errors include: do nothing; gracefully shutdown stimulation; immediately shutdown stimulation; or perform a global reset.

When an error occurs, a bit is set in the Error Register. These bits are "sticky" and will remain set until the register is read. Moreover, the error bits are persistent across a global reset, and thus may be read by software after forward-telemetry is reestablished. There is also a bit in the error register to indicate whether a power-on reset has occurred.

Finally, there are several conditions that may be considered errors, but do not generate any automatic response. These include:
- Checksum error in a write.BT Overflow—a read command occurred before a previous back-telemetry data word transmission was completed.
- Limit Hit—the datapath Limiter encountered an input greater than its programmed limit value, and clamped the value.

These conditions are recorded as bits in the Status register, and are "sticky" until read.

As described above, it is thus seen that the present invention provides a multi-channel stimulation system that facilitates the definition/specification of a wide range of different spatiotemporal patterns of electrical stimulation current.

It is further seen that the invention allows complex stimulation waveforms to be defined/specified in a very simple manner.

Moreover, it is seen that the present invention allows some of the speech processing functions to be performed within the implantable portion of the system, thereby reducing the needed bandwidth of the communication link which must be established between the implanted portion and external portions of the cochlear implant system.

While the invention herein disclosed has been described by means of specific embodiments and applications thereof, numerous modifications and variations could be made thereto by those skilled in the art without departing from the scope of the invention set forth in the claims.

What is claimed is:

1. A cochlear implant system comprising:
   an external portion that includes
      an acoustic transducer for sensing acoustic signals and converting them to electrical signals, and
      analog front end (AFE) circuitry for preliminarily processing the electrical signals produced by the acoustic transducer;
   an implantable portion that includes
      an electrode array having a plurality of spaced-apart electrodes for implantation in the cochlea, and
      an implantable cochlear stimulator (ICS) connected to the electrode array for generating electrical stimuli defined by control signals; and
   a speech processor (SP) that generates the control signals used by the ICS;
   wherein the electrical stimuli generated by the ICS are modulated by the sensed acoustic signals in accordance with a selected speech processing strategy; and further wherein
   a portion of the speech processor responsible for defining a portion of the speech processing strategy is located within the implantable portion of the system; whereby only modulation data corresponding to the sensed acoustic signals need be continuously sent to the implantable portion of the system from the external portion of the system during use of the system.

2. The cochlear implant system of claim 1 wherein the portion of the speech processor included within the implantable portion of the system comprises:
   a pulse table wherein a set of coefficients are stored that represent a particular spatiotemporal pattern of stimulus waveforms, and
   a modulator that multiplies the set of coefficients stored in the pulse table with modulation data derived from the sensed acoustic signals to produce a product signal;
   wherein the product signal specifies a particular spatiotemporal pattern of controlled stimulus waveforms associated with the selected speech processing strategy.

3. The cochlear implant system of claim 2 wherein the pulse table comprises a pulse table random access memory (RAM).

4. The cochlear implant system of claim 3 wherein the pulse table RAM comprises an m by n array, where m and n are each integers of at least sixteen.

5. The cochlear implant system of claim 4 wherein n has a value of at least sixteen and m has a value of at least 128.

6. The cochlear implant system of claim 5 further including an amplitude buffer wherein the modulation data is stored as a multiplicity of amplitude words, and further wherein the pulse table RAM stores m pulse table words of at least sixteen bits each, and wherein each bit of the pulse table word belongs to one of multiplicity of fields, and wherein a first of the multiplicity of fields identifies a coefficient to be used by the multiplier, and a second of the multiplicity of fields identifies which of the multiplicity of amplitude words is to be multiplied by the coefficient.

7. The cochlear implant system of claim 6 wherein a third of the multiplicity of fields of the pulse table words identifies which one of the plurality of electrodes on the electrode array is to be acted upon by the product signal obtained from the modulator.

8. The cochlear implant system of claim 7 wherein a fourth of the multiplicity of fields of the pulse table words identifies a bypass flag (PASS), which when set causes the selected amplitude word to bypass the multiplier, thereby effectively producing a "multiply by 1" condition.

9. The cochlear implant system of claim 2 further including
   a neural conditioning pattern stored in a selected location within the pulse table,
   a digital signal generator responsive to the neural conditioning pattern stored in the pulse table that generates a neural conditioning signal;
   an adder that adds the neural conditioning signal to the modulation data.

10. An implantable cochlear stimulator (ICS) comprising:
    an electrode array having a plurality of spaced-apart electrodes for implantation in the cochlea,
    a plurality of pulse generators, wherein each of the pulse generators is connected to a respective one of the plurality of spaced-apart electrodes, and further wherein each pulse generator generates a current having an amplitude and polarity defined by a control signal;
    a pulse table wherein a multiplicity of pulse data words are stored;
    an amplitude buffer wherein a plurality of amplitude words are stored, wherein each amplitude word contains modulation data associated with an externally sensed acoustic signal;

a multiplier coupled to the pulse table and amplitude buffer that multiplies selected portions of a designated amplitude word with a specified pulse data word, the product of said multiplication comprising a control word;

means for directing information contained in the control word to an identified one of said plurality of pulse generators, wherein the control word defines the control signal for the pulse generator to which it is directed;

timing means for controlling when the multiplier and means for directing perform their respective operations;

whereby the pulse data words stored in the pulse table control the spatiotemporal characteristics of the currents generated by the plurality of pulse generators.

11. The ICS as set forth in claim 10 further including means for updating in real time the amplitude words stored in the amplitude buffer, whereby the spatiotemporal characteristics of the currents generated by the plurality of pulse generators may be modulated by information contained within the amplitude words.

12. The ICS as set forth in claim 11 wherein a portion of the pulse data words stored in the pulse table words identifies a bypass flag, which when set causes the modulation data contained within the designated amplitude word to bypass the multiplier, thereby effectively producing a "multiply by 1" condition.

13. The ICS as set forth in claim 11 further including means for updating the pulse data words stored in the pulse table, whereby the spatiotemporal characteristics of the currents generated by the plurality of pulse generators may be modified.

14. The ICS as set forth in claim 11 further including:

a neural conditioning pattern stored in a selected location within the pulse table, a digital signal generator responsive to the neural conditioning pattern stored in the pulse table that generates a neural conditioning signal;

an adder that adds the neural conditioning signal to a selected one of the amplitude words stored in the amplitude buffer.

15. A method of electrically stimulating the cochlea so as to directly stimulate the auditory nerve, thereby producing the sensation of hearing for a deaf patient, the method comprising:

implanting within the patient an electrode array within the cochlea of the patient, the electrode array having a plurality of spaced-apart electrodes;

implanting within the patient a plurality of pulse generators, wherein each of the pulse generators is connected to a respective one of the plurality of spaced-apart electrodes, and further wherein each pulse generator generates a current having an amplitude and polarity defined by a control signal;

implanting within the patient a pulse table wherein a multiplicity of pulse data words are stored, the pulse data words stored in the pulse table containing information that, when acted upon, defines the spatiotemporal characteristics of the currents generated by the plurality of pulse generators, and thereby defines a particular speech processing strategy to be implemented by the method;

implanting within the patient an amplitude buffer wherein a plurality of amplitude words are stored;

sensing acoustical signals external to the patient, and converting the sensed acoustical signals to modulation data;

sending the modulation data, in real time, to the implanted amplitude buffer;

implanting within the patient a multiplier that multiplies selected portions of a designated amplitude word with a specified pulse data word, the product of said multiplication comprising a control word;

directing information contained in the control word to an identified one of said plurality of pulse generators, wherein the control word defines the control signal for the pulse generator to which it is directed;

controlling the timing of when the multiplier multiplies the amplitude words with the pulse data words, and when the resulting control is directed to the pulse generators;

whereby the pulse data words stored in the pulse table, coupled with the controlled timing applied thereto, define the particular spatiotemporal characteristics of the currents generated by the plurality of pulse generators, and further whereby the currents thus generated by the plurality of pulse generators may be modulated with information contained within the amplitude words.

* * * * *

UNITED STATES PATENT AND TRADEMARK OFFICE
CERTIFICATE OF CORRECTION

PATENT NO. : 6,219,580 B1
DATED : April 17, 2001
INVENTOR(S) : Faltys et al.

It is certified that error appears in the above-identified patent and that said Letters Patent is hereby corrected as shown below:

<u>Title page,</u>
Item [75], change the named inventors from:
"Michael A. Faltys; Gerald E. Loeb, both of Northridge; Logan P. Palmer, Santa Monica; Andrew W. Voelkel, Venice, all of CA(US)"

to

-- Michael A. Faltys; Gerald E. Loeb, both of Northridge; Logan P. Palmer, Santa Monica; Andrew W. Voelkel, Venice, James H. Wolfe, Canyon Country; Rankiri T. Karunasiri, Castaic, all of CA(US) --

Signed and Sealed this

Fifteenth Day of October, 2002

*Attest:*

JAMES E. ROGAN
*Attesting Officer*   *Director of the United States Patent and Trademark Office*